United States Patent
Furitsu et al.

(10) Patent No.: US 8,969,379 B2
(45) Date of Patent: Mar. 3, 2015

(54) PHARMACEUTICAL COMPOSITIONS OF 4-(3-CHLORO-4-(CYCLOPROPYLAMINO CARBONYL)AMINOPHENOXY)-7=METHOXY-6-QUINOLINECARBOXIDE

(75) Inventors: Hisao Furitsu, Tsukuba (JP); Yasuyuki Suzuki, Kakamigahara (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1202 days.

(21) Appl. No.: 11/662,425

(22) PCT Filed: Sep. 14, 2005

(86) PCT No.: PCT/JP2005/016941
§ 371 (c)(1),
(2), (4) Date: Apr. 4, 2008

(87) PCT Pub. No.: WO2006/030826
PCT Pub. Date: Mar. 23, 2006

(65) Prior Publication Data
US 2008/0214604 A1   Sep. 4, 2008

(30) Foreign Application Priority Data
Sep. 17, 2004   (JP) ................ P2004-272625

(51) Int. Cl.
*C07D 215/48* (2006.01)
*A61K 31/47* (2006.01)
(Continued)

(52) U.S. Cl.
CPC ............. *A61K 47/02* (2013.01); *A61K 9/2009* (2013.01); *A61K 9/2018* (2013.01); *A61K 9/2054* (2013.01); *A61K 9/2866* (2013.01); *A61K 31/47* (2013.01); *C07D 215/48* (2013.01)
USPC ......................................................... 514/312

(58) Field of Classification Search
CPC ...... C07D 215/48; A61K 31/47; A61K 9/2009
USPC .................................................... 514/312
See application file for complete search history.

(56) References Cited

U.S. PATENT DOCUMENTS

| 4,526,988 A | 7/1985 | Hertel |
| 4,563,417 A | 1/1986 | Albarella et al. |

(Continued)

FOREIGN PATENT DOCUMENTS

| CA | 2 361 057 A1 | 7/2000 |
| CN | 1473041 A | 2/2004 |

(Continued)

OTHER PUBLICATIONS

Sparer et al (JP 06-287148; 1994; English Machine Translation obtained from PAJ; Sep. 22, 2010.*

(Continued)

*Primary Examiner* — Timothy Thomas
(74) *Attorney, Agent, or Firm* — Fish & Richardson P.C.

(57) ABSTRACT

A pharmaceutical composition comprising: an active ingredient consisting of 4-(3-chloro-4-(cyclopropylaminocarbonyl)aminophenoxy)-7-methoxy-6-quinolinecarboxamide, salt thereof, or solvate of the foregoing; and (i) a compound, a 5% (w/w) aqueous solution or suspension of which has a pH of 8 or more, and/or (ii) silicic acid, salt thereof, or solvate of the foregoing is a highly stable pharmaceutical composition, wherein under humidified and heated storage conditions, the decomposition of said compound is sufficiently reduced, or the gelation on the surface of the pharmaceutical composition is sufficiently inhibited.

7 Claims, 6 Drawing Sheets

(51) Int. Cl.
  *A61K 47/02*  (2006.01)
  *A61K 9/20*  (2006.01)
  *A61K 9/28*  (2006.01)

(56) References Cited

U.S. PATENT DOCUMENTS

| | | | |
|---|---|---|---|
| 4,582,789 A | 4/1986 | Sheldon, III et al. | |
| 4,742,003 A | 5/1988 | Derynck et al. | |
| 4,764,454 A | 8/1988 | Ichijima et al. | |
| 5,180,818 A | 1/1993 | Cech et al. | |
| 5,211,951 A * | 5/1993 | Sparer et al. | 424/426 |
| 5,445,934 A | 8/1995 | Fodor et al. | |
| 5,464,826 A | 11/1995 | Grindey et al. | |
| 5,487,889 A | 1/1996 | Eckert et al. | |
| 5,553,037 A | 9/1996 | Tachibana | |
| 5,624,937 A | 4/1997 | Reel et al. | |
| 5,656,454 A | 8/1997 | Lee et al. | |
| 5,658,374 A | 8/1997 | Glover | |
| 5,733,913 A | 3/1998 | Blankley et al. | |
| 5,747,651 A | 5/1998 | Lemischka | |
| 5,750,376 A | 5/1998 | Weiss et al. | |
| 5,770,599 A | 6/1998 | Gibson | |
| 5,792,783 A | 8/1998 | Tang et al. | |
| 5,891,996 A | 4/1999 | Maten de Acosta del Rio et al. | |
| 5,948,438 A * | 9/1999 | Staniforth et al. | 424/464 |
| 6,027,880 A | 2/2000 | Cronin et al. | |
| 6,057,100 A | 5/2000 | Heyneker | |
| 6,143,764 A | 11/2000 | Kubo et al. | |
| 6,156,501 A | 12/2000 | McGall et al. | |
| 6,156,522 A | 12/2000 | Keay et al. | |
| 6,217,866 B1 | 4/2001 | Schlessinger et al. | |
| 6,261,776 B1 | 7/2001 | Pirrung et al. | |
| 6,346,398 B1 | 2/2002 | Pavco et al. | |
| 6,351,255 B1 | 2/2002 | Ishizuka et al. | |
| 6,476,040 B1 | 11/2002 | Norris et al. | |
| 6,524,583 B1 | 2/2003 | Thorpe et al. | |
| 6,534,535 B1 | 3/2003 | Zhu et al. | |
| 6,576,424 B2 | 6/2003 | Fodor et al. | |
| 6,676,941 B2 | 1/2004 | Thorpe et al. | |
| 6,797,823 B1 | 9/2004 | Kubo et al. | |
| 6,811,779 B2 | 11/2004 | Rockwell et al. | |
| 6,812,341 B1 | 11/2004 | Conrad | |
| 6,821,987 B2 | 11/2004 | Kubo et al. | |
| 7,005,430 B2 | 2/2006 | Ueno et al. | |
| 7,101,663 B2 | 9/2006 | Godfrey et al. | |
| 7,135,466 B2 | 11/2006 | Sakai et al. | |
| 7,169,789 B2 | 1/2007 | Kubo et al. | |
| 7,253,286 B2 | 8/2007 | Funahashi et al. | |
| 7,435,590 B2 | 10/2008 | Komurasaki | |
| 7,485,658 B2 | 2/2009 | Bolger et al. | |
| 7,495,104 B2 | 2/2009 | Miwa et al. | |
| 7,547,703 B2 | 6/2009 | Roth et al. | |
| 7,550,483 B2 | 6/2009 | Sakaguchi et al. | |
| 7,612,092 B2 | 11/2009 | Funahashi et al. | |
| 7,612,208 B2 * | 11/2009 | Matsushima et al. | 546/159 |
| 7,855,290 B2 | 12/2010 | Matsushima et al. | |
| 7,973,160 B2 | 7/2011 | Funahashi et al. | |
| 8,288,538 B2 | 10/2012 | Matsushima et al. | |
| 8,372,981 B2 | 2/2013 | Funahashi et al. | |
| 8,377,938 B2 | 2/2013 | Matsushima et al. | |
| 2002/0040127 A1 | 4/2002 | Jiang et al. | |
| 2003/0013208 A1 | 1/2003 | Jendoubi | |
| 2003/0087907 A1 | 5/2003 | Kubo et al. | |
| 2003/0113713 A1 | 6/2003 | Glezer et al. | |
| 2003/0215523 A1 | 11/2003 | Ozawa et al. | |
| 2004/0009965 A1 | 1/2004 | Collins et al. | |
| 2004/0034026 A1 | 2/2004 | Wood et al. | |
| 2004/0053908 A1 | 3/2004 | Funahashi et al. | |
| 2004/0086915 A1 | 5/2004 | Lin et al. | |
| 2004/0132727 A1 | 7/2004 | Sakai et al. | |
| 2004/0152759 A1 | 8/2004 | Abrams et al. | |
| 2004/0167134 A1 | 8/2004 | Bruns et al. | |
| 2004/0171068 A1 | 9/2004 | Wehland et al. | |
| 2004/0191254 A1 | 9/2004 | Fagin | |
| 2004/0224972 A1 | 11/2004 | Ozawa et al. | |
| 2004/0242506 A1 | 12/2004 | Barges Causeret et al. | |
| 2004/0253205 A1 | 12/2004 | Yamamoto et al. | |
| 2004/0259834 A1 | 12/2004 | Kasprzyk et al. | |
| 2005/0014727 A1 | 1/2005 | Muller et al. | |
| 2005/0049264 A1 | 3/2005 | Miwa et al. | |
| 2005/0119303 A1 | 6/2005 | Wakabayashi et al. | |
| 2005/0176802 A1 | 8/2005 | Tang et al. | |
| 2005/0187236 A1 | 8/2005 | Tsuruoka et al. | |
| 2005/0209452 A1 | 9/2005 | Bornsen et al. | |
| 2005/0272688 A1 | 12/2005 | Higgins et al. | |
| 2005/0277652 A1 | 12/2005 | Matsushima et al. | |
| 2006/0004017 A1 | 1/2006 | Stokes et al. | |
| 2006/0004029 A1 | 1/2006 | Tsuruoka et al. | |
| 2006/0057195 A1 | 3/2006 | Nonomura et al. | |
| 2006/0079494 A1 | 4/2006 | Santi et al. | |
| 2006/0135486 A1 | 6/2006 | Owa et al. | |
| 2006/0160832 A1 | 7/2006 | Funahashi et al. | |
| 2006/0178399 A1 | 8/2006 | Nishizawa et al. | |
| 2006/0189629 A1 | 8/2006 | Bolger et al. | |
| 2006/0292192 A1 * | 12/2006 | Hasenzahl et al. | 424/401 |
| 2007/0004773 A1 | 1/2007 | Sakaguchi et al. | |
| 2007/0027318 A1 | 2/2007 | Kubo et al. | |
| 2007/0032521 A1 | 2/2007 | Moussy et al. | |
| 2007/0037849 A1 | 2/2007 | Naito et al. | |
| 2007/0078159 A1 | 4/2007 | Matsushima | |
| 2007/0117842 A1 | 5/2007 | Arimoto et al. | |
| 2008/0207617 A1 | 8/2008 | Miwa et al. | |
| 2008/0214604 A1 | 9/2008 | Furitsu et al. | |
| 2008/0241835 A1 | 10/2008 | Mehraban et al. | |
| 2009/0047278 A1 | 2/2009 | Owa et al. | |
| 2009/0047365 A1 | 2/2009 | Owa et al. | |
| 2009/0053236 A1 | 2/2009 | Yamamoto | |
| 2009/0202541 A1 | 8/2009 | Bruns et al. | |
| 2009/0209580 A1 | 8/2009 | Matsui | |
| 2009/0247576 A1 | 10/2009 | Kamata | |
| 2009/0264464 A1 | 10/2009 | Yamamoto et al. | |
| 2009/0304694 A1 | 12/2009 | Oliner et al. | |
| 2010/0048503 A1 | 2/2010 | Yamamoto | |
| 2010/0048620 A1 | 2/2010 | Yamamoto | |
| 2010/0105031 A1 | 4/2010 | Matsui et al. | |
| 2010/0239688 A1 | 9/2010 | Yamamoto | |
| 2010/0324087 A1 | 12/2010 | Yamamoto | |
| 2011/0118470 A1 | 5/2011 | Funahashi et al. | |
| 2011/0158983 A1 | 6/2011 | Bascomb et al. | |
| 2011/0293615 A1 | 12/2011 | Yamamoto | |
| 2012/0077842 A1 | 3/2012 | Bando | |
| 2012/0207753 A1 | 8/2012 | Yu et al. | |
| 2012/0219522 A1 | 8/2012 | Xi | |
| 2012/0244209 A1 | 9/2012 | Roth et al. | |
| 2012/0263677 A1 | 10/2012 | Eagle et al. | |
| 2012/0283206 A1 | 11/2012 | Bruns et al. | |
| 2013/0296365 A1 | 11/2013 | Bando | |

FOREIGN PATENT DOCUMENTS

| | | |
|---|---|---|
| CN | 1478078 | 2/2004 |
| CN | 1890220 A | 1/2007 |
| CN | 1010010629 A | 7/2007 |
| CN | 101029022 A | 9/2007 |
| CN | 101198590 | 6/2008 |
| CN | 101316590 | 12/2008 |
| CN | 101454311 | 6/2009 |
| CN | 101616671 | 12/2009 |
| CN | 102470133 | 5/2012 |
| EP | 0405425 A2 | 1/1991 |
| EP | 0802851 A1 | 6/1994 |
| EP | 0684637 A2 | 11/1995 |
| EP | 0684820 | 12/1995 |
| EP | 0637863 A1 | 4/1996 |
| EP | 0 712 863 A1 | 5/1996 |
| EP | 0679642 A2 | 10/1996 |
| EP | 0795556 A1 | 9/1997 |
| EP | 0860433 A1 | 8/1998 |
| EP | 0930305 A1 | 7/1999 |
| EP | 0930310 A1 | 7/1999 |
| EP | 1029853 A1 | 8/2000 |
| EP | 0 543 942 | 1/2001 |
| EP | 1153920 A1 | 11/2001 |
| EP | 0 712 863 B1 | 2/2002 |

(56) References Cited

FOREIGN PATENT DOCUMENTS

| | | |
|---|---|---|
| EP | 1 411 046 A1 | 4/2004 |
| EP | 1415987 A1 | 5/2004 |
| EP | 1 447 045 A1 | 8/2004 |
| EP | 1 506 962 A2 | 2/2005 |
| EP | 1522540 A1 | 4/2005 |
| EP | 1 535 910 A1 | 6/2005 |
| EP | 1552833 A1 | 7/2005 |
| EP | 1588379 A1 | 8/2005 |
| EP | 1604665 A1 | 12/2005 |
| EP | 1331005 B1 | 4/2006 |
| EP | 1883785 A1 | 7/2006 |
| EP | 1898623 A1 | 9/2006 |
| EP | 1 777 218 A1 | 4/2007 |
| EP | 1797877 A1 | 6/2007 |
| EP | 1797881 A1 | 6/2007 |
| EP | 1859793 A1 | 11/2007 |
| EP | 1859797 A1 | 11/2007 |
| EP | 1925676 A1 | 5/2008 |
| EP | 1925941 A1 | 5/2008 |
| EP | 1949902 A1 | 7/2008 |
| EP | 1964837 A1 | 9/2008 |
| EP | 2 116 246 A1 | 11/2009 |
| EP | 2 119 707 A1 | 11/2009 |
| EP | 2133094 A1 | 12/2009 |
| EP | 2133095 A1 | 12/2009 |
| EP | 2 218 712 A1 | 8/2010 |
| GB | 2253848 A | 9/1992 |
| JP | 63-28427 A | 2/1988 |
| JP | 64-22874 A | 1/1989 |
| JP | 2-291295 A | 12/1990 |
| JP | 4-341454 A | 11/1992 |
| JP | 8-153952 A | 6/1994 |
| JP | 7-176103 A | 7/1995 |
| JP | 8-45927 A | 2/1996 |
| JP | 8-48078 A | 2/1996 |
| JP | 9-23885 A | 1/1997 |
| JP | 9-234074 A | 9/1997 |
| JP | 11-143429 A | 5/1999 |
| JP | 11-158149 A | 6/1999 |
| JP | 11-322596 A | 11/1999 |
| JP | 3040486 A | 5/2000 |
| JP | 3088018 A | 9/2000 |
| JP | 2000-328080 A | 11/2000 |
| JP | 2001-131071 A | 5/2001 |
| JP | 2002-3365 A | 1/2002 |
| JP | 2002-114710 A | 4/2002 |
| JP | 2002-536414 A | 10/2002 |
| JP | 2003-12668 A | 1/2003 |
| JP | 2003-26576 A | 1/2003 |
| JP | 2003-033472 | 2/2003 |
| JP | 3420549 B2 | 6/2003 |
| JP | 2003-525595 A | 9/2003 |
| JP | 2004-513964 A | 5/2004 |
| JP | 2004-531549 A | 10/2004 |
| JP | 2005-272474 | 10/2004 |
| JP | 2005-501074 A | 1/2005 |
| JP | 2005-504111 A | 2/2005 |
| JP | 2005-520834 A | 7/2005 |
| JP | 3712393 B2 | 8/2005 |
| JP | 2006-508981 A | 3/2006 |
| JP | 2006-515884 A | 8/2006 |
| KR | 10-0589032 | 11/2005 |
| WO | WO 92/20642 A1 | 11/1992 |
| WO | WO 94/09010 A1 | 4/1994 |
| WO | WO 95/15768 A1 | 6/1995 |
| WO | WO 95/17181 A1 | 6/1995 |
| WO | WO 95/19774 A1 | 7/1995 |
| WO | WO 96/09294 A1 | 3/1996 |
| WO | WO-96/26997 A1 | 9/1996 |
| WO | WO 96/30347 A1 | 10/1996 |
| WO | WO 96/33980 A1 | 10/1996 |
| WO | WO 96/39145 A1 | 12/1996 |
| WO | WO 96/40142 A1 | 12/1996 |
| WO | WO 97/03069 A1 | 1/1997 |
| WO | WO 97/13760 A1 | 4/1997 |
| WO | WO 97/13771 A1 | 4/1997 |
| WO | WO 97/17329 A1 | 5/1997 |
| WO | WO 97/21437 A1 | 6/1997 |
| WO | WO 97/38984 A1 | 10/1997 |
| WO | WO 97/48693 A1 | 12/1997 |
| WO | WO 98/00134 A1 | 1/1998 |
| WO | WO 98/02434 A1 | 1/1998 |
| WO | WO 98/02437 A1 | 1/1998 |
| WO | WO 98/02438 A1 | 1/1998 |
| WO | WO 98/13350 A1 | 4/1998 |
| WO | WO 98/14437 A1 | 4/1998 |
| WO | WO 98/23613 A1 | 6/1998 |
| WO | WO 98/32436 A1 | 7/1998 |
| WO | WO 98/35958 A1 | 8/1998 |
| WO | WO 98/37079 A1 | 8/1998 |
| WO | WO 98/50346 A2 | 11/1998 |
| WO | WO 98/52558 A1 | 11/1998 |
| WO | WO 99/00357 A1 | 1/1999 |
| WO | WO 99/32106 A1 | 7/1999 |
| WO | WO 99/32110 A1 | 7/1999 |
| WO | WO 99/32111 A1 | 7/1999 |
| WO | WO 99/32436 A1 | 7/1999 |
| WO | WO 99/35132 A1 | 7/1999 |
| WO | WO 99/35146 A1 | 7/1999 |
| WO | WO 99/43654 A2 | 9/1999 |
| WO | WO 99/62890 A2 | 12/1999 |
| WO | WO 00/31048 A1 | 6/2000 |
| WO | WO 00/42012 A1 | 7/2000 |
| WO | WO 00/43366 A1 | 7/2000 |
| WO | WO 00/43384 A1 | 7/2000 |
| WO | WO 00/44728 A1 | 8/2000 |
| WO | WO 00/47212 A1 | 8/2000 |
| WO | WO 00/50405 A1 | 8/2000 |
| WO | WO-00/71097 A1 | 11/2000 |
| WO | WO 00/71097 A1 | 11/2000 |
| WO | WO 01/02369 A2 | 1/2001 |
| WO | WO 01/23375 A2 | 4/2001 |
| WO | WO 01/27081 A1 | 4/2001 |
| WO | WO 01/32926 A2 | 5/2001 |
| WO | WO 01/38403 A1 | 5/2001 |
| WO | WO 01/40217 A1 | 6/2001 |
| WO | WO 01/47890 A1 | 7/2001 |
| WO | WO 01/47931 A1 | 7/2001 |
| WO | WO 01/45889 A2 | 8/2001 |
| WO | WO 01/60814 A2 | 8/2001 |
| WO | WO 02/16346 A1 | 2/2002 |
| WO | WO-02/32872 A1 | 4/2002 |
| WO | WO 02/36117 A1 | 5/2002 |
| WO | WO 02/41882 A2 | 5/2002 |
| WO | WO 02/44156 A2 | 6/2002 |
| WO | WO 02/072578 A2 | 9/2002 |
| WO | WO 02/080975 A1 | 10/2002 |
| WO | WO 02/088110 A1 | 11/2002 |
| WO | WO 02/092091 A1 | 11/2002 |
| WO | WO 03/006462 A1 | 1/2003 |
| WO | WO 03/013529 A1 | 2/2003 |
| WO | WO 03/027102 A1 | 4/2003 |
| WO | WO 03/028711 A2 | 4/2003 |
| WO | WO 03/033472 A1 | 4/2003 |
| WO | WO 03/050090 A1 | 6/2003 |
| WO | WO 03/074045 A1 | 9/2003 |
| WO | WO 03/079020 A2 | 9/2003 |
| WO | WO 2004/006862 A2 | 1/2004 |
| WO | WO 2004/020434 A1 | 3/2004 |
| WO | WO 2004/032872 A2 | 4/2004 |
| WO | WO 2004/032937 A1 | 4/2004 |
| WO | WO-2004/035052 A1 | 4/2004 |
| WO | WO 2004/039762 A1 | 5/2004 |
| WO | WO 2004/041308 A1 | 5/2004 |
| WO | WO 2004/043472 A1 | 5/2004 |
| WO | WO 2004/064730 A2 | 8/2004 |
| WO | WO 2004/078144 A2 | 9/2004 |
| WO | WO 2004/080462 A1 | 9/2004 |
| WO | WO 2004/080988 A1 | 9/2004 |
| WO | WO-2004/101526 A1 | 11/2004 |
| WO | WO 2005/004870 A1 | 1/2005 |
| WO | WO 2005/021537 | 3/2005 |
| WO | WO 2005/027972 A2 | 3/2005 |
| WO | WO 2005/030140 A2 | 4/2005 |

(56) References Cited

FOREIGN PATENT DOCUMENTS

| WO | WO-2005/044788 A1 | 5/2005 |
|---|---|---|
| WO | WO 2005/051366 A2 | 6/2005 |
| WO | WO 2005/056764 A2 | 6/2005 |
| WO | WO-2005/063713 A1 | 7/2005 |
| WO | WO 2005/082854 A1 | 9/2005 |
| WO | WO 2005/092896 A1 | 10/2005 |
| WO | WO 2005/117887 A1 | 12/2005 |
| WO | WO 2006/030941 A1 | 3/2006 |
| WO | WO 2006/030947 A1 | 3/2006 |
| WO | WO 2006/036941 A2 | 4/2006 |
| WO | WO 2006/062984 A2 | 6/2006 |
| WO | WO 2006/090930 A1 | 8/2006 |
| WO | WO 2006/090931 A1 | 8/2006 |
| WO | WO-2006/137474 A1 | 12/2006 |
| WO | WO 2007/000347 | 1/2007 |
| WO | WO 2007/014335 A2 | 2/2007 |
| WO | WO 2007/015569 A1 | 2/2007 |
| WO | WO 2007/015578 A1 | 2/2007 |
| WO | WO 2007/023768 | 3/2007 |
| WO | WO 2007/040565 A2 | 4/2007 |
| WO | WO 2007/052849 A1 | 5/2007 |
| WO | WO 2007/052850 A1 | 5/2007 |
| WO | WO 2007/061127 A1 | 5/2007 |
| WO | WO 2007/061130 A1 | 5/2007 |
| WO | WO 2007/136103 A1 | 11/2007 |
| WO | WO 2008/023698 | 2/2008 |
| WO | WO 2008/026748 A1 | 3/2008 |
| WO | WO 2008/030828 A1 | 3/2008 |
| WO | WO 2008/088088 | 7/2008 |
| WO | WO 2008-093855 A1 | 8/2008 |
| WO | WO 2009/060945 | 5/2009 |
| WO | WO 2009/077874 | 6/2009 |
| WO | WO 2009/096377 | 8/2009 |
| WO | WO 2009/140549 A1 | 11/2009 |

OTHER PUBLICATIONS

O'Reilly et al.; "Hydrolysis of tert-Butyl Methyl Ether (MTBE) in Dilute Aqueous Acid"; 2001; Environ. Sci. Technol.; 35: 3954-3961.*

Patel et al.; "The effect of excipients on the stability of levothyroxine sodium pentahydrate tablets"; 2003; International Journal of Pharmaceutics; 264: 35-43.*

Carey; "Organic Chemistry 4e: Chapter 24:Phenols"; 2000; McGraw Hill; http://www.mhhe.com/physsci/chemistry/carey/student/olc/ch24reactionsarylethers.html, accessed Oct. 3, 2014.*

Bajwa et al.; "Animalarials. 1. Heterocyclic Analogs of N-Substituted Naphthalenebisoxazines"; Journal of Medicinal Chemistry; 1972; 16(2): 134-138.*

Burwell; "The Cleavage of Ethers"; Chem. Rev., 1954, 54 (4), pp. 615-685.*

Abuzar et al., "Synthesis of some new 7-chloro-4-substituted quinolines as potential antiparasitic agents (1)," Eur. J. Med. Chem., vol. 21, No. 1, pp. 5-8, 1986.

Bellone et al., "Growth stimulation of colorectal carcinoma cells via the c-kit receptor is inhibited by TGF-beta1", J. Cell. Physiol., vol. 172, pp. 1-11, 1997.

Berdel et al., "Recombinant Human Stem Cell Factor Stimulates Growth of a Human Glioblastoma Cell Line Expressing c-kit Protooncogene," Cancer Research, vol. 52, pp. 3498-3502, Jun. 15, 1992.

Blume-Jensen et al., "Activation of the human c-kit product by ligand-induced dimerization mediates circular actin reorganization and chemotaxis," EMBO J., vol. 10, No. 13, pp. 4121-4128, 1991.

Boissan et al., "c-Kit and c-kit mutations in mastocytosis and other hematological diseases," J. Leukoc. Biol., vol. 67, pp. 135-148, Feb. 2000.

Bussolino et al., "Role of Soluble Mediators in Angiogenesis," Eur. J. Cancer, vol. 32A, No. 14, pp. 2401-2412, 1996.

Cairns et al., "New antiallergic pyrano[3,2-g]quinoline-2,8-dicarboxylic acids with potential for the topical treatment of asthma," J. Med. Chem., vol. 28, pp. 1832-1842, Dec. 1985.

Chinese Office Action for Application No. 2007100070979 dated Mar. 6, 2009.

Ciardiello et al., "ZD1839 (IRESSA), an EGFR-selective tyrosine kinase inhibitor, enhances taxane activity in bcl-2 overexpressing, multidrug-resistant MCF-7 ADR human breast cancer cells," Int. J. Cancer, vol. 98, No. 3, pp. 463-469, Mar. 20, 2002.

Clark et al., "Safety and Pharmacokinetics of the Dual Action Rat Kinase and Vascular Endothelial Growth Factor Receptor Inhibitor, BAY 43-9006, in Patients with Advanced, Refractory Solid Tumors," Clin Cancer Res., vol. 11, No. 15, pp. 5472-5480, Aug. 1, 2005.

Cohen et al., "Expression of Stem Cell Factor and c-kit in Human Neuroblastoma," Blood, vol. 84, No. 10, pp. 3465-3472. Nov. 15, 1994.

Croom et al., "Imatinib Mesylate: In the Treatment of Gastrointestinal Stromal Tumours," Drugs, vol. 63, No. 5, pp. 513-522, 2003.

Deplanque et al., "Anti-angiogenic agents: clinical trial design and therapies in development," Eur. J. Cancer, vol. 36, pp. 1713-1724, 2000.

Dermer, "Another Anniversary for the War on Cancer," Biotechnology, vol. 12, pp. 320. Mar. 12, 1994.

European Office Action for Application No. 04025700 8 dated Apr. 10, 2006.

European Search Report for Application No. 04719054 1 dated Apr. 17, 2009.

European Search Report for Application No. 04818213.3 dated Jul. 30, 2007.

European Search Report for Application No. 06832529.9 dated Jul. 29, 2009.

Folkman et al., "Angiogenesis," J. Biol. Chem., vol. 267, No. 16, pp. 10931-10934, Jun. 5, 1992.

Folkman, "New Perspectives in Clinical Oncology from Angiogenesis Research," Eur. J. Cancer, vol. 32A, No. 14, pp. 2534-2539, 1996.

Folkman, "Seminars in Medicine of the Beth Israel Hospital, Boston, Clinical applications of research on angiogenesis," N. Engl. J. Med, vol. 333 No. 26, pp. 1757-1763, Dec. 28, 1995.

Folkman, "What is the Evidence That Tumors are Angiogenesis Dependent?," J. Natl. Cancer Inst., vol. 82, No. 1, pp. 4-6, Jan. 3, 1990.

Freshney, "Culture of Animal Cells a Manual of Basic Technique," Alan R. Liss, New York, pp. 29-32, 1983.

Furitsu et al., "Stable medicinal compositions of quinolinecarboxamide derivative", Database CAPLUS Abstract, Columbus, Ohio, US, 2006.

Furitsu et al., "Identification of Mutations in the Coding Sequence of the Proto-Oncogene c-kit in a Human Mast Cell Leukemia Cell Line Causing Ligand-Independent Activation of c-kit Product", J. Clin Invest., vol. 92, pp. 1736-1744, 1993.

Furuta et al., "Synthesis and Biological Evaluation of Selective Inhibitors of PDGF Receptor Auto Phosphorylation," Abstract No. 64, Pharmaceutical Research Laboratories, Kirin Brewery Co., Ltd Takasaki, Gunma, Japan, 226th ACS National Meeting, New York, NY, Sep. 7-11, 2003.

Gall-Istok et al., "Notes on the synthesis of 4-amino-6,7-di-sec-butoxyquinoline,-6,7-methylenedioxyquinoline and its N-alkylaminoacetyl derivatives," Acta Chimica Hungarica, vol. 112, No. 2, pp. 241-247, 1983.

Gardner et al , "In Vitro Activity of Sorghum-Selective Fluorophenyl Urea Herbicides," Pestic. Biochem. Physiol., vol. 24, pp. 285-297, 1985.

Golkar et al., "Mastocytosis," Lancet, vol. 349, pp. 1379-1385, May 10, 1997.

Gura, "Systems for identifying new drugs are often faulty," Science, vol. 278, No. 5340, pp. 1041-1042, Nov. 7, 1997.

Haleblian, "Characterization of Habits and Crystalline Modification of Solids and Their Pharmaceutical Applications," J. Pharma Sci., vol. 64, No. 8, pp. 1269-1288, Aug. 1975.

Hamel et al , "The road less travelled: c-kit and stem cell factor," J. Neurooncol., vol. 35, pp. 327-333, 1997.

Hayek et al , "An in vivo model for study of the angiogenic effects of basic fibroblast growth factor," Biochem. Biophys. Res. Commun., vol. 147, No. 2, pp. 875-880, Sep. 15, 1987.

(56) References Cited

OTHER PUBLICATIONS

Heinrich et al., "Inhibition of c-kit receptor tyrosine kinase activity by STI 571, a selective tyrosine kinase inhibitor," Blood, vol. 96, No. 3, pp. 925-932, Aug. 1, 2000.
Heinrich et al., "Inhibition of KIT Tyrosine Kinase Activity: A Novel Approach to the Treatment of KIT-Positive Malignancies," J. Clin. Oncol. vol. 20, No. 6, pp. 1692-1703, Mar. 15, 2002.
Hibi et al., "Coexpression of the stem cell factor and the c-kit genes in small-cell lung cancer," Oncogene, vol. 5, pp. 2291-2296, 1991.
Hines et al., "Coexpression of the c-kit and Stem Cell Factor Genes in Breast Carcinomas," Cell Growth Differ., vol. 6, pp. 769-779, Jun. 1995.
Hogaboam et al., "Novel Role of Transmembrane SCF for Mast Cell Activation and Eotaxin Production in Mast Cell-Fibroblast Interactions," J. Immunol., vol. 160, pp. 6166-6171, 1998.
Ikeda et al., "Changes in phenotype and proliferative potential of human acute myeloblastic leukemia cells in culture with stem cell factor," Exp. Hematol., vol. 21, pp. 1686-1694, 1993.
Ikeda et al., "Expression and Functional Role of the Proto-oncogene c-kit in Acute Myeloblastic Leukemia Cells," Blood, vol. 78, No. 11, pp. 2962-2968, Dec. 1, 1991.
International Preliminary Report on Patentability and Written Opinion of the International Searching Authority for Application No. PCT/JP2004/003087 dated on Feb. 13, 2006.
International Preliminary Report on Patentability and Written Opinion of the International Searching Authority for Application No. PCT/JP2006/312487 dated Dec. 24, 2007.
International Search Report for Application No. PCT/JP01/09221 dated Jan. 15, 2002.
International Search Report for Application No. PCT/JP2004/003087 dated Jul. 13, 2004.
Jakeman et al., "Developmental expression of binding sites and messenger ribonucleic acid for vascular endothelial growth factor suggests a role for this protein in vasculogenesis and angiogenesis," Endocrinology, vol. 133, No. 2, pp. 848-859, Aug. 1993.
Japanese Office Action for Application No. 2005-515330 dated Apr. 21, 2009.
Kanakura et al., "Expression, Function and Activation of the Proctooncogene c-Kit Product in Human Leukemia Cells," Leuk. Lymphoma, vol. 10, pp. 35-41, May 1993.
Kay et al., "Eosinophils and Eosinophil-Associated Cytokines in Allergic Inflammation," Int Arch Allergy Immunol , vol. 113, pp. 196-199, 1997.
Kitamura et al., "Regulation of Development, Survival and Neoplastic Growth of Mast Cells through the c-kit Receptor," Int. Arch. Allergy. Immunol., vol. 107, pp. 54-56, 1996.
Kolibaba et al , "Protein tyrosine kinases and cancer," Biochim. Biophys. Acta., vol. 1333, pp. F217-F248, Dec. 1997.
Korean Office Action for Application No. 10-2007-7013993 dated Jul. 31, 2007.
Kotva et al., "Substances with Antineoplastic Activity, LIII, N-(δ-(4-Pyrrolo[2,3-d]Pyrimidinylthio)Valery) Amino Acids and Analogous Derivatives of Di- and Triglycine," Collection Czechoslov, Chem Commun., vol. 38, pp. 1438-1444, 1973.
Lasota et al., "Mutations in Exons 9 and 13 of KIT Gene Are Rare Events in Gastrointestinal Stromal Tumors: A Study of 200 Cases," Am J. Pathol., vol. 157, No. 4, pp. 1091-1095, Oct. 2000.
Lev et al., "A specific combination of substrates is involved in signal transduction by the kit-encoded receptor," EMBO J., vol. 10, No. 3, pp. 647-654, 1991.
Li et al., "Abbrogation of c-kit/Steel factor-dependent tumorigenesis by kinase defective mutants of the c-kit receptor: c-kit kinase defective mutants as candidate tools for cancer gene therapy," Cancer Res., vol. 56, pp. 4343-4346, Oct. 1, 1996.
Longley et al , "Altered Metabolism of Mast-Cell Growth Factor (c-kit Ligand) in Cutaneous Mastocytosis," N. Engl. J. Med., vol. 328, pp. 1302-1307, May 6, 1993.
Longley et al., "Classes of c-KIT activating mutations: proposed mechanisms of action and implications for disease classification and therapy," Leukemia Res., vol. 25, pp. 571-576, 2001.
Longley et al., "Somatic c-KIT activating mutation in urticaria pigmentosa and aggressive mastocytosis: establishment of clonality in a human mast cell neoplasm," Nat. Genet., vol. 12, pp. 312-314, Mar. 1996.
Lukacs et al., "Stem cell factor (c-kit ligand) influences eosinophil recruitment and histamine levels in allergic airway inflammation," J. Immunol., vol. 156, pp. 3945-3951, May 1996.
Matsui et al., "E7080(ER-203492-00), a Novel VEGF Receptor Tyrosine Kinase Inhibitor-I. Characterization as an Angiogenesis Inhibitor," Abstract # 51, AACR, Washington, DC, Jul. 11-14, 2003.
Matsui et al., "E7080, a novel multi-receptor Tyrosine Kinases Inhibitor, inhibited in vitro / in vivo VEGF- and SCF-driven angiogenesis in SCLC cell line," Abstract #146, EORTC-NCI-AACR, Geneva, Switzerland, Sep. 28-Oct. 1, 2004.
Matsui et al., "Quantitative analysis of the profile of tumor vessels may be useful as predictive biomarkers for E7080, a KDR Tyrosine Kinase Inhibitor," Abstract #4631, 98th AACR Annual Meeting, Los Angeles, CA, Apr. 14-18, 2007.
Matsui et al., "VEGFRs inhibitor E7080 inhibits lymph node metastasis of human breast carcinoma, by preventing murine lymphatic endothelial cells from lymphangiogenesis," Abstracts # PD12-8, 18th EORTC-NCI-AACR Symposium on "Molecular Targets and Cancer Therapeutics", Prague, Czech republic Nov. 7-10, 2006.
Matsui et al , "E7080, a novel inhibitor that targets multiple kinases has potent antitumor activities against stem cell factor producing human small cell lung cancer, H146, based on angiogenesis inhibition", International J. Cancer, vol. 122, pp. 664-671, 2008.
Meltzer, "The pharmacological basis for the treatment of perennial allergic rhinitis and non-allergic rhinitis with topical corticosteroids," Allergy, vol. 52, Suppl. 36, pp. 33-40, 1997.
Mendel et al., "In Vivo Antitumor Activity of SU11248, a Novel Tyrosine Kinase Inhibitor Targeting Vascular Endothelial Growth Factor and Platelet-derived Growth Factor Receptors: Determination of a Pharmacokinetic/Pharmacodynamic Relationship," Clin. Cancer Res., vol. 9, pp. 327-337, Jan. 2003.
Metcalf, "Lineage commitment in the progeny of murine hematopoietic preprogenitor cells: Influence of thrombopoietin and interleukin 5," Proc. Natl. Acad. Sci. USA, vol. 95, pp. 6408-6412, May 1998.
Metcalfe et al., "Mast Cells," Physiological Reviews, vol. 77, No. 4, pp. 1033-1079, Oct. 1997.
Metcalfe, "Classification and Diagnosis of Mastocytosis: Current Status," J. Invest. Dermatol., vol. 96, pp. 2S-4S, 1991.
Miyazaki et al., "Synthesis, Structure and Biological Activity Relationship of E7080 and its Derivatives as Novel and Potent Antiangiogenic Protein Tyrosine Kinase Inhibitors Including the VEGF Receptors. FGFR1 Receptor and PDGF Receptor," Abstract B-15, AIMECS03, Kyoto, Japan, Oct. 14-17, 2003.
Myers et al., "The Preparation and SAR of 4-(Anilino), 4-(Phenoxy), and 4-(Thiophenoxy)-Quinazolines inhibitors of p56lck and EGF-R Tyrosine Kinase Activity," Bioorg. Med. Chem. Letts., vol. 7, No. 4, pp. 417-420, 1997.
Naclerio et al., "Rhinitis and Inhalant Allergens," JAMA, vol. 276, No. 22, pp. 1842-1848, Dec. 10, 1997.
Nagata et al., "Elevated expression of the proto-oncogene c-kit in patients with mastocytosis," Leukemia, vol. 12, pp. 175-181, 1998.
Nakamura et al., "E7080(ER-203492-00), a Novel VEGF Receptor Tyrosine Kinase Inhibitor-II. Effects on Growth of Human Tumor Xenografts and Life Span of Mice in Colon 38 Orthotopic Transplantation Model," Abstract # 52, AACR, Toronto, Canada, Apr. 5-9, 2003.
Naruse et al., "Antitumor activity of the selective epidermal growth factor receptor-tyrosine kinase inhibitor (EGFR-TKI) IRESSA (ZD1839) in an EGFR-expressing multidrug-resistant cell line in vitro and in vivo," Int. J. Cancer, vol. 98, No. 2, pp. 310-315, Mar. 10, 2002.
Natali et al., "Breast Cancer is Associated with Loss of the c-kit Oncogene Product," Int. J. Cancer, vol. 52, pp. 713-717, 1992.
NCBI GeneBank Accession No. NM_000222, Feb. 11, 2008.
Nocka et al., "Expression of c-kit gene products in known cellular targets of W mutations in normal and W mutant mice—evidence for an impaired c-kit kinase in mutant mice," Genes. Dev., vol. 3, pp. 816-825, Jun. 1989.

(56) References Cited

OTHER PUBLICATIONS

Nugiel et al., "Synthesis and Evaluation of Indenopyrazoles as Cyclin-Dependent Kinase Inhibitors. 2. Probing the Indeno Ring Substituent Pattern," J. Med. Chem., vol. 45, pp. 5224-5232. 2002.
Okayama et al , "Activation of Eosinophils with Cytokines Produced by Lung Mast Cells," Int. Arch. Allergy Immunol., vol. 114, Suppl. 1, pp. 75-77, 1997.
Okayama et al., "Human Lung Mast Cells are Enriched in the Capacity to Produce Granulocyte-Macrophage Colony-Stimulating Factor in Response to IgE-Dependent Stimulation", Eur. J. Immunol., vol. 26, pp. 708-715, 1998.
Redefining the Frontiers of Science 94th Annual Meeting, American Associations for Cancer Research, vol. 44, 2nd Edition, Washington Convention Center, Washington, D.C., pp. 10-11, Jul. 11-14, 2003.
Scheijen et al., "Tyrosine kinase oncogenes in normal hematopoiesis and hematological disease," Oncogene, vol. 21, pp. 3314-3333, 2002.
Sekido et al., "Preferential Expression of c-kit Protooncogene Transcripts in Small Cell Lung Cancer," Cancer Res., vol. 51, pp. 2416-2419, May 1, 1991.
Spacey et al., "Indolocarbazoles: Potent and Selective Inhibitors of Platelet-Derived Growth Factor Receptor Autophosphorylation," Biochem. Pharmacol., vol. 55, pp. 261-271, 1998.
Strohmeyer et al., "Expression of the hst-1 and c-kit Protooncogenes in Human Testicular Germ Cell Tumors," Cancer Res., vol. 51, pp. 1811-1816, Apr. 1, 1991.
Taguchi et al., "A novel orally active inhibitor of VEGF receptor tyrosine kinases KRN951: Anti-angiogenic and anti-tumor activity against human solid tumors," Proc. Amer. Assoc. Cancer Res., vol. 45, pp. 595-596, Mar. 2004.
Taniguchi et al., "Effect of c-kit Mutation on Prognosis of Gastrointestinal Stromal Tumors," Cancer Res., vol. 59, pp. 4297-4300, Sep. 1, 1999.
Thomas et al., "The Eosinophil and its Role in Asthma," Gen. Pharmac., vol. 27, No. 4, pp. 593-597, 1996.
Tian et al., "Activating c-Kit Gene Mutations in Human Germ Cell Tumors," Am. J. Pathol., vol. 154, No. 6, pp. 1643-1647, Jun. 1999.
Tonary et al., "Lack of Expression of c-Kit in Ovarian Cancers in Associated with Poor Progonosis," Int. J. Cancer (Pred. Oncol.), vol. 89, pp. 242-250, 2000.
Types of Lung Cancer, Cancer Care, Inc., http://www.lungcancer.org/reading/types.php, Aug. 13, 2009.
U.S. Office Action dated Aug. 20, 2009 for U.S. Appl. No. 10/797,903, filed Mar. 10, 2004.
U.S. Office Action dated Dec. 11, 2007 for U.S. Appl. No. 10/797,903, filed Mar. 10, 2004.
U.S. Office Action dated Feb. 9, 2009 for U.S. Appl. No. 11/347,749, filed Feb. 3, 2006.
U.S. Office Action dated Mar. 31, 2010 for U.S. Appl. No. 12/400,562, filed Mar. 9, 2009.
U.S. Office Action dated Sep. 23, 2008 for U.S. Appl. No. 10/577,531, filed Apr. 28, 2006.
Wakeling et al., "ZD1839 (Iressa): An Orally Active Inhibitor of Epidermal Growth Factor Signalling with Potential for Cancer Therapy," Cancer Res., vol. 62, pp. 5749-5753, Oct. 15, 2002.
Wang et al., "The Expression of the Proto-Oncogene C-Kit in the Blast Cells of Acute Myeloblastic Leukemia," Leukemia, vol. 3, No. 10, pp. 699-702, Oct. 1989.
Wang et al., "A Convenient Set of Bidentate Pyridine Ligands for Combinatorial Synthesis", Tetrahedron Lett., vol. 40, pp. 4779-4782, 1999.
Wedge et al., "AZD2171: A Highly Potent, Orally Bioavailable, Vascular Endothelial Growth Factor Receptor-2 Tyrosine Kinase Inhibitor for the Treatment of Cancer," Cancer Res., vol. 65, No. 10, pp. 4389-4400, May 15, 2005.
Yamamoto et al., "E7080 (ER-203492-00), a Novel VEGF Receptor Tyrosine Kinase Inhibitor-III. Significant prolongation of life span in mice transplanted with human ovarian carcinoma based on inhibition of VEGF signaling," Abstract # 50, AACR, Toronto, Canada, Apr. 5-9, 2003.
Yamamoto et al., "E7080 a novel multitargeted tyrosine kinase inhibitor, has direct anti-tumor efficacy via inhibition of KIT signaling in small cell lung cancer," Abstract #4636, AACR, Orlando, FL. Mar. 27-31, 2004.
Yamamoto et al., "E7080, an oral multi-targeted tyrosine kinase inhibitor, has directed anti-tumor efficacy via inhibition of KIT signaling in gastrointestinal stromal tumor (GIST)," Abstract #4038, 97th annual meeting AACR, Washington, DC., Apr. 1-5, 2006.
Yamamoto et al., "E7080, an oral multitargeted tyrosine kinase inhibitor, has direct anti-tumor efficacy via inhibition of KIT signaling in small cell lung cancer," Proceedings of the American Association for Cancer Research, vol. 45, Abstract #4636, pp. 1070-1071, Mar. 2004.
Anderson et al., "Preparation of Water-soluble Compounds through Salt Formation, the Practice of Medicinal Chemistry," Technomics, Sep. 25, 1999, pp. 347-349 and 355-356.
Office Action issued Jun. 1, 2010, in corresponding Japanese Patent Application No. P2005-516605 (with partial translation).
"A Study of E7080 Alone, and in Combination with Everolimus in Subjects with Unresectable Advanced or Metastatic Renal Cell Carcinoma . . . ," National Institutes of Health, Food and Drug Administration, National Library of Medicine, http://clinicaltrials.gov/ct2/show/NCT01136733, May 26, 2010.
Di Lorenzo et al., "Targeted Therapy in the Treatment of Metastatic Renal Cell Cancer," Oncology (2009), vol. 77 (suppl 1), pp. 122-131.
Kanai et al., "Current status and future perspective of molecular targeted therapy for hepatocellular carcinoma," Journal of the Japanese Society of Gastroenterology (2009), vol. 106, pp. 1727-1735, with English translation.
Lennartsson et al., "The Stem Cell Factor Receptor/c-Kit as a Drug Target in Cancer," Current Cancer Drug Targets (2006), vol. 6, pp. 561-571.
Siegel et al. "Sorafenib: Where Do We Go from Here?," Hepatology (2010), vol. 52, pp. 360-369.
Turner et al., "Fibroblast growth factor signalling: from development to cancer," Nature (Feb. 2010), vol. 10, pp. 116-129.
Wells et al., "Targeting the RET Pathway in Thyroid Cancer," Clin Cancer Res (2009), vol. 15, pp. 7119-7123.
European Search Report in European Application No. 06768437.3 issued on Oct. 11, 2010.
Hennequin et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 2002, vol. 45, No. 6, pp. 1300-1312.
Office Action in U.S. Appl. No. 11/997,719 mailed Sep. 3, 2010.
Traxler et al., "AEE788: A Dual Family Epidermal Growth Factor Receptor/ErbB2 and Vascular Endothelial Growth Factor Receptor Tyrosine Kinase Inhibitor with Antitumor and Antiangiogenic Activity," Cancer Research, vol. 64, Jul. 15, 2004, XP008058944, pp. 4931-4941.
Office Action issued Nov. 9, 2011, in U.S. Appl. No. 11/997,543.
Office Action issued Jan. 12, 2012, in U.S. Appl. No. 13/205,328.
Okura et al., "Effects of Monoclonal Anti-c-Kit Antibody (ACK2) on Melanocytes in Newborn Mice," J. Invest Dermatol. (1995), vol. 105, pp. 322-328.
"Clinical Trial: AMG 706 200402373 Thyroid Cancer Study," Stage 4 Cancer Treatments, Chat w/a Cancer Info Expert About Stage 4 Cancer Treatment Options. www.CancerCenter.com (Jul. 2005).
First Office Action issued Nov. 30, 2012, in Chinese Patent Application No. 201080030508.6, with English translation.
Office Action issued Jan. 3, 2013, in U.S. Appl. No. 13/083,338.
Polverino et al., "AMG 706, an Oral, Multikinase Inhibitor that Selectively Targets Vascular Endothelial Growth Factor, Platelet-Derived Growth Factor, and Kit Receptors . . . ," Cancer Res. (2006), vol. 66, No. 17, pp. 8715-8721.
Reply filed Jan. 2, 2013, in response to the Communication Pursuant to Rules 70(2) and 70a(2) EPC issued Jul. 3, 2012, in European Patent Application No. 08704376.6.
Reply filed Jan. 3, 2013, in response to the Communication Pursuant to Rules 70(2) and 70a(2) EPC issued Jul. 5, 2012, in European Patent Application No. 08846814.5.
Notice of Allowance issued Jan. 18, 2013, in U.S. Appl. No. 12/524,754.

(56) References Cited

OTHER PUBLICATIONS

Notice of Non-Substantive Deficiencies Prior to Allowance issued Jan. 2, 2013, in Israeli Patent Application No. 175363, with English translation.
Notification of Defects issued Dec. 20, 2012, in Israeli Patent Application No. 205512, with English translation.
Response filed Dec. 20, 2012, in reply to the Invitation issued Nov. 30, 2012, in European Patent Application No. 03791389.4.
Argument Brief and Amendment filed Nov. 24, 2011, in reply to the Office Action issued Sep. 28, 2011, in Korean Patent Application No. 2007-7001347, with English translation.
Ko, "Stomach Cancer," Cancersupportivecare.com, published online Feb. 2003, pp. 1-4.
Office Action issued Dec. 19, 2011, in U.S. Appl. No. 12/524,754.
Communication Pursuant to Article 94(3) EPC issued Feb. 2, 2012, in European Patent Application No. 04818213.3.
Kitteringham et al., "A Simple Method for the Synthesis of Unsymmetrical Ureas," Synthetic Communications (2000), vol. 30, No. 11, pp. 1937-1943.
Amendment filed Jan. 16, 2013, in Korean Patent Application No. 10-2009-7017694, with English translation.
Decision of Patent Grant issued Jan. 22, 2013, in Japanese Patent Application No. P2008-516724, with English translation.
Notice of Reasons for Rejection issued Jan. 22, 2013, in Japanese Patent Application No. P2008-556208, with English translation.
Reply filed Jan. 26, 2013, in response to the Non-Final Office Action issued Sep. 25, 2012, in U.S. Appl. No. 13/322,961.
Amendment filed Jan. 30, 2013, in response to the Examiner's Letter issued Oct. 15, 2012, in New Zealand Patent Application No. 598291.
English translation of Notice of Non-Substantive Deficiencies Prior to Allowance of Patent Application issued Jan. 2, 2013, in Israeli Patent Application No. 175363.
Observations filed Feb. 7, 2013, in response to the First Office Action issed Nov. 30, 2012, in Chinese Office Action No. 201080030506.6, with English translation.
Juurikivi et al., "Inhibition of c-kit tyrosine kinase by imatinib mesylate induces apoptosis in mast cells in rheumatoid synovia . . . ," Ann Rheum Dis 2005, vol. 64, pp. 1126-1131.
Notice of Allowance issued Dec. 7, 2010, in Japanese Patent Application No. 2005-516605.
Office Action issued Jan. 7, 2011, in U.S. Appl. No. 12/092,539.
Supplementary European Search Report issued Nov. 24, 2010, in European Patent Application No. 06833681.7.
Vippagunta et al., "Crystalline solids," Advanced Drug Delivery Reviews 2001, vol. 48, pp. 3-26.
Yamada et al., "New Technique for Staining", Monthly Medical Technology Supplementary Volume, Apr. 1999.
Notice of Acceptance issued Feb. 27, 2013, in Australian Patent Application No. 2008325608.
Reply filed Feb. 27, 2013, in response to the Office Action issued Jan. 2, 2013, in Israeli Patent Application No. 175363, with English translation.
Notice of Allowance issued Feb. 19, 2013, in U.S. Appl. No. 12/741,682.
Notice of Allowance issued Mar. 22, 2012, in U.S. Appl. No. 12/986,638.
Notification on Defects issued Jan. 6, 2013, in Israeli Patent Application No. 207089, with English translation.
Response filed Mar. 14, 2013, in reply to the Office Action issued Dec. 20, 2012, in Israeli Patent Application No. 205512, with English translation.
Amendment with the English translation filed on Jan. 11, 2010, for Chinese Application No. 200580026468.7.
Amendment with the English translation filed on Sep. 23, 2009, for Chinese Application No. 200580026468.7.
Australian Notice of Allowance dated Apr. 29, 2010, for Application No. 2005283422.
Canadian Notice of Allowance dated Oct. 17, 2011, for Application No. 2579810.
Canadian Office Action dated Jul. 15, 2011, for Application No. 2579810.
Chinese Notice of Allowance with the English translation dated Feb. 5, 2010, for Application No. 200580026468.7.
Chinese Office Action with the English translation dated Jun. 26, 2009, for Application No. 200580026468.7.
Chinese Office Action with the English translation dated Nov. 20, 2009, for Application No. 200580026468.7.
Communication pursuant to Article 94(3) EPC dated Feb. 7, 2008, for European Application No. 05783232.1.
Communication regarding the expiry of opposition period dated Feb. 19, 2010, for European Application No. 05783232.1.
Communication under Rule 71(3) EPC dated Nov. 20, 2011, for Application No. 05783232.1.
Decision to grant a European patent dated Mar. 19, 2009, for European Application No. 05783232.1.
Extended European Search Report dated Sep. 7, 2007, for Application No. 05783232.1.
Invitation to declare maintenance of application dated Sep. 25, 2007, for European Application No. 05783232.1.
Isaraeli Office Action with the English translation dated Dec. 20, 2010, for Application No. 181697.
Israeli Notice of Allowance with the English translation dated Nov. 14, 2011, for Application No. 181697.
Japanese Notice of Allowance with the English translation dated Sep. 20, 2011, for Application No. 2006-535174.
Maintainance of the application dated Nov. 9, 2007, for European Application No. 05783232.1.
Notice Prior to Examination with the English translation dated Mar. 9, 2009, for Israeli Application No. 181697.
Reply to official communication dated Apr. 30, 2008, for European Application No. 05783232.1.
Response filed on Sep. 21, 2011, for Canadian Application No. 2579810.
Response to Notice Prior to Examination with the English translation dated Apr. 22, 2009, for Israeli Application No. 181697.
Response with the English translation filed on Jan. 11, 2010, for Chinese Application No. 200580026468.7.
Response with the English translation filed on Jan. 26, 2011, for Israeli Application No. 181697.
Response with the English translation filed on Sep. 23, 2009, for Chinese Application No. 200580026468.7.
Voluntary Amendment filed Feb. 9, 2010, for Australian Application No. 2005283422.
Voluntary Amendment filed Jul. 6, 2010, for Australian Application No. 2005283422.
Amendment and Response to Office Action under 37 C.F.R. § 1.111 dated Apr. 2, 2013 for U.S. Appl. No. 13/083,338, 9 pages.
Kawano et al., "Presentation Abstract, Abstract No. 1619, Combination of VEGFR inhibitor lenvatinib (E7080) and Met/EphB4 inhibitor golvatinib (E7050) overcomes VEGFR inhibitor-resistant tumor vascular", Annual Meeting 2013, Walter E. Washington Convention Center, Washington, D.C., Apr. 6-10, 2013, 1 page.
Notice of Allowance dated Feb. 15, 2013 for NZ App. Ser. No. 598291, 1 page.
Notice of Allowance dated Mar. 8, 2013 for CA App. Ser. No. 2627598, 1 page.
Office Action dated Mar. 29, 2013 for U.S. Appl. No. 13/624,278, 73 pages.
Submission Document Before the Patent Office re Observation dated Feb. 16, 2013 for CN App. Ser. No. 200980103218.7, 8 pages (with English translation).
Third Office Action dated Feb. 25, 2013 for CN App. Ser. No. 200880115011.7, 6 pages (with English translation).
Australian Examiner's first report dated Apr. 11, 2012 for Australian Application No. 2008205847.
Australian Examiner's first report dated Apr. 3, 2012 for Australian Application No. 2008211952.
Australian Office Action response dated Mar. 28, 2012 for Australian Application No. 2006309551.
Chinese First Office Action dated Feb. 20, 2012 for Chinese Application No. 200880115011.7 with English translation.

(56) References Cited

OTHER PUBLICATIONS

Chinese Second Office Action dated Mar. 7, 2012 for Chinese Application No. 200780017371.9 with English translation.
Chinese Second Office Action dated Mar. 7, 2012 for Chinese Application No. 200880002425.9 with English translation.
Hungarian Voluntary Amendment dated Sep. 10, 2010 for Hungarian Application No. P0302603/8 with English translation.
Israeli Notification of Defects dated Feb. 5, 2012 for Israeli Application No. 195282 with English translation.
Israeli Reply to Request according to section 18 dated Mar. 11, 2012 for Israeli Application No. 205512 with English translation.
Israeli Reply to Request according to section 18 dated Mar. 11, 2012 for Israeli Application No. 207089 with English translation.
Russian Office Action dated Jun. 29, 2004 for Russian Application No. 2003114740/04.
Taiwanese Amendment dated Apr. 17, 2002 for Taiwanese Patent Application No. 090125928 with English translation.
Taiwanese Application for Re-examination on Patent dated May 25, 2004 for Taiwanese Application No. 090125928 with English translation.
Taiwanese Application for Supplement and Amendment to Patent dated Dec. 11, 2007 for Taiwanese Application No. 090125928 with English translation.
Taiwanese Approval Decision Letter dated Oct. 20, 2008 for Taiwanese Application No. 090125928 with English translation.
Taiwanese Decision dated Apr. 26, 2004 for Taiwanese Application No. 090125928 with English translation.
Taiwanese Office Action of the Ipo dated Oct. 11, 2007 for Taiwanese Application No. 090125928 with English translation.
US Advisory Action dated Jun. 28, 2011 for U.S. Appl. No. 12/092,539.
US After-Final Amendment and Response to Office Action Under 37 C.F.R. § 1.116 dated Dec. 5, 2011 for U.S. Appl. No. 12/864,817.
US Amendment and Response to Final Office Action Under 37 C.F.R. § 1.116 dated Jun. 15, 2011 for U.S. Appl. No. 12/092,539.
US Amendment and Response to Non-Final Office Action dated Aug. 19, 2011 for U.S. Appl. No. 11/997,543.
US Amendment and Response to Non-Final Office Action under 37 C.F.R. § 1.111 dated Mar. 11, 2011 for U.S. Appl. No. 12/092,539.
US Amendment and Response to Office Action Under 37 C.F.R. § 1.111 dated Apr. 11, 2012 for U.S. Appl. No. 13/205,328.
US Amendment and Response to Office Action Under 37 C.F.R. § 1.111 dated Dec. 23, 2010 for U.S. Appl. No. 11/997,719.
US Amendment and Response to Office Action Under 37 C.F.R. § 1.111 dated Feb. 7, 2012 for U.S. Appl. No. 12/439,339.
US Notice of Allowance dated Feb. 27, 2009 for U.S. Appl. No. 11/293,785.
US Notice of Allowance dated Jun. 13, 2006 for U.S. Appl. No. 10/420,466.
US Notice of Allowance dated Jun. 3, 2008 for U.S. Appl. No. 11/293,785.
US Notice of Allowance dated Mar. 16, 2007 for U.S. Appl. No. 10/420,466.
US Notice of Allowance dated May 18, 2009 for U.S. Appl. No. 11/293,785.
US Notice of Allowance dated Nov. 19, 2008 for U.S. Appl. No. 11/293,785.
US Notice of Allowance dated Sep. 12, 2005 for U.S. Appl. No. 10/420,466.
US Office Action dated Apr. 13, 2005 for U.S. Appl. No. 10/420,466.
US Office Action dated Apr. 6, 2011 for U.S. Appl. No. 11/997,719.
US Office Action dated Dec. 16, 2011 for U.S. Appl. No. 12/864,817.
US Office Action dated Mar. 30, 2012 for U.S. Appl. No. 12/439,339.
US Office Action dated May 9, 2011 for U.S. Appl. No. 12/092,539.
US Office Action dated Nov. 3, 2011 for U.S. Appl. No. 12/864,817.
US Office Action dated Sep. 13, 2004 for U.S. Appl. No. 10/420,466.
US Office Action dated Sep. 4, 2007 for U.S. Appl. No. 11/293,785.
US Preliminary Amendment and Response to Restriction Requirement dated Aug. 10, 2011 for U.S. Appl. No. 12/439,339.
US Preliminary Amendment dated Apr. 18, 2003 for U.S. Appl. No. 10/420,466.
US Preliminary Amendment dated Dec. 2, 2005 for U.S. Appl. No. 10/420,466.
US Preliminary Amendment dated Oct. 27, 2003 for U.S. Appl. No. 10/420,517.
US Preliminary Amendment under 37 C.F.R. § 1.115 dated Feb. 3, 2006 for U.S. Appl. No. 11/293,785.
US Request for Continued Examination (RCE) Transmittal and Amendment and Response to Office Action Under 37 C.F.R. § 1.116 dated Jan. 9, 2012 for U.S. Appl. No. 11/997,543.
US Request for Continued Examination (RCE) Transmittal dated Dec. 22, 2011 for U.S. Appl. No. 12/864,817.
US Response to Notice of Non-Compliant Amendment dated Jan. 18, 2005 for U.S. Appl. No. 10/420,466.
US Response to Office Action dated Feb. 26, 2008 for U.S. Appl. No. 11/293,785.
US Response to Office Action dated Jul. 1, 2005 for U.S. Appl. No. 10/420,466.
US Response to Office Action Under 37 C.F.R. § 1.111 dated Aug. 9, 2011 for U.S. Appl. No. 12/864,817.
US Response to Office Action Under 37 C.F.R. § 1.111 dated Dec. 7, 2011 for U.S. Appl. No. 12/523,495.
US Response to Office Action Under 37 C.F.R. § 1.111 dated Feb. 17, 2012 for U.S. Appl. No. 12/524,754.
US Response to Office Action Under 37 C.F.R. § 1.116 dated Jul. 6, 2011 for U.S. Appl. No. 11/997,719.
US Response to Restriction Requirement dated Dec. 1, 2011 for U.S. Appl. No. 12/524,754.
US Response to Restriction Requirement dated Mar. 22, 2011 for U.S. Appl. No. 11/997,543.
US Response to Restriction Requirement dated Nov. 23, 2010 for U.S. Appl. No. 12/301,353.
US Response to Restriction Requirement dated Oct. 8, 2004 for U.S. Appl. No. 10/420,466.
US Restriction Requirement dated Feb. 23, 2011 for U.S. Appl. No. 11/997,543.
US Restriction Requirement dated Jul. 29, 2011 for U.S. Appl. No. 12/439,339.
US Restriction Requirement dated Nov. 3, 2011 for U.S. Appl. No. 12/524,754.
US Restriction Requirement dated Oct. 29, 2010 for U.S. Appl. No. 12/092,539.
US Restriction Requirement dated Oct. 29, 2010 for U.S. Appl. No. 12/301,353.
US Second Preliminary Amendment and Response to Restriction Requirement dated Nov. 22, 2010 for U.S. Appl. No. 12/092,539.
Extended European Search Report dated Jan. 19, 2011, issued in European Patent Application No. 07806561.2.
Office Action dated Apr. 11, 2012, issued in Russian Patent Applciation No. 2012103471, with English translation.
Hearing Notice issued May 4, 2012, in India Patent Application No. 383/CHENP/2008.
Notice of Final Rejection issued Apr. 27, 2012, in Korean Patent Application No. 10-2007-7001347, with English translation.
Office Action issued Apr. 12, 2012, in U.S. Appl. No. 13/083,338.
Examination Report issued May 9, 2012, in Pakistan Application No. 94/2011.
Request for Amendment of Patent filed Feb. 17, 2012, in Thailand Patent Application No. 1201000221, with English translation.
Di Raimondo et al., "Antiogenic factors in multiple myeloma: higher levels in bone marrow than in peripheral blood," Haematologica, 2000, vol. 85, pp. 800-805.
Ocqueteau et al., "Expression of the CD117 antigen (C-Kit) on normal and myelomatous plasma cells," British Journal of Haematology, 1996, vol. 95, pp. 489-493.
Office Action issued Mar. 24, 2011, in U.S. Appl. No. 12/094,492.
Notice of Reasons for Rejection issued Jun. 5, 2012, in Japanese Patent Application No. P2009-123432, with English translation.
Response dated May 29, 2012, filed in response to the Official Action dated Apr. 11, 2012, issued in Russian Patent Application No. 2012103471, with English translation.

(56) References Cited

OTHER PUBLICATIONS

Amendment after Allowance for CA Patent Application No. 2,426,461 dated Jan. 4, 2011.
Amendment description filed after receipt of search report for EP Patent Application No. 10809938.3 dated Dec. 8, 2011.
Amendment for CN Patent Application No. 01819710.8 dated Apr. 11, 2006 with English translation.
Amendment for CN Patent Application No. 01819710.8 dated May 28, 2003 with English translation.
Amendment for CN Patent Application No. 01819710.8 dated Oct. 9, 2006 with English translation.
Amendment for CN Patent Application No. 01819710.8 dated Sep. 13, 2005 with English translation.
Amendment for CN Patent Application No. 200710007097.9 dated Jan. 26, 2010 with English translation.
Amendment for CN Patent Application No. 200710007097.9 dated Jul. 2, 2009 with English translation.
Amendment for CN Patent Application No. 200710007097.9 dated Jun. 22, 2010 with English translation.
Amendment for CN Patent Application No. 200710007097.9 dated Nov. 19, 2009 with English translation.
Amendment for JO Patent Application No. 55/2011 dated Dec. 12, 2011 with English translation.
Amendment for JP Patent Application No. 2002-536056 dated Apr. 19, 2005 with English translation.
Amendment for JP Patent Application No. 2002-536056 dated Mar. 7, 2005 with English translation.
Amendment for JP Patent Application No. 2005-124034 dated May 21, 2009 with English translation.
Amendment for JP Patent Application No. 2005-124034 Mar. 23, 2009 with English translation.
Amendment for KR Patent Application No. 10-2003-7005506 dated Mar. 6, 2006 with English translation.
Amendment for KR Patent Application No. 10-2003-7005506 dated Oct. 25, 2005 with English translation.
Amendment for KR Patent Application No. 10-2005-7020292 dated Mar. 8, 2006 with English translation.
Amendment for LB Patent Application No. 9292 dated Oct. 28, 2011.
Amendment for TW Patent Application No. 100104281 dated Feb. 9, 2011.
Amendment for TW Patent Application No. 90125928 dated Apr. 17, 2002 with English translation.
Amendment for VN Patent Application No. 1-2011-03484 dated Dec. 15, 2011 with English translation.
Amendment for ZA Patent Application No. 2003/3567 dated Aug. 17, 2004.
Amendment for ZA Patent Application No. 2003/3567 dated Aug. 4, 2004.
Amendment for ZA Patent Application No. 2011/08697 dated Dec. 22, 2011.
Amendments received before examination for EP Patent Application No. 01976786.2 dated Sep. 10, 2004.
Approval of request for amendments for EP Patent Application No. 04025700.8 dated Mar. 13, 2008.
Argument Brief for KR Patent Application No. 10-2003-7005506 dated dated Mar. 6, 2006 with English translation.
Argument Brief for KR Patent Application No. 10-2003-7005506 dated dated Oct. 25, 2005 with English translation.
Argument Brief for KR Patent Application No. 10-2005-7020292 dated Mar. 8, 2006 with English translation.
Argument for JP Patent Application No. 2002-536056 dated Apr. 19, 2005 with English translation.
Argument for JP Patent Application No. 2005-124034 dated Mar. 23, 2009 with English translation.
Argument for JP Patent Application No. 2005-124034 dated May 21, 2009 with English translation.
Brief communication to applicant for EP Patent Application No. 01976786.2 dated Sep. 9, 2005.
Canadian Office Action for CA Patent Application No. 2,426,461 dated Feb. 10, 2010.
Canadian Office Action for CA Patent Application No. 2,426,461 dated May 8, 2009.
Canadian Office Action for CA Patent Application No. 2,426,461 dated Nov. 20, 2008.
Canadian Office Action for CA Patent Application No. 2,426,461 dated Dec. 6, 2007.
Chinese Office Action for CN Patent Application No. 01819710.8 dated Aug. 11, 2006 with English translation.
Chinese Office Action for CN Patent Application No. 01819710.8 dated Feb. 10, 2006 with English translation.
Chinese Office Action for CN Patent Application No. 01819710.8 dated May 13, 2005 with English translation.
Chinese Office Action for CN Patent Application No. 200710007096.4 dated Jul. 24, 2009 with English translation.
Chinese Office Action for CN Patent Application No. 200710007097.9 dated Apr. 27, 2010 with English translation.
Chinese Office Action for CN Patent Application No. 200710007097.9 dated Dec. 25, 2009 with English translation.
Chinese Office Action for CN Patent Application No. 200710007097.9 dated Mar. 6, 2009.
Chinese Office Action for CN Patent Application No. 200710007097.9 dated Sep. 11, 2009 with English translation.
Communication about intention to grant a European Patent for EP Patent Application No. 01976786.2 dated Sep. 4, 2006.
Communication about intention to grant a European patent for EP Patent Application No. 04025700.8 dated Oct. 15, 2007.
Communication about intention to grant a European patent for EP Patent Application No. 06023078.6 dated Jul. 18, 2008.
Communication from Examining Division for EP Patent Application No. 06023078.6 dated Aug. 2, 2007.
Communication from the Examining Division for EP Patent Application No. 01976786.2 dated Sep. 19, 2005.
Communication from the Examining Division for EP Patent Application No. 01976786.2 dated Aug. 17, 2005.
Communication from the Examining Division for EP Patent Application No. 01976786.2 dated Mar. 21, 2006.
Communication from the Examining Division for EP Patent Application No. 04025700.8 dated Apr. 10, 2006.
Communication from the Examining Division for EP Patent Application No. 04025700.8 dated Oct. 23, 2006.
Communication from the Examining Division for EP Patent Application No. 06023078.6 dated Sep. 26, 2007.
Communication regarding the expiry of opposition period for EP Patent Application No. 01976786.2 dated Jan. 4, 2008.
Communication regarding the expiry of opposition period for EP Patent Application No. 04025700.8 dated May 7, 2009.
Communication regarding the expiry of opposition period for EP Patent Application No. 06023078.6 dated Nov. 4, 2009.
Decision to grant a European patent for EP Patent Application No. 01976786.2 dated Feb. 1, 2007.
Decision to grant a European patent for EP Patent Application No. 04025700.8 dated Jun. 5, 2008.
Decision to grant a European patent for EP Patent Application No. 06023078.6 dated Dec. 4, 2008.
Deficiencies in sequence listing for EP Patent Application No. 06023078.6 dated Dec. 5, 2006.
European Maintenance of the application for EP Patent Application No. 06023078.6 dated Jun. 19, 2007.
European Search Report for EP Patent Application No. 04025700.8 dated Jan. 13, 2005.
European Search Report for EP Patent Application No. 06023078.6 dated Mar. 16, 2007.
Examination Report for NZ Patent Application No. 525324 dated Sep. 2, 2004.
Examiner's Report for AU Patent Application No. 2001295986 dated May 4, 2006.
Examiner's Report for AU Patent Application No. 2001295986 dated Sep. 20, 2005.
Examiner's Report for AU Patent Application No. 2006203099 dated Feb. 21, 2008.
Examiner's Report for AU Patent Application No. 2006236039 dated Mar. 26, 2008.

(56) References Cited

OTHER PUBLICATIONS

Filipino Office Action for PH Patent Application No. 1-2003-500266 dated Aug. 8, 2003.
Filipino Office Action for PH Patent Application No. 1-2003-500266 dated Jul. 21, 2006.
Filipino Office Action for PH Patent Application No. 1-2003-500266 dated Jun. 27, 2007.
Filipino Office Action for PH Patent Application No. 1-2003-500266 dated Mar. 21, 2007.
Filipino Office Action for PH Patent Application No. 1-2003-500266 dated Sep. 7, 2007.
Formality Requirement for PH Patent Application No. 1-2003-500266 dated Jun. 18, 2003.
Information about decision on request for EP Patent Application No. 06023078.6 dated Mar. 21, 2007.
International Preliminary Examination Report for International Patent Application No. PCT/JP01/09221 dated Jan. 8, 2003.
International Preliminary Report of Patentability for International Patent Application No. PCT/JP2010/063804 dated Mar. 13, 2012.
International Search Report for International Patent Application No. PCT/JP01/09221 dated Jan. 15, 2002 with English translation.
International Search Report for International Patent Application No. PCT/JP2010/063804 dated Sep. 14, 2010 with English translation.
Invitation to declare maintenance of the application for EP Patent Application No. 01976786.2 date Jul. 12, 2004.
Invitation to declare maintenance of the application for EP Patent Application No. 06023078.6 dated May 2, 2007.
Israeli Notice of Defects in IL Patent Application No. 189677 dated Feb. 18, 2009 with English translation.
Israeli Notice of Deficiencies in IL Patent Application No. 155447 dated Oct. 16, 2007 with English translation.
Israeli Notice Prior to Allowance in IL Patent Application No. 189677 dated Mar. 14, 2010 with English translation.
Israeli Notice Prior to Allowance in Patent Application No. 155447 dated Dec. 26, 2007 with English translation.
Israeli Notice Prior to Examination in IL Patent Application No. 189677 dated Jun. 29, 2008 with English translation.
Israeli Response to Notice of Defects in IL Patent Application No. 189677 dated May 13, 2009 with English translation.
Japanese Office Action for JP Patent Application No. 2002-536056 dated Apr. 11, 2005 with English translation.
Japanese Office Action for JP Patent Application No. 2005-124034 dated Apr. 28, 2009 with English translation.
Japanese Office Action for JP Patent Application No. 2005-124034 dated Jan. 27, 2009 with English translation.
Korean Office Action for KR Patent Application 10-2005-7020292 dated Dec. 8, 2005 with English translation.
Korean Office Action for KR Patent Application No. 10-2003-7005506 dated Jan. 5, 2006 with English translation.
Korean Office Action for KR Patent Application No. 10-2003-7005506 dated Jul. 27, 2005 with English translation.
Maintenance of the application for EP Patent Application No. 01976786.2 dated Sep. 6, 2004.
Mexican Notice of Allowance for MX Patent Application No. PA/a/2003/003362 dated Oct. 18, 2006 with English translation.
Mexican Office Action for MX Patent Application No. PA/a/2003/003362 dated Jun. 7, 2006 with English translation.
Mexican Office Action for MX Patent Application No. PA/a/2003/003362 dated Oct. 4, 2005 with English translation.
Mexican Office Action for MX Patent Application No. PA/a/2005/013764 dated Nov. 26, 2007 with English translation.
Mexican Response for MX Patent Application No. PA/a/2003/003362 dated Aug. 21, 2006 with English translation.
Mexican Response for MX Patent Application No. PA/a/2003/003362 dated Dec. 15, 2005 with English translation.
New Zealand Examination Report for NZ Patent Application No. 525324 dated Feb. 18, 2005.
New Zealand Examination Report for NZ Patent Application No. 525324 dated Oct. 13, 2003.
New Zealand Notice of Acceptance of Complete Specification for NZ Patent Application No. 525324 dated Mar. 4, 2005.
New Zealand Response to Office Action for NZ Patent Application No. 525324 dated Aug. 26, 2004.
New Zealand Response to Office Action for NZ Patent Application No. 525324 dated Jan. 21, 2005.
Norwegian Notice of Allowance for NO Patent Application No. 20031731 dated Oct. 31, 2008 with English translation.
Norwegian Office Action for NO Patent Application No. 20031731 dated Mar. 7, 2007 with English translation.
Norwegian Office Action for NO Patent Application No. 20031731 dated May 16, 2008 with English translation.
Norwegian Office Action for NO Patent Application No. 20031731 dated Oct. 4, 2007 with English translation.
Norwegian Office Action for NO Patent Application No. 20031731 dated Sep. 5, 2008 with English translation.
Norwegian Response to Office Action for NO Patent Application No. 20031731 dated Aug. 18, 2008 with English translation.
Norwegian Response to Office Action for NO Patent Application No. 20031731 dated May 7, 2008 with English translation.
Notice of Acceptance for AU Patent Application No. 2001295986 dated Aug. 3, 2006.
Notice of Acceptance for AU Patent Application No. 2006236039 dated May 13, 2008.
Notice of Acceptance for ZA Patent Application No. 2003/3567 dated Aug. 10, 2004.
Notice of Allowability for PH Patent Application No. 1-2003-500266 dated Nov. 28, 2007.
Notice of Allowance for CA Patent Application No. 2,426,461 dated Oct. 14, 2010.
Notice of Allowance for CN Patent Application No. 01819710.8 dated Dec. 15, 2006 with English translation.
Notice of Allowance for CN Patent Application No. 200710007097.9 dated Oct. 9, 2010 with English translation.
Notice of Allowance for JP Patent Application No. 2002-536056 dated Aug. 2, 2005 with English translation.
Notice of Allowance for JP Patent Application No. 2005-124034 dated Jul. 21, 2009 with English translation.
Notice of decision for patent for KR Patent Application No. 10-2003-7005506 dated Jun. 12, 2006 with English translation.
Notice of decision to grant a patent for KR Patent Application 10-2005-7020292 dated Apr. 17, 2006 with English translation.
Notice of Issuance of Letters Patent for PH Patent Application No. 1-2003-500266 dated Feb. 24, 2009.
Notification for PH Patent Application No. 1-2003-500266 dated Apr. 25, 2008.
Office Letter Confirmantion of Amendment After Allowance for CA Patent Application No. 2,426,461 dated Jan. 11, 2011.
Preliminary Amendment for KR Patent Application No. 10-2003-7005506 dated May 23, 2003 with English translation.
Preliminary Amendment for U.S. Appl. No. 10/420,466 dated Apr. 18, 2003.
Preliminary Amendment for U.S. Appl. No. 10/420,517 dated Oct. 27, 2003.
Re-examination for TW Patent Application No. 090125928 dated Nov. 25, 2004 with English translation.
Rejection for TW Patent Application No. 090125928 dated Apr. 26, 2004 with English translation.
Reply to communication from the Examining Division for EP Patent Application No. 01976786.2 dated Jul. 19, 2006.
Reply to communication from the Examining Division for EP Patent Application No. 01976786.2 dated Jan. 25, 2006.
Reply to communication from the Examining Division for EP Patent Application No. 04025700.8 dated Feb. 15, 2007.
Reply to communication from the Examining Division for EP Patent Application No. 04025700.8 dated Jan. 26, 2007.
Reply to communication from the Examining Division for EP Patent Application No. 04025700.8 dated Sep. 12, 2006.
Reply to communication from the Examining Division for EP Patent Application No. 06023078.6 dated Feb. 4, 2008.
Reply to communication from the Examining Division for EP Patent Application No. 06023078.6 dated Sep. 10, 2007.

(56) References Cited

OTHER PUBLICATIONS

Reply to the invitation to remedy deficiencies for EP Patent Application No. 06023078.6 dated Jan. 11, 2007.
Request for amendment of the text intended for grant and translation of claims for EP Patent Application No. 04025700.8 dated Feb. 1, 2008.
Request for amendment of the text intended for grant and translation of claims for EP Patent Application No. 06023078.6 dated Nov. 5, 2008.
Request for correction of errors in filed documents for EP Patent Application No. 06023078.6 dated Feb. 13, 2007.
Response to to Israeli Notice of Deficiencies for IL Patent Application No. 155447 dated Dec. 4, 2007 with English translation.
Response to Israeli Notice Prior to Examination for IL Patent Application No. 189677 dated Jan. 11, 2009 with English translation.
Response to Non-Compliant Amendment for U.S. Appl. No. 10/420,466 dated Jan. 13, 2005.
Response to Office Action for AU Patent Application No. 2001295986 dated Apr. 27, 2006.
Response to Office Action for AU Patent Application No. 2001295986 dated Jul. 26, 2006.
Response to Office Action for AU Patent Application No. 2006236039 dated May 8, 2008.
Response to Office Action for CA Patent Application No. 2,426,461 dated Aug. 13, 2009.
Response to Office Action for CA Patent Application No. 2,426,461 dated Feb. 23, 2009.
Response to Office Action for CA Patent Application No. 2,426,461 dated May 16, 2008.
Response to Office Action for CA Patent Application No. 2,426,461 dated May 20, 2010.
Response to Office Action for CN Patent Application No. 01819710.8 dated Apr. 11, 2006 with English translation.
Response to Office Action for CN Patent Application No. 01819710.8 dated Oct. 9, 2006 with English translation.
Response to Office Action for CN Patent Application No. 01819710.8 dated Sep. 13, 2005 with English translation.
Response to Office Action for CN Patent Application No. 200710007097.9 dated Jan. 26, 2010 with English translation.
Response to Office Action for CN Patent Application No. 200710007097.9 dated Jul. 2, 2009 with English translation.
Response to Office Action for CN Patent Application No. 200710007097.9 dated Jun. 22, 2010 with English translation.
Response to Office Action for CN Patent Application No. 200710007097.9 dated Nov. 19, 2009 with English translation.
Response to Office Action for NO Patent Application No. 20031731 dated Aug. 18, 2008 with English translation.
Response to Office Action for NO Patent Application No. 20031731 dated Oct. 13, 2008 with English translation.
Response to Office Action for NO Patent Application No. 20031731 dated Sep. 10, 2007 with English translation.
Response to Office Action for PH Patent Application No. 1-2003-500266 Apr. 30, 2008.
Response to Office Action for PH Patent Application No. 1-2003-500266 dated Apr. 17, 2007.
Response to Office Action for PH Patent Application No. 1-2003-500266 dated Aug. 14, 2006.
Response to Office Action for PH Patent Application No. 1-2003-500266 dated Aug. 5, 2003.
Response to Office Action for PH Patent Application No. 1-2003-500266 dated Jul. 31, 2007.
Response to Office Action for PH Patent Application No. 1-2003-500266 dated Oct. 15, 2007.
Response to Office Action for PH Patent Application No. 1-2003-500266 dated Sep. 15, 2003.
Response to Office Action for PH Patent Application No. 1-2003-500266 dated Sep. 8, 2003.
Response to Office Action for RU Patent Application No. 2003114740 dated Mar. 17, 2005 with English translation.
Response to Office Action for RU Patent Application No. 2003114740 dated Nov. 30, 2004 with English translation.
Response to Office Action for TW Patent Application No. 090125928 dated Dec. 11, 2007 with English translation.
Response to Office Action for U.S. Appl. No. 10/420,466 dated Jun. 29, 2005.
Response to Office Action for U.S. Appl. No. 10/420,466 dated Oct. 8, 2004.
Response to Office Action for U.S. Appl. No. 11/293,785 dated Feb. 26, 2008.
Response to the Notice of Allowability for PH Patent Application No. 1-2003-500266 dated Dec. 13, 2007.
Russian Notice of Allowance for RU Patent Application No. 2003114740 dated Apr. 19, 2005 with English translation.
Russian Office Action for RU Patent Application No. 2003114740 dated Jan. 19, 2005 with English translation.
Russian Office Action for RU Patent Application No. 2003114740 dated Jun. 29, 2004 with English translation.
Russian Response to Office Action for RU Application No. 2012103471/20 dated May 29, 2012 with English translation.
Supplementary Partial European Search Report for EP Patent Application No. 01976786.2 dated Apr. 6, 2004.
Supplementary Partial European Search Report for EP Patent Application No. 01976786.2 dated Jul. 6, 2004.
Taiwanese Notice of Allowance for TW Patent Application No. 090125928 dated Oct. 20, 2008 with English translation.
Taiwanese Office Action for TW Patent Application No. 90125928 dated Oct. 11, 2007 with English translation.
US Notice of Allowance for U.S. Appl. No. 10/420,466 dated Jun. 13, 2006.
US Notice of Allowance for U.S. Appl. No. 10/420,466 dated Mar. 16, 2007.
US Notice of Allowance for U.S. Appl. No. 10/420,466 dated Sep. 12, 2005.
US Notice of Allowance for U.S. Appl. No. 11/293,785 dated Feb. 27, 2009.
US Notice of Allowance for U.S. Appl. No. 11/293,785 dated May 18, 2009.
US Notice of Allowance for U.S. Appl. No. 11/293,785 dated Nov. 19, 2008.
US Notice of Allowance for U.S. Appl. No. 11/293,785 due Jun. 3, 2008.
US Office Action for U.S. Appl. No. 10/420,466 dated Apr. 13, 2005.
US Office Action for U.S. Appl. No. 10/420,466 dated Sep. 13, 2004.
US Office Action for U.S. Appl. No. 11/293,785 dated Sep. 4, 2007.
US Preliminary Amendment for U.S. Appl. No. 10/420,466 dated Dec. 2, 2005.
US Preliminary Amendment for U.S. Appl. No. 11/293,785 dated Feb. 3, 2006.
Voluntary Amendment for CA Patent Application No. 2,426,461dated Aug. 19, 2010.
Voluntary Amendment for AU Patent Application No. 2006203099 dated Aug. 30, 2006.
Voluntary Amendment for AU Patent Application No. 2006203099 dated Feb. 21, 2007.
Voluntary Amendment for AU Patent Application No. 2006236039 dated Feb. 27, 2007.
Voluntary Amendment for CN Patent Application No. 200710007097.9 dated Aug. 11, 2010 with English translation.
Voluntary Amendment for HU Patent Application No. P0302603 dated Sep. 10, 2010 with English translation.
Written Amendment for JP Patent Application No. 2009-123432 dated Jun. 16, 2009 with English translation.
Written Amendment for JP Patent Application No. 2011-527665 dated Sep. 21, 2011 with English translation.
Written Statement for JP Patent Application No. 2009-123432 dated Jun. 16, 2009 with English translation.
Written Statement for JP Patent Application No. 2011-527665 dated Sep. 21, 2011 with English translation.
Anonymous, "Scientific Discussion," EMEA, URL:http://www.ema.europa.eu/docs/en_GB/document_library/EPARScientific_Discussion/human/000406/WC500022203.pdf, 2004, pp. 1-61, XP007918143.

(56) References Cited

OTHER PUBLICATIONS

Bastin et al., "Salt Selection and Optimisation Procedures for Pharmaceutical New Chemical Entities," Organic Process Research & Development, vol. 4, No. 5, 2000, pp. 427-435, XP002228592.
Berge et al., "Pharmaceutical Salts," Journal of Pharmaceutical Sciences, vol. 66, No. 1, Jan. 1977, pp. 1-19, XP002550655.
European Office Action dated Apr. 18, 2011 for European Application No. 04807580.8.
Extended European Search Report dated May 23, 2011 for European Application No. 06767145.3.
Gould, "Salt Selection for Basic Drugs," International Journal of Pharmaceutics, vol. 33, 1986, pp. 201-217, XP025813036.
Morris et al., "An Integrated Approach to the Selection of Optimal Salt Form for a New Drug Candidate," International Journal of Pharmaceutics, vol. 105, 1994, pp. 209-217, XP023724810.
Yu, "Amorphous Pharmaceutical Solids: Preparation, Characterization and Stabilization," Advanced Drug Delivery Reviews, vol. 48, 2001, pp. 27-42, XP009065056.
First Examination Report issued Oct. 30, 2012, in Indian Patent Application No. 1571/CHENP/2007.
Indian Patent Application No. 2572/CHENP/2006 filed Jul. 13, 2006.
Patent Examination Report No. 1 issued Nov. 24, 2012, in Australian Patent Application No. 2008325608.
Office Action issued Dec. 27, 2011, in U.S. Appl. No. 12/523,495.
Office Action issued Sep. 28, 2011, in Korean Patent Application No. 10-2007-7001347, with English translation.
Amendment filed Dec. 23, 2012, in response to the Notification of Defects issued Oct. 15, 2012, in Israeli Patent Application. No. 260090, with English translation.
Extended European Search Report issued Jan. 2, 2013, in European Patent Application No. 10809938.3.
Acceptance of Complete Specification dated May 25, 2012, issued in South African Patent Application No. 2011/08697.
Office Action issued Jun. 8, 2012, in U.S. Appl. No. 13/083,338.
Request for Examination of Patentability dated Jun. 12, 2012, filed in Colombian patent Application No. 12 022608, with English translation.
Santoro et al., "Molecular Mechanisms of RET Activation in Human Cancer," Ann. N.Y. Acad. Sci. (2002) vol. 963, pp. 116-121.
Notification Related to the Application for Invention issued May 22, 2012, in Ukraine Patent Application No. a 2012 03132, with English translation.
Request for Voluntary Amendments filed May 10, 2012, in Ukraine Patent Application No. a 2012 03132, with English translation.
Search Report issued Jul. 7, 2011, in European Patent Application No. 03791389.4.
Notification of Defects issued Apr. 22, 2012, in Israel Patent Application No. 199907, with English translation.
Final Office Action issued May 1, 2012, in U.S. Appl. No. 13/205,328.
Notice of Allowance issued Apr. 24, 2012, in U.S. Appl. No. 12/524,754.
Office Action issued Apr. 30, 2012, in U.S. Appl. No. 12/741,682.
Preliminary Amendment and Response to Restriction Requirement filed Apr. 30, 2012, in U.S. Appl. No. 13/083,338.
Response filed Jul. 13, 2012, in Korean Patent Application No. 10-2009-7005657, with English translation.
Grant of Request for Correction of Specification issued Aug. 8, 2012, in Singapore Patent Application No. 201108602-2.
Database BIOSIS [Online] Biosciences Information Service, Philadelphia, PA, US: Aug. 2008, Koyama Noriyuki et al., "Anti-tumor effect of E7080, a novel angiogenesis inhibitor," XP002677323, Database Accession No. PREV200800475929, Abstract.
Notice of Allowance issued Aug. 7, 2012, in Japanese Patent Application No. 2007-529565, with English translation.
Supplementary European Search Report issued Jul. 5, 2012, in European Patent Application No. 08846814.5.
Office Action issued May 24, 2011, in Chinese Patent Application No. 200880003336.6, with English translation.
Office Action issued Nov. 3, 2011, in U.S. Appl. No. 12/864,817.
Search Report issued Sep. 9, 2011, in European Patent Application No. 10015141.4.
Zhou et al., "Research on Correlation Between VEGF Detection in Primary Stomach Cancer and Clinical Pathological Factors," Journal of Practical Oncology (Apr. 25, 2006) vol. 20, No. 2, pp. 103-105, with English translation.
Office Action issued May 19, 2011, in U.S. Appl. No. 12/864,817.
Decision of Final Rejection issued Sep. 5, 2012, in Chinese Patent Application No. 200880003336.6, with English translation.
Notice of Allowance issued Oct. 9, 2012, in U.S. Appl. No. 12/524,754.
Notice of Allowance issued Sep. 25, 2012, in U.S. Appl. No. 12/986,638.
Office Action issued Sep. 25, 2012, in U.S. Appl. No. 13/322,961.
Response filed Jul. 11, 2012, in reply to the Second Office Action issued May 3, 2012, in Chinese Patent Application No. 200880003336.6, with English translation.
Schlumberger et al., "A Phase 2 Trial of the Multi-targeted Kinase Inhibitor Lenvatinib(E7080) in Advanced Medullary Thyroid Cancer (MTC)," 2012 ASCO Annual Meeting, Poster Presentation, Jun. 1-5, 2012.
Second Office Action issued Sep. 5, 2012, in Chinese Patent Application No. 200880115011.7, with English translation.
Forbes et al., "Dissolution kinetics and solubilities of p-aminosalicylic acid its salts," International Journal of Pharmaceutics (1995) vol. 126, pp. 199-208.
Mutschler et al., Arzneimittel-wirkungen Lehrbuch der Pharmkologie und Toxikologie, Wissenschaftliche Verlagsgesellschaft, Stuttgart, Jan. 1, 1999, pp. 1-5, XP 007919509, with English translation.
Office Action issued Oct. 25, 2011, in European Patent Application No. 04 807 570.8.
Voigt et al., "Chapter 2.2 Loslichkeit, Losungsgeschwindigkeit, Loslichkeitsverbesserung," Pharmazeutische Technologie Fuer Studuim und Beruf, DT. Apotheker-Verl, Stuttgard; DE, Jan. 1, 2000, pp. 40-52, XP008143620, with English translation.
Amendment filed May 10, 2012, in Japanese Patent Application No. 2011-527665, with English translation.
Bemex et al., "Spatial and temporal patterns of c-kit-expressing cells in WlacZ/+ and WlacZ/WlacZ mouse embryos," Development (1996), vol. 122, pp. 3023-3033.
Explanation of Circumstances Concerning Accelerated Examination filed May 10, 2012, in Japanese Patent Application No. 2011-527665, with English translation.
Response filed Nov. 20, 2012, in reply to the Second Office Action issued in Chinese Patent Application No. 200880115011.7, with English translation.
Micke et al,. "Characterization of c-kit Expression in Small Cell Lung Cancer: Prognostic and Therapeutic Implications," Clinical Cancer Research (Jan. 2003) vol. 9, pp. 188-194.
Office Action issued Sep. 1, 2010, in U.S. Appl. No. 10/797,903.
Communication Pursuant to Article 94(3) EPC issued Oct. 10, 2012, in European Patent Application No. 07743994.1.
Examination Report issued Oct. 15, 2012, in New Zealand Patent Application No. 596291.
First Office Action issued Sep. 29, 2012, in Chinese Patent Application No. 200980103218.7, with English translation.
Wang et al., "Phase II study of gemcitabine and carboplatin in patients with advanced non-small-cell lung cancer," Cancer Chemother Pharmacol, vol. 60, pp. 601-607, 2007.
Werner et al., "Gastric Adenocarcinoma: Pathomorphology and Molecular Pathology", J. Cancer Res. Clin. Oncol., vol. 127, 2001, pp. 207-216.
Willett et al., "Direct Evidence that the VEGF-Specific Antibody Bevacizumab has Antivascular Effects in Human Rectal Cancer", Nature Medicine, vol. 10, No. 2, Feb. 2004, pp. 145-147.
Wozniak et al., "Randomized Trial Comparing Cisplatin With Cisplatin Plus Vinorelbine in the Treatment of Advanced Non-Small-Cell Lung Cancer: A Southwest Oncology Group Study," Journal of Clinical Oncology, vol. 16, No. 7, Jul. 1998, pp. 2459-2465.
Yamada et al., "New Technique for Staining", Monthly Medical Technology Supplementary Volume.

(56) References Cited

OTHER PUBLICATIONS

Yanagihara et al., "Development and biological analysis of peritoneal metastatis mouse models for human scirrhous stomach cancer," Cancer Science, vol. 96, No. 6, pp. 323-332, Jun. 2005.
Zhu et al., "Fibroblast Growth Factor Receptor 3 Inhibition by Short Hairpin RNAs Leads to Apoptosis in Multiple Myeloma", Molecular Cancer Therapeutics, vol. 4, No. 5, 2005, pp. 787-798.
Zieger et al., "Role of Activating Fibroblast Growth Factor Receptor 3 Mutations in the Development of Bladder Tumors", Clinical Cancer Research, vol. 11, No. 21, Nov. 1, 2005, pp. 7709-7719.
Office Action issued Nov. 14, 2011, in U.S. Appl. No. 12/439,339.
English translation of International Preliminary Report on Patentability and Written Opinion issued Jan. 24, 2013, in PCT International Application No. PCT/JP2011/064430.
Response filed Jan. 25, 2013, in reply to the Office Action issued Sep. 19, 2012, in Canadian Patent Application No. 2,627,598 (PCT).
Patent Examination Report 1 issued Jan. 30, 2013, in Australian Patent Application No. 2009210098.
Request to Amend a Complete Specification filed Feb. 15, 2013, in Australian Patent Application No. 2008325608.
Response filed Feb. 8, 2013, in reply to the Examination Report issued Oct. 19, 2012, in European Patent Application No. 07743994.1.
Response to Third Office Action filed Nov. 30, 2012, in Chinese Patent Application No. 200780017371.9, with English translation.
Office Action issued Feb. 23, 2011, in U.S. Appl. No. 11/997,543.
Zhang et al., "Overexpression of Platelet-Derived Growth Factor Receptor Alpha in Endothelial Cells of Hepatocellular Carcinoma Associated with High Metastatic Potential," Clin Cancer Res, vol. 11, No. 24, Dec. 15, 2005, pp. 8557-8563.
English translation of the International Preliminary Report on Patentability issued Mar. 22, 2012, in PCT International Patent Application No. PCT/JP2010/063804.
Office Action issued May 19, 2011, in U.S. Appl. No. 11/997,543.
Paz et al., "Development of angiogenesis inhibitors to vascular endothelial growth factor receptor 2. Current status and future perspective," Frontiers in Bioscience (May 1, 2005) vol. 10, pp. 1415-1439.
Pritzker, "Cancer Biomarkers: Easier Said Than Done," Clinical Chemistry (2002) vol. 48, No. 8, pp. 1147-1150.
Tong et al., "Vascular normalization by vascular endothelial growth factor receptor 2 blockade induces a pressure gradient across . . . ," Cancer Research (Jun. 1, 2004) vol. 64, pp. 3731-3736.
Zhu et al., "Inhibition of human leukemia in an animal model with human antibodies directed against vascular endothelial growth factor receptor 2 . . . ," Leukemia (2003) vol. 17, pp. 604-611.
Amendment and Response filed on Jul. 30, 2012, in response to the Non-Final Office Action dated Apr. 30, 2012 for U.S. Appl. No. 12/741,682.
Communication Under Rule 71(3) EPC issued Jun. 20, 2012, in European Patent Application No. 06782407.8.
Communication Under Rule 71(3) EPC issued Jun. 25, 2012, in European Application No. 07806561.2.
Decision of Patent Grant issued Jul. 17, 2012, in Japanese Application No. P2011-527665, with English translation.
Notice of Acceptance issued Jul. 10, 2012, in Australian Patent Application No. 2008211952.
Amendment and Response filed Jul. 30, 2012, in response to the Office Action issued Mar. 30, 2012, in U.S. Appl. No. 12/439,339.
Rejection Decision issued Aug. 3, 2012, in Chinese Patent Application No. 200680020317.5, with English translation.
De Lange et al., "Phase II trial of cisplatin and gemcitabine in patients with advanced gastric cancer," Annals of Oncology (2004), vol. 15, pp. 484-488.
Extended European Search Report issued Jun. 14, 2012, in European Patent Application No. 08704376.6.
Response filed Sep. 6, 2012, in reply to the Office Action issued Jun. 8, 2012, in U.S. Appl. No. 13/083,338.

Sihto et al., "KIT and Platelet-Derived Growth Factor Receptor Alpha Tyrosine Kinase Gene Mutations and KIT Amplifications in Human Solid Tumors," Journal of Clinical Oncology (Jan. 1, 2005) vol. 23, No. 1, pp. 49-57.
Canadian Office Action dated Sep. 19, 2012, for Application No. 2,627,598.
Decision of Patent Grant dated Sep. 4, 2012, for Japanese Application No. 2009-123432, with English translation.
Funahashi et al., "P-2123, Lenvatinib treatment of differentiated thyroid cancer (DTC): Analysis to identify biomarkers associated with response", The 71st Annual Meeting of the Japanese Cancer Association, Sep. 19-21, 2012, p. 339.
Reexamination Request dated Sep. 11, 2012 for Chinese Application No. 2006800203177.5, with English translation.
Response filed Jul. 5, 2012, for Chinese Application No. 200880115011.7, with English translation.
Schlumberger et al., "A Phase 2 Trial of the Multi-Targeted Kinase Inhibitor Lenvatinib (E7080) in Advanced Medullary Thyroid Cancer (MTC)", 2012 ASCO Annual Meeting, Poster Presentation, Jun. 1-5, 2012, 6 pages.
Tohyama et al., "P-3111, Preclinical effect of lenvatinib on human thyroid cancer targeting angiogenesis and receptor tyrosine kinase singnaling", The 71st Annual Meeting of the Japanese Cancer Association, dated Sep. 19-21, 2012, p. 502.
Kleespies et al,. "Tyrosine kinase inhibitors and gemcitabine: New treatment options in pancreatic cancer?," Drug Resistance Updates (2006), vol. 9, pp. 1-18.
Office Action issued Sep. 27, 2011, in U.S. Appl. No. 12/523,495.
Notice of Reasons for Rejection issued Oct. 9, 2012, in Japanese Patent Application No. P2007-516724, with English translation.
Third Office Action issued Sep. 28, 2012, in Chinese Patent Application No. 200780017371.9, with English translation.
Notice of Reasons for Rejection issued Oct. 9, 2012, in Japanese Patent Application No. P2008-516724, with English translation.
Decision to Grant a European Patent Pursuant to Article 97(1) EPC issued Nov. 2, 2012, in European Patent Application No. 06782407.8.
Decision to Grant a European Patent Pursuant to Article 97(1) EPC issued Nov. 2, 2012, in European Patent Application No. 07806561.2.
Notice of Reasons for Rejection issued Nov. 13, 2012, in Japanese Patent Application No. P2008-532141, with English translation.
Notification of Defects issued Oct. 15, 2012, in Israel Patent Application No. 200090, with English translation.
"Asu no Shinyaku" ("The New Drugs of Tomorrow"), Update Summary, Dec. 2006, ISSN 1343-4462, pp. 81-83.
Agarwal et al., "Binding of Discoidin Domain Receptor 2 to Collagen I: An Atomic Force Microscopy Investigation," Biochemistry, vol. 41, pp. 11091-11098, 2002.
Alvares Da Silva et al., "A Novel Germ-Line Point Mutation in RET Exon 8 (Gly533Cys) in a Large Kindred with Familiar Medullary Thyroid Carcinoma", The Journal of Clinical Endocrinology & Metabolism, vol. 88, No. 11, 2003, pp. 5438-5443.
Baker et al., "Blockade of Vascular Endothelial Growth Factor Receptor and Epidermal Growth Factor Receptor Signalling for Therapy of Metastatic Human Pancratic Cancer," Cancer Research, vol. 62, pp. 1996-2003, Apr. 1, 2002.
Benjamin et al., "Selective Ablation of Immature Blood Vessels in Estabished Human Tumors Follows Vascular Endothelial Growth Factor Withdrawal", The Journal of Clinical Investigation, vol. 103, No. 2, Jan. 1999, p. 159-165.
Bergers et al., "Benefits of Targeting Both Pericytes and Endothelial Cells in the Tumor and Vasculature with Kinase Inhibitors", The Journal of Clinical Investigation, vol. 111, No. 9, May 2003, pp. 1287-1295.
Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer, vol. 102, 2002, pp. 101-108.
Cappellen et al., "Frequent Activating Mutations of FGFR3 in Human Bladder and Cervix Carcinomas," Nature Genetics, vol. 23, Sep. 1999, pp. 18-20.

(56) References Cited

OTHER PUBLICATIONS

Carlomagno et al., "BAY 43-9006 Inhibition of Oncogenic RET Mutants", Journal of the National Cancer Institute, vol. 98, No. 5, Mar. 1, 2006, pp. 326-334.
Carlomagno et al., "ZD6474, an Orally Available Inhibitor of KDR Tyrosine Kinase Acrivity, Efficiently Blocks Oncogenic RET Kinases," Cancer Research, vol. 62, pp. 7284-7290, Dec. 15, 2002.
Chen et al., "FGFR3 as a Therapeutic Target of the Small Molecule Inhibitor PKC412 in Hematopoietic Malignancies", Oncogene, vol. 24, 2005, pp. 8259-8267.
Chesi et al., "Activated fibroblast growth factor receptor 3 is an oncogene that contributes to tumor progression in multiple myeloma," Blood, vol. 97, No. 3, pp. 729-736, Feb. 1, 2001.
Chesi et al., "Frequent Translocation t(4;14)(p16.3:q32.3) in Multiple Myeloma is Associated with Increased Expression and Activating Mutations of Fibroblast Growth Factor Receptor 3", Nature Genetics, vol. 16, Jul. 1997, pp. 260-264.
Elisei et al., "Identification of a Novel Point Mutation in the RET Gene (Ala883Thr), Which is Associated with Medullary Thyroid Carcinoma Phenotype Only in Homozygous Condition", The Journal of Clinical Endocrinology & Metabolism, vol. 89, No. 11, 2004, pp. 5823-5827.
Erber et al., "Combined Inhibition of VEGF- and PDGF-Signaling Enforces Tumor Vessel Regression by Interfering with Pericyte-mediated Endothelial Cell Survival Mechanisms", FASEB Journal, vol. 18, No. 2, 2004, pp. 338-340, XP-002548466.
European Office Action for European Application No. 04719054.1, dated Oct. 30, 2009.
Extended European Search Report for European Application No. 06782407.8 dated Jul. 23, 2010.
Gatzemeier et al., "Phase III Comparative Study of High-Dose Cisplatin Versus a Combination of Paclitaxel and Cisplatin in Patients with Advanced Non-Small-Cell Lung Cancer", Journal of Clinical Oncology, vol. 18, No. 19, pp. 3390-3399, Oct. 1, 2000.
Giles, "The Vascular Endothelial Growth Factor (VEGF) Signaling Pathway: A Therapeutic Target in Patients with Hematologic Malignancies", The Oncologist, vol. 6, Suppl. 5, 2001, pp. 32-39.
Haller, "Chemotherapy for Advanced Pancreatic Cancer", Int. J. Radiation Oncology Biol. Phys., vol. 56, No. 4, Supplement, 2003, pp. 16-23.
Hattori et al., "Immunohistochemical Detection of K-sam Protein in Stomach Cancer", Clinical Cancer Research, vol. 2, No. 8, Aug. 1996, pp. 1373-1381.
Haymo et al., "Principles in Experimental MDA-MB231 Tumor Angiogenesis", Histochemistry and Cell Biology, vol. 117, No. 6, Jun. 2002, pp. 527-534.
Hurwitz et al., "Bevacizumab Plus Irinotecan, Fluorouracil, and Leucovorin for Metastatic Colorectal Cancer", The New England Journal of Medicine, vol. 350, No. 23, Jun. 3, 2004, pp. 2335-2342.
Inai et al., "Inhibition of Vascular Endothelial Growth Factor (VEGF) Signaling in Cancer Causes Loss of Endothelial Fenestrations, Regression of Tumor Vessels, and Appearance of Basement Membrane Ghosts," American Journal of Pathology, vol. 165, No. 1, pp. 35-52, Jul. 2004.
Inoue et al., "Molecular Target Therapy Targeting Angiogenesis Pathways", The Nishinihon Journal of Urology, vol. 66, 2004, pp. 425-432.
International Search Report for Application No. PCT/JP2006/322514, dated Jan. 23, 2007.
International Search Report for Application No. PCT/JP2006/323881, dated Jan. 23, 2007.
International Search Report for Application No. PCT/JP2007/060560, dated Sep. 11, 2007.
International Search Report for Application No. PCT/JP2007/063525, dated Sep. 4, 2007.
International Search Report for Application No. PCT/JP2007/067088, dated Nov. 20, 2007.
International Search Report for Application No. PCT/JP2008/051024, dated Apr. 1, 2008.
International Search Report for Application No. PCT/JP2008/051697, dated Mar. 4, 2008.
International Search Report for Application No. PCT/JP2008/070321, dated Jan. 20, 2009.
International Search Report for Application No. PCT/JP2009/051244, dated Mar. 24, 2009.
International Search Report for Application No. PCT/JP2010/063804, dated Sep. 14, 2010.
International Search Report for Application No. PCT/JP2006/315698, dated Oct. 17, 2006.
International Search Report for Application No. PCT/JP2006/315563, dated Sep. 5, 2006.
Itoh et al., "Preferential Alternative Splicing in Cancer Generates a K-sam Messenger RNA with Higher Transforming Activity," Cancer Research, vol. 54, pp. 3237-3241, Jun. 15, 1994.
Jhiang, "The RET Proto-Oncogene in Human Cancers", Oncogene, vol. 19, 2000, pp. 5590-5597.
Jiminez et al., "Pheochromocytoma and Medullary Thyroid Carcinoma: A New Genotype-Phenotype Correlation of the RET Protooncogene 891 Germline Mutation", The Journal of Clinical Endocrinology & Metabolism, vol. 89, No. 8, 2004, pp. 4142-4145.
Johnson et al., "Paclitaxel Plus Carboplatin in Advanced Non-Small-Cell Lung Cancer: A Phase II Trial", Journal of Clinical Oncology, vol. 14, No. 7, Jul. 1996, pp. 2054-2060.
Jung et al., "Effects of Combination Anti-Vascular Endothelial Growth Factor Receptor and Anti-Epidermal Growth Factor Receptor Therapies on the Growth of Gastric Cancer in a Nude Mouse Model", European Journal of Cancer, vol. 38, 2002, pp. 1133-1140.
Kashuk et al., "Phenotype-Genotype Correlation in Hirschsprung Disease is Illuminated by Comparative Analysis of the RET Protein Sequence", PNAS, vol. 102, No. 25, Jun. 21, 2005, pp. 8949-8954.
Kelly et al., "Randomized Phase III Trial of Paclitaxel Plus Carboplatin Versus Vinorelbine Plus Cisplatin in the Treatment of Patients with Advanced Non-Small-Cell Lung Cancer: A Southwest Oncology Group Trial", Journal of Clinical Oncology, vol. 19, No. 13, Jul. 1, 2001, pp. 3210-3218.
Kim et al., "A Phase II Study of Irinotecan Plus Cisplatin for Patients with Advanced Stage IIIB or IV NSCLC Previously Treated With Nonplatinum-Based Chemotherapy," Cancer, vol. 107, pp. 799-805, 2006.
Kim et al., "An Orally Administered Multitarget Tyrosin Kinase Inhibitor, SU11248, is a Novel Potent Inhibitor of Thyroid Oncogenic RET/Papillary Thyroid Cancer Kinases", The Journal of Clinical Endocrinology & Metabolism, vol. 91, No. 10, 2006, pp. 4070-4076.
Lesueur et al., "Polymorphisms in RET and Its Coreceptors and Ligands as Genetic Modifiers of Multiple Endocrine Neoplasia Type 2A," Cancer Research, vol. 66, No. 2, pp. 1177-1180, Jan. 15, 2006.
Lin et al., "The Vascular Endothelial Growth Factor Receptor Tyrosine Kinase Inhibitor PTK787/ZK222584 Inhibits Growth and Migration of Multiple Myeloma Cells in the Bone Marrow Microenvironment," Cancer Research, vol. 62, pp. 5019-5026, Sep. 1, 2002.
Logie et al., "Activating Mutations of the Tyrosine Kinase Receptor FGFR3 Are Associated with Benign Skin Tumors in Mice and Humans", Human Molecular Genetics, vol. 14, No. 9, 2005, pp. 1153-1160.
Matsui et al., "E7080, a novel multi-targeted tyrosine kinase inhibitor, exhibits anti-angiogenic activity via inhibition of KIT signalling in a small cell lung cancer xenograft model," European Journal of Cancer, vol. 2, No. 8, 2004, p. 47, #146.
McCarty et al., "ZD6474, a Vascular Endothelial Growth Factor Receptor Tyrosine Kinase Inhibitor with Additional Activity Against Epidermal Growth Factor Receptor Tyrosine Kinase, Inhibits Orthopic Growth and Angiogenesis of Gastric Cancer", Mol. Cancer Ther., vol. 3, No. 9, 2004, pp. 1041-1048.
McCulloch et al., "Astragalus-Based Chinese Herbs and Platinum-Based Chemotherapy for Advanced Non-Small-Cell Lung Cancer: Meta-Analysis of Randomized Trials", Journal of Clinical Oncology, vol. 24, No. 3, Jan. 20, 2006, pp. 419-430.
Miller et al., "Paclitaxel Plus Bevacizumab Versus Paclitaxel Alone for Metastatis Breast Cancer", New England Journal of Medicine, vol. 357, 2007, pp. 2666-2676.

(56) References Cited

OTHER PUBLICATIONS

Mologni et al., "Inhibition of RET Tyrosine Kinase of SU5416", Journal of Molecular Endocrinology, vol. 37, No. 2, 2006, pp. 199-212, XP003022512.
Morgan et al., "Dynamic Contrast-Enhanced Magnetic Resonance Imaging as a Biomarker for the Pharmacological Response of PTK787/ZK222584, an Inhibitor of the Vascular Endothelial Growth Factor Receptor Tyrosine Kinases . . . ," Journal of Clinical Oncology, vol. 21, No. 21, Nov. 1, 2003, pp. 3955-3964.
Morikawa et al., "Angiogenesis and Pericytes: Putative Positive Function of Pericytes in Angiogenesis," The Cell, vol. 37, No. 4, 2005, pp. 164-168.
Naski et al., "Graded Activation of Fibroblast Growth Factor Receptor 3 by Mutations Causing Achondroplasia and Thanatophoric Dysplasia", Nature Genetics, vol. 13, pp. 233-237, Jun. 1996.
Ohe et al., "Randomized phase III study of cisplatin plus irinotecan versus carboplatin plus paclitaxel, cisplatin plus gemcitabine, and cisplatin plus vinorelbine for advanced non-small-cell lung cancer . . . ," Annals of Oncology, vol. 18, pp. 317-323, 2007.
Olaso et al., "DDR2 Receptor Promotes MMP-2-Mediated Proliferation and Invasion by Hepatic Stellate Cells", The Journal of Clinical Investigation, vol. 108, No. 9, Nov. 2001, pp. 1369-1378.
Ozols et al., "Phase III Trial of Carboplatin and Paclitaxel Compared with Cisplatin and Paclitaxel in Patients with Optimally Resected Stage III Ovarian Cancer: A Gynecologic Oncology Group Study", Journal of Clinical Oncology, vol. 21, No. 17, Sep. 1, 2003, pp. 3194-3200.
Paterson et al., "Preclinical studies of fibroblast growth factor receptor 3 as a therapeutic target in multiple myeloma," British Journal of Haematology, vol. 124, pp. 595-603, 2004.
Plowright et al., "Ectopic expression of fibroblast growth factor receptor 3 promotes myeloma cell proliferation and prevents apoptosis," Blood, vol. 95, No. 3, pp. 992-998, Feb. 1, 2000.
Proceedings of the American Association for Cancer Research, Experimental and Molecular Therapeutics, vol. 47, Apr. 2006, p. 890.
Salmon et al., "Anti-Angiogenic Treatment of Gastrointestinal Malignancies," Cancer Investigation, vol. 23, pp. 712-726, 2005.
Sandler et al., "Phase III Trial Gemcitabine Plus Cisplatin Versus Cisplatin Alone in Patients with Locally Advanced or Metastatic Non-Small-Cell Lung Cancer", Journal of Clinical Oncology, vol. 18, No. 1, Jan. 2000, pp. 122-130.
Santoro et al., "Drug Insight: Small-Molecule Inhibitors of Protein Kinases in the Treatment of Thyroid Cancer", Nature Clinical Practice Endocrinology & Metabolism, vol. 2, No. 1, pp. 42-52, Jan. 2006.
Santoro et al., "Minireview: RET: Normal and Abnormal Functions", Endocrinology, vol. 145, No. 12, pp. 5448-5451, 2004.
Shiang et al., "Mutations in the Transmembrane Domain of FGFR3 Cause the Most Common Genetic Form of Dwarfism, Achondroplasia," Cell, vol. 78, pp. 335-342, Jul. 29, 1994.
Shimizu et al., "Orally active anti-proliferation agents: novel diphenylamine derivatives as FGF-R2 autophosphorylation inhibitors," Bioorganic & Medicinal Chemisty Letters, vol. 14, pp. 875-879, 2004.
Supplementary European Search Report for European Application No. 07743994.1 dated May 4, 2010.
Takahashi et al., "A case of inoperable scirrhous gastric cancer that responded remarkably to a combination of TS-1+Paclitaxel . . . ," Japanese Journal of Cancer Chemother., vol. 31, No. 7, Jul. 2004, pp. 1093-1095.
Tan et al., "Randomized Study of Vinorelbine-Gemcitabine Versus Vinorelbine-Carboplatin in Patients with Advanced Non-Small Cell Lung Cancer", Lung Cancer, vol. 49, No. 2, 2005, pp. 233-240.
Trudel et al., "CHIR-258, a novel, multitargeted tyrosine kinase inhibitor for the potential treatment of t(4;14) multiple myeloma," Blood, vol. 105, pp. 2941-2948, 2005.
Trudel et al., "Inhibition of fibroblast growth factor receptor 3 induces differentiation and apoptosis in t(4;14) myeloma," Blood, vol. 103, No. 9, pp. 3521-3528, May 1, 2004.
U.S. Notice of Allowance for U.S. Appl. No. 12/244,227, dated Oct. 22, 2010.
Ueda et al., "Deletion of the Carboxyl-Terminal Exons of K-sam/FGFR2 by Short Homology-mediated Recombination, Generating Preferential Expression of Specific Messenger RNAs," Cancer Research, vol. 59, pp. 6080-6086, Dec. 15, 1999.
US Office Action for U.S. Appl. No. 10/797,903, dated Aug. 20, 2009.
Van Oers et al., "A Simple and Fast Method for Simultaneous Detection of Nine Fibroblast Growth Factor Receptor 3 Mutations in Bladder Cancer and Voided Urine", Clinical Cancer Research, vol. 11, No. 21, Nov. 1, 2005, pp. 7743-7748.
Vogel et al., "Sensing extracellular matrix: An update on discoidin domain receptor function," Cellular Signalling, vol. 18, pp. 1108-1116, 2006.
Wakui, "Chemotherapy for Scirrhous Gastric Cancer", Jpn. J. Cancer Chemother., vol. 21, No. 14, Oct. 1994, pp. 2398-2406.
Almarsson et al., "High-Throughput Surveys of Crystal Form Diversity of Highly Polymorphic Pharmaceutical Compounds," Crystal Growth & Design, Sep. 10, 2003, 3(6):927-933.
Amended Claims filed in EP App. Ser. No. 11798224.9, filed Aug. 2, 2013, 35 pages.
Amended Claims filed in KR App. Ser. No. 10-2010-7011023, filed Jul. 17, 2013, 15 pages (with English translation).
Amended Claims filed in RU App. Ser. No. 2013140169, dated Aug. 29, 2013, 17 pages (with English translation).
Amended Specification filed in AU App. Ser. No. 2012246490, filed Aug. 2, 2013, 15 pages.
Amendment and RCE submission documents filed in U.S. Appl. No. 12/039,381, dated Oct. 23, 2013, 13 pages.
Amendment and Response filed in U.S. Appl. No. 11/997,543, dated Dec. 19, 2013, 38 pages.
Amendment and Response to Office Action under 37 C.F.R § 1.111 for U.S. Appl. No. 12/439,339, dated Aug. 22, 2013, 14 pages.
Amendment filed in BR App. Ser. No. BR112012032462-4, dated Nov. 4, 2013, 21 pages (with English translation).
Amendment filed in EP App. Ser. No. 12774278.1, filed Aug. 13, 2013, 12 pages.
Amendment filed in EP App. Ser. No. 12793322.4, dated Nov. 28, 2013, 6 pages.
Amendment filed in JP App. Ser. No. 2008-532141, filed Jul. 5, 2013, 2 pages (with English translation).
Amendment filed in KR App. Ser. No. 10-2008-7029472, dated May 1, 2014, 14 pages (with English translation).
Amendment filed in KR App. Ser. No. 10-2008-7029472, dated Nov. 20, 2013, 81 pages (with English translation).
Amendment filed in KR App. Ser. No. 10-2009-7005657, dated May 7, 2014, 15 pages (with English translation).
Amendment filed in KR App. Ser. No. 10-2009-7017694, dated Feb. 28, 2014, 7 pages.
Amendment filed in KR App. Ser. No. 10-2013-7020616, dated Nov. 22, 2013, 22 pages (with English translation).
Amendment filed in U.S. Appl. No. 13/805,826, dated Sep. 9, 2013, 14 pages.
Amendment filed on Aug. 13, 2013 in JP App. Ser. No. P2009-540099, 8 pages (with English translation).
Amendment filed on Aug. 29, 2013 in CN App. Ser. No. 201280010898.X, 24 pages (with English translation).
Amendment filed on Aug. 6 2013, for JP App. Ser. No. 2009-551518, 6 pages (with English translation).
Amendment filed on Oct. 1, 2013 in IN App. Ser. No. 10502/CHENP/2012, 10 pages.
Amendment filed on Sep. 23, 2013 in AU App. Ser. No. 2011270165, 35 pages.
Amendment for IN App. Ser. No. 7026/CHENP/2013, dated Sep. 5, 2013, 8 pages.
Amendment in Canadian App. Ser. No. 2828946, dated Aug. 30, 2013, 14 pages.
Amendment in Israeli App. Ser. No. 200090, dated Oct. 2, 2013, 10 pages (with English translation).
Amendment in Korean App. Ser. No. 10-2012-7033886, dated Sep. 27, 2013, 34 pages (with English translation).
Amendment in Mexican App. Ser. No. MX/a/2012/014776, dated Oct. 21, 2013, 5 pages.

(56) References Cited

OTHER PUBLICATIONS

Amendment in Russian App. Ser. No. 2012158142, dated Oct. 17, 2013, 48 pages (with English translation).
Amendment, Response to Office Action under 37 C.F.R. § 1.111 and Information Disclosure Statement for U.S. Appl. No. 13/624,278, filed Jun. 28, 2013, 23 pages.
Applicant Observation for CN App. Ser. No. 200780017371.9, filed May 29, 2013, 6 pages (with English translation).
Argument and Amendment for JP App. Ser. No. 2008-556208, filed Mar. 21, 2013, 15 pages (with English translation).
Argument and Amendment for JP App. Ser. No. 2008-532141, filed Nov. 29, 2012, 12 pages (with English translation).
Argument and Amendment for JP App. Ser. No. 2008-516724, filed Nov. 28, 2012, 22 pages (with English translation).
Argument and Amendment for JP. App. Ser. No. 2009-123432, dated Jun. 12, 2012, 12 pages (with English translation).
Argument and Amendment for JP. App. Ser. No. 2009-529019, dated Jul. 3, 2012, 14 pages (with English translation).
Argument filed on Aug. 13, 2013 in JP App. Ser. No. 2009-540099, 10 pages (with English translation).
Argument filed on Aug. 6, 2013 for Jp Patent Application No. 2009-551518, 18 pages (with English translation).
Chikahisa et al, "TSU-68 KDR/flk-1 inhibitor, can modulate the anti-tumor activity of paclitaxel by the induction of endothelial cell and tumor cell apoptosis," 61st Annual Meeting of the Japanese Cancer Association, 2002, 61(1374):443, 5 total pages (with English translation).
Colombian Office Action for App. Ser. No. 12-022608, dated Oct. 7, 2013, 10 pages (with English translation).
Continuation Patent Application, Preliminary Amendment and Information Disclosure Statement for U.S. Appl. No. 13/923,858, filed Jun. 21, 2013, 97 pages.
Decision of Final Rejection issued in CN App. Ser. No. 200780017371.9, dated Jul. 3, 2013, 16 pages (with English translation).
Demand for Appeal Trial filed in JP App. Ser. No. 2008-532141, filed Jul. 5, 2013, 10 pages (with English translation).
Explanation of Circumstances Concerning Accelerated Examination filed May 10, 2012 for JP Patent Application No. 2011-527665, 21 pages (with English Translation).
Ezzat et al., "Dual Inhibition of RET and FGFR4 Retains Medullary Thyroid Cancer Cell Growth," Clinical Cancer Research, Feb. 2005, 11:1336-1341.
Frings, "New Molecular Targeted Therapeutic Drugs Clinical Results of Bevacizumab in Non-Small Cell Lung Cancer (NSCLC)", Jap. J. Lung Cancer, Jun. 2006, 46(3):277-281 (with English Translation).
Indian Office Action in App. Ser. No. 6415/CHENP/2008, dated Oct. 3, 2013, 2 pages.
International Preliminary Report on Patentability in International App. Ser. No. PCT/JP2012/060279, dated Oct. 23, 2013, 11 pages.
International Preliminary Report on Patentability in International App. Ser. No. PCT/JP2012/062509, dated Nov. 28, 2013, 11 pages.
International Preliminary Report on Patentability in PCT App. Ser. No. PCT/US2012/040183, 9 pages.
Jiang, "ZD6474: an Agent That Selectively Targets Both VEGFR Tyrosine Kinase and EGFR Tyrosine Kinase", Jap. J. Lung Cancer, Jun. 2006, 46(3):283-288 (with English translation).
Korean Office Action for App. Ser. No. 10-2009-7005657, issued on Sep. 30, 2013, 27 pages (with English translation).
Korean Office Action in Kr App. Ser. No. 10-2008-7029472, dated Sep. 30, 2013, 27 pages (with English translation).
Koyama et al, "Anti-tumor effect of E7080, a novel angiogenesis inhibitor," Folia Pharmacol. Japan., 2008, 132: 100-104 (with English translation).
Matsui, "Extracellular matrix of linitis plastica as a possible new therapeutic target," Surgical Treatment, Sep. 2003, 89(3):301-306 (with English translation).
Mexican Office Action in App. Ser. No. MX/a/2010/008187, dated Aug. 21, 2013, 6 pages (with English translation).
Nakazawa et al., "Maximizing the efficacy of anti-angiogenesis cancer therapy: A multi-targeting strategy by tyrosine kinase inhibitors," AACR Annual Meeting 2014, Presentation Abstract and Poster, Apr. 5-9, 2014, 2 pages.
Nishio et al, "Phase 1 study of lenvatinib combined with carboplatin and paclitaxel in patients with non-small-cell lung cancer", British Journal of Cancer, 2013, 109:538-544.
Notice of Acceptance for AU App. Ser. No. 2009210098, dated Jun. 4, 2013, 3 pages.
Notice of Allowance dated May 6, 2013 for EP App. Ser. No. 04818213.3, 22 pages.
Notice of Allowance for CN App. Ser. No. 200980103218.7, dated May 27, 2013, 4 pages (with English translation).
Notice of Allowance for JP App. Ser. No. P2008-532141, dated Sep. 10, 2013, 5 pages (with English translation).
Notice of Allowance for U.S. Appl. No. 12/741,682, dated Jun. 19, 2013, 10 pages.
Notice of Allowance for U.S. Appl. No. 11/997,719, dated Sep. 13, 2013, 20 pages.
Notice of Allowance for U.S. Appl. No. 13/083,338, dated Jun. 4, 2013, 57 pages.
Notice of Allowance for U.S. Appl. No. 13/083,338, dated Sep. 26, 2013, 28 pages.
Notice of Allowance for U.S. Appl. No. 13/205,328, dated Jun. 10, 2013, 58 pages.
Notice of Allowance for U.S. Appl. No. 13/205,328, dated Oct. 3, 2013, 11 pages.
Notice of Allowance in CA App. Ser. No. 2652442, dated Apr. 16, 2014, 1 page.
Notice of Allowance in EP App. Ser. No. 04818213.3, dated Sep. 19, 2013, 2 pages.
Notice of Allowance in IL App. Ser. No. 200090, dated Nov. 18, 2013, 5 pages (with English translation).
Notice of Allowance in JP App. Ser. No. P2009-551518, dated Oct. 22, 2013, 5 pages (with English translation).
Notice of Allowance in KR App. Ser. No. 10-2008-7013685, dated Nov. 29, 2013, 3 pages (with English translation).
Notice of Allowance in UA App. Ser. No. a201203132, dated Mar. 21, 2014, 6 pages.
Notice of Allowance in U.S. Appl. No. 12/439,339, dated Apr. 1, 2014, 17 pages.
Notice of Allowance in U.S. Appl. No. 12/439,339, dated Nov. 7, 2013, 64 pages.
Notice of Allowance in U.S. Appl. No. 12/524,754, dated Feb. 13, 2014, 18 pages.
Notice of Allowance in U.S. Appl. No. 12/524,754, dated Nov. 22, 2013, 12 pages.
Notice of Allowance in U.S. Appl. No. 12/741,682, dated Feb. 7, 2014, 11 pages.
Notice of Allowance in U.S. Appl. No. 12/741,682, dated Oct. 21, 2013, 12 pages.
Notice of Allowance in U.S. Appl. No. 13/083,338, dated Feb. 6, 2014, 15 pages.
Notice of Allowance in U.S. Appl. No. 13/205,328, dated Jan. 30, 2014, 11 pages.
Notice of Allowance in U.S. Appl. No. 13/205,328, dated May 8, 2014, 10 pages.
Notice of Allowance in U.S. Appl. No. 13/624,278, dated Sep. 16, 2013, 20 pages.
Notice of Allowance in VN App. Ser. No. 1-2011-03484, dated Apr. 28, 2014, 2 pages.
Notice of Allowance issued in CN App. Ser. No. 200880115011.7, dated Aug. 5, 2013, 4 pages (with English translation).
Notice of Allowance issued in CN App. Ser. No. 201080030508.6, dated Jul. 4, 2013, 4 pages (with English translation).
Notice of Allowance issued in EP App. Ser. No. 10015141.4, dated Jul. 1, 2013, 41 pages.
Notice of Allowance issued in IL App. Ser. No. 175363, dated Aug. 13, 2013, 2 pages (with English translation).
Notice of Allowance issued in JP App. Ser. No. P2008-556208, dated Jul. 9, 2013, 4 pages (with English translation).
Notice of Allowance issued in U.S. Appl. No. 12/524,754, dated Jul. 19, 2013, 11 pages.

(56) References Cited

OTHER PUBLICATIONS

Notice of Reasons for Rejection issued in JP App. Ser. No. P2009-540099, dated Jul. 2, 2013, 7 pages (with English translation).
Notification of Defects for IL App. Ser. No. 195282, dated Apr. 10, 2013, 4 pages (with English Translation).
Observation for CN App. Ser. No. 200880115011.7, dated Apr. 11, 2013, 10 pages (with English translation).
Observations for CN App. Ser. No. 201080030508.6, dated May 27, 2013, 7 pages (with English translation).
Office Action dated Apr. 11, 2013 for IL App. Ser. No. 217197, 4 pages (with English translation).
Office Action dated Apr. 16, 2013 for CA App. Ser. No. 2652442, 2 pages.
Office Action dated Apr. 8, 2013 for U.S. Appl. No. 11/997,719, 55 pages.
Office Action dated Apr. 9, 2013 for CN App. Ser. No. 201080030508.6, 6 pages (with English translation).
Office Action dated Mar. 14, 2013 for CN App. Ser. No. 200780017371.9, 9 pages (with English translation).
Office Action for EP App. Ser. No. 08846814.5, dated Apr. 16, 2013, 5 pages.
Office Action for IL App. Ser. No. 200090, dated Jul. 24, 2013, 5 pages (with English translation).
Office Action for JP App. Ser. No. P2008-532141, dated May 21, 2013, 4 pages (with English translation).
Office Action for JP App. Ser. No. P2009-551518, dated Jun. 18, 2013, 5 pages (with English translation).
Office Action for KR App. Ser. No. 10-2008-7013685, dated May 20, 2013, 10 pages (with English translation).
Office Action for PH App. Ser. No. 1-2011-502441 on Oct. 1, 2013, 1 page.
Office Action for U.S. Appl. No. 12/039,381, dated Sep. 12, 2013, 15 pages.
Office Action for U.S. Appl. No. 13/238,085, dated Sep. 6, 2013, 10 pages.
Office Action for U.S. Appl. No. 12/439,339, dated May 23, 2013, 15 pages.
Office Action in CA App. Ser. No. 2652442, dated Oct. 4, 2013, 2 pages.
Office Action in CA App. Ser. No. 2676796, dated Dec. 30, 2013, 5 pages.
Office Action in CN App. Ser. No. 200680020317.5, dated Mar. 4, 2014, 13 pages.
Office Action in CN App. Ser. No. 200680020317.5, dated Nov. 28, 2013, 8 pages (with English translation).
Office Action in CN App. Ser. No. 201180030568.2, dated Mar. 24, 2014, 8 pages (with English translation).
Office Action in CN App. Ser. No. 201180030568.2, dated Oct. 12, 2013, 11 pages (with English translation.
Office Action in CO App. Ser. No. 12-022608, dated Dec. 17, 2013, 12 pages (with English translation).
Office Action in EP App. Ser. No. 04807580.8, dated Mar. 18, 2014, 12 pages.
Office Action in EP App. Ser. No. 08704376.6, dated Feb. 24, 2014, 4 pages.
Office Action in IL App. Ser. No. 205512, dated Oct. 28, 2013, 5 pages (with English translation).
Office Action in IL App. Ser. No. 207089, dated Nov. 25, 2013, 6 pages (with English translation).
Office Action in IN App. Ser. No. 1571/CHENP/2007, dated Oct. 23, 2013, 2 pages.
Office Action in IN App. Ser. No. 1571/CHENP/2007, Dec. 9, 2013, 2 pages.
Office Action in JP App. Ser. No. P2009-540099, dated Mar. 25, 2014, 6 pages (with English translation).
Office Action in KR App. Ser. No. 10-2008-7029472, dated Mar. 28, 2014, 6 pages (with English translation).
Office Action in KR App. Ser. No. 10-2009-7005657, dated Mar. 28, 2014, 6 pages (with English translation).
Office Action in KR App. Ser. No. 10-2009-7017694, dated Jan. 29, 2014, 26 pages (with English translation).
Office Action in MX App. Ser. No. MX/a/2010/008187, dated Dec. 5, 2013, 8 pages (with English translation).
Office Action in MX App. Ser. No. MX/a/2012/002011, dated Nov. 21, 2013, 8 pages (with English translation).
Office Action in PH App. Ser. No. 1-2011-502441, dated Feb. 19, 2014, 2 pages.
Office Action in U.S. Appl. No. 11/997,543, dated Mar. 11, 2014, 20 pages.
Office Action in U.S. Appl. No. 12/039,381, dated Jan. 9, 2014, 16 pages.
Office Action in U.S. Appl. No. 13/238,085, dated Nov. 12, 2013, 74 pages.
Office Action in U.S. Appl. No. 13/805,826, dated Apr. 2, 2014, 8 pages.
Office Action in U.S. Appl. No. 13/923,858, dated Apr. 18, 2014, 64 pages.
Office Action in U.S. Appl. No. 14/002,018, dated Apr. 14, 2014, 28 pages.
Office Action in VN App. Ser. No. 1-2011-03484, dated Dec. 31, 2013, 2 pages (with English translation).
Office Action issued in MX App. Ser. No. MX/a/2012/002011, dated Jul. 17, 2013, 6 pages (with English translation).
Preliminary Amendment dated Apr. 26, 2013 for U.S. Appl. No. 13/870,507, 10 pages.
Preliminary Amendment filed in EP App. Ser. No. 12786619.2, dated Nov. 13, 2013, 7 pages.
Preliminary Amendment filed in U.S. Appl. No. 14/117,276, dated Nov. 12, 2013, 11 pages.
Preliminary Amendment filed in U.S. Appl. No. 14/122,339, dated Nov. 26, 2013, 10 pages.
Request for Examination in CA App. Ser. No. 2713930, dated Oct. 21, 2013, 8 pages.
Request for Re-Examination in CN App. Ser. No. 200780017371.9, dated Oct. 11, 2013, 9 pages (with English translation).
Request for Substantive Examination for ID App. Ser. No. W-00201201031, filed Jun. 3, 2013, 6 pages (with English translation).
Request for Substantive Examination for UA App. Ser. No. a201203132, filed Apr. 15, 2013, 14 pages (with English translation).
Request to Amend Complete Specification dated May 9, 2013 for AU App. Ser. No. 2009210098, 22 pages.
Response and Amended Claims filed in EP App. Ser. No. 08846814.5, filed Aug. 1, 2013, 14 pages.
Response and Amended Claims filed in EP App. Ser. No. 10809938.3, filed Jul. 19, 2013, 7 pages.
Response and Amendment for CA App. Ser. No. 2652442, dated Sep. 5, 2013, 17 pages.
Response filed in CA App. Ser. No. 2652442, dated Jan. 8, 2014, 5 pages.
Response filed in CO App. Ser. No. 12-022608, dated Nov. 13, 2013, 13 pages (with English translation).
Response filed in IL App. Ser. No. 195282, filed Jul. 11, 2013, 13 pages (with English translation).
Response filed in IN App. Ser. No. 1571/CHENP/2007, dated Oct. 30, 2013, 9 pages.
Response filed in KR App. Ser. No. 10-2009-7005657, dated Nov. 21, 2013, 46 pages (with English translation).
Response filed in MX App. Ser. No. MX/a/2010/008187, dated Nov. 4, 2013, 21 pages (with English translation).
Response filed in PH App. Ser. No. 1-2011-502441, dated Feb. 28, 2014, 4 pages.
Response filed in PH App. Ser. No. 1-2011-502441, dated Nov. 4, 2013, 28 pages.
Response filed in VN App. Ser. No. 1-2011-03484, dated Feb. 28, 2014, 40 pages (with English translation).
Response to Notice Prior to Examination filed in IL App. Ser. No. 217197, filed Jul. 31, 2013, 9 pages (with English translation).
Response to Office Action for MX App. Ser. No. MX/a/2012/002011, dated Aug. 29, 2013, 12 pages (with English translation).
Response to Office Action in CN App. Ser. No. 200680020317.5 filed on Jan. 9, 2014, 7 pages (with English translation).

(56) References Cited

OTHER PUBLICATIONS

Response to Office Action in CN App. Ser. No. 201180030568.2 filed on Jan. 13, 2014, 46 pages (with English translation).
Response to Office Action in EP App. Ser. No. 08704376.6, dated Apr. 30, 2014, 73 pages.
Response to Office Action in MX App. Ser. No. MX/a/2010/008187, dated Feb. 17, 2014, 7 pages (with English translation).
Response to Office Action in MX App. Ser. No. MX/a/2012/002011 filed on Jan. 16, 2014, 20 pages (with English translation).
Response to Office Action in U.S. Appl. No. 12/039,381, dated Apr. 3, 2014, 7 pages.
Response to Office Action under 37 C.F.R.S. 1.111 and Information Disclosure Statement for U.S. Appl. No. 11/997,719, filed Jul. 3, 2013, 26 pages.
Response to Restriction Requirement in U.S. Appl. No. 13/238,085, dated Oct. 4, 2013, 3 pages.
Response to the Office Action issued for IN App. Ser. No. 6415/CHENP/2008 filed on Jan. 17, 2014, 16 pages.
Sattler et al., "Targeting c-Kit mutations: basic science to novel therapies," Leukemia Research, 2004, 28S1:S11-S20.
Search Report in EP App. Ser. No. 11798224.9, dated Mar. 21, 2014, 1 page.
Search Report in EP App. Ser. No. 11798224.9, dated Mar. 4, 2014, 6 pages.
Shumaker et al., "Effect of lenvatinib (E7080) on the QTc interval: results from a thorough QT study in healthy volunteers," Cancer Chemother Pharmacol., published online Mar. 23, 2014, 9 pages.
St. Bernard et al., "Fibroblast Growth Factor Receptors as Molecular Targets in Thyroid Carcinoma," Endocrinology, Mar. 2005, 146(3):1145-1153.
Stahl and Wermuth, "Handbook of Pharmaceutical Salts: Properties, selection, and use," 2002, pp. 117-122.
Submission Document Before the Patent Office dated Apr. 22, 2013 for IL App. Ser. No. 207089, 7 pages (with English translation).
Submission Document Before the Patent Office for CL App. Ser. No. 2012-00412, dated Aug. 31, 2012, 6 pages (with English translation).
Submission Document Before the Patent Office re RCE in U.S. Appl. No. 13/205,328, dated Sep. 10, 2013, 12 pages.
Submission Document re Petition on Oct. 2, 2013 in CL App. Ser. No. 2012-00412, 22 pages (with English translation).
Submission Document re RCE and Information Disclosure Statement on Sep. 19, 2013 in U.S. Appl. No. 12/741,682, 19 pages.
Submission Document re RCE and Information Disclosure Statement on Oct. 18, 2013, in U.S. Appl. No. 12/524,754, 17 pages.
Submission Documents Before the Patent Office for U.S. Appl. No. 12/741,682, dated May 17, 2013, 16 pages.
Submission Documents re New Claim Set Before the Patent Office for AR App. Ser. No. P110100513, dated Aug. 27, 2013, 8 pages (with English translation).
Submission Documents re Preliminary Amendment Before the Patent Office U.S. Appl. No. 14/002,018, dated Aug. 28, 2013, 9 pages.
Submission Documents re RCE Before the Patent Office for U.S. Appl. No. 13/083,338, dated Aug. 28, 2013, 20 pages.
Submission Documents re RCE Before the Patent Office for U.S. Appl. No. 12/524,754, dated Apr. 15, 2013, 17 pages.
Submission documents re RCE filed in U.S. Appl. No. 11/997,719, dated Dec. 11, 2013, 10 pages.
Submission documents re RCE filed in U.S. Appl. No. 12/741,682, dated Jan. 17, 2014, 1 page.
Submission documents re RCE filed in U.S. Appl. No. 13/083,338, dated Dec. 2, 2013, 5 pages.
Submission documents re RCE filed in U.S. Appl. No. 13/205,328, dated Dec. 30, 2013, 1 page.
Submission documents re RCE filed in U.S. Appl. No. 13/624,278, dated Dec. 13, 2013, 10 pages.
Submission documents re RCE in U.S. Appl. No. 12/439,339, dated Jan. 27, 2014, 1 page.
Submission documents re RCE in U.S. Appl. No. 12/524,754 filed on Feb. 3, 2014, 1 page.
Submission documents re RCE in U.S. Appl. No. 13/205,328, dated Apr. 28, 2014, 1 page.
Submission of Amendments and Complete Specification dated Apr. 10, 2013 for IN App. Ser. No. 1571/CHENP/2007, 15 pages.
Submission of Documents before the Patent Office for CN App. Ser. No. 200980103218.7, dated Mar. 13, 2013, 6 pages (with English translation).
Submission of Reference Materials in KR App. Ser. No. 10-2008-7013685, filed Jul. 5, 2013, 43 pages, (with English translation).
US Office Action for U.S. Appl. No. 11/997,543, dated Sep. 30, 2013, 88 pages.
Voluntary Amendment filed in CA App. Ser. No. 2704000, filed Aug. 6, 2013, 6 pages.
Voluntary Amendment filed in CA App. Ser. No. 2802644, dated Nov. 22, 2013, 25 pages.
Wang, "Drugs of Today, Everolimus in renal cell carcinoma," Journals on the Web, Aug. 2010, vol. 46, issue 8, 1 page (abstract only).
Winkler et al., "Kinetics of vascular normalization by VEGFR2 blockade governs brain tumor response to radiation: Role of oxygenation, angiopoietin-1, and matrix metalloproteinases," Cancer Cell, Dec. 2004, 6:553-563.
Written Submission regarding hearing in IN App. Ser. No. 1571/CHENP/2007 filed on Jan. 23, 2014, 8 pages.
Zhang et al., "Synergic antiproliferative effect of DNA methyltransferase inhibitor in combination with anticancer drugs in gastric carcinoma," Cancer Sci., Sep. 2006, 97(9):938-944.

\* cited by examiner

PHARMACEUTICAL COMPOSITIONS OF 4-(3-CHLORO-4-(CYCLOPROPYLAMINO CARBONYL)AMINOPHENOXY)-7= METHOXY-6-QUINOLINECARBOXIDE

TECHNICAL FIELD

The present invention relates to pharmaceutical compositions.

BACKGROUND ART

Nitrogen-containing aromatic ring derivatives disclosed in Patent Document 1 have actions in vitro such as 1) the inhibition of infiltrating tube formation by vascular endothelial cells induced by an angiogenic factor mixture solution; 2) the inhibition of tube formation by vascular endothelial cells induced specifically by a single angiogenic factor; 3) the inhibition of angiogenic factor receptor kinase; and 4) the inhibition of cancer cell growth, and hence are extremely useful as angiogenic inhibitors and the like.

[Patent Document 1]: WO 02/32872

DISCLOSURE OF THE INVENTION

Problems to be Solved by the Invention

The present inventors have found that while studying on formulating the above nitrogen-containing aromatic ring derivatives, pharmaceutical compositions containing the above nitrogen-containing aromatic ring derivatives as active ingredients are sometimes rendered unstable. Specifically, of the nitrogen-containing aromatic ring derivatives disclosed in Patent Document 1, this holds true for the nitrogen-containing aromatic ring derivatives having a structure wherein the quinoline skeleton is linked to another heterocyclic group through an ether bond. In particular, in pharmaceutical compositions, such nitrogen-containing aromatic ring derivatives are readily decomposed under humidified and heated storage conditions; and moreover, gelation readily occurs on the surface of the pharmaceutical compositions, so that when the pharmaceutical compositions are stored under humidified conditions, delayed dissolution of the active ingredients may occur due to moisture absorption.

Accordingly, an object of the present invention is to provide a stable pharmaceutical composition comprising a nitrogen-containing aromatic ring derivative, wherein under humidified and heated storage conditions, the decomposition of the above derivative is sufficiently reduced, or the gelation on the surface of the pharmaceutical composition is sufficiently inhibited.

Means for Solving the Problems

To attain the above object, the present invention provides the pharmaceutical composition described below.

The pharmaceutical composition comprising:

an active ingredient consisting of 4-(3-chloro-4-(cyclopropylaminocarbonyl)aminophenoxy)-7-methoxy-6-quinolinecarboxamide represented by Formula (1) described below, salt thereof, or solvate of the foregoing; and (i) a compound, a 5% (w/w) aqueous solution or suspension of which has a pH of 8 or more; and/or (ii) silicic acid, salt thereof, or solvate of the foregoing.

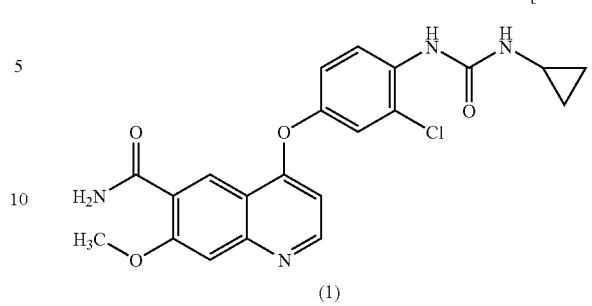

[Formula 1]

(1)

In such pharmaceutical composition, the decomposition of the compound represented by Formula (1), an active ingredient, under humidified and heated storage conditions is sufficiently reduced. Moreover, the gelation on the surface of the pharmaceutical composition is inhibited, and thereby the problem of delayed dissolution of the active ingredient after the pharmaceutical composition has been kept under humidified storage conditions is solved. Therefore, difficulties during a disintegration test or a dissolution test caused by the surface gelation of the pharmaceutical composition are eliminated, and humidity and the like do not affect the pharmaceutical composition so that the quality of the pharmaceutical composition can be ensured for a long time.

It is considered that under humidified and heated storage conditions, the suppression of the decomposition is brought about mainly by (i) the compound whose pH of a 5% (w/w) aqueous solution or suspension thereof is 8 or more, whereas the inhibition of the gelation is brought about mainly by (ii) silicic acid, salt thereof, or solvate of the foregoing. Therefore, according to requirements for the pharmaceutical composition, (i) or (ii) can be added alone or in combination thereto.

Further, it is considered that the decomposition of 4-(3-chloro-4-(cyclopropylaminocarbonyl)aminophenoxy)-7-methoxy-6-quinolinecarboxamide (hereinafter, also referred to as the "medicament X"), salt thereof, or solvate of the foregoing under humidified and heated storage conditions proceed based on the following mechanism (hereinafter, also the decomposed product having a quinoline skeleton is referred to as the "decomposed product A" and the decomposed product having 3-chloro-4-(cyclopropylaminocarbonyl)amino group as the "decomposed product B").

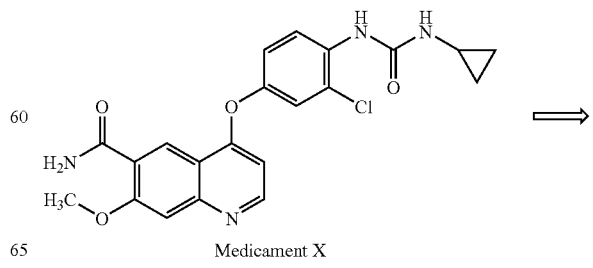

[Formula 2]

Medicament X

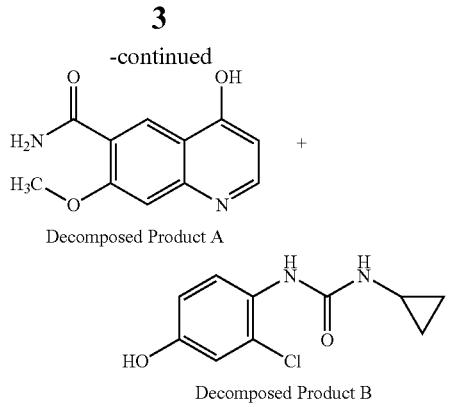

Decomposed Product A

Decomposed Product B

According to these findings, a process for improving stability of the pharmaceutical composition and a process for inhibiting gelation thereof are provided. Specifically, provided are a process for improving stability of the pharmaceutical composition comprising an active ingredient consisting of the compound represented by Formula (1) described above, salt thereof, or solvate of the foregoing by the process of adding the compound whose pH of a 5% (w/w) aqueous solution or suspension thereof is 8 or more, and a process for inhibiting gelation of the pharmaceutical composition comprising an active ingredient consisting of the compound represented by Formula (1) described above, salt thereof, or solvate of the foregoing by the process of adding silicic acid, salt thereof, or solvate of the foregoing.

In the present invention, (i) the compound whose pH of a 5% (w/w) aqueous solution or suspension thereof is 8 or more is preferably one or more selected from the group consisting of magnesium oxide, calcium oxide, sodium carbonate, disodium hydrogenphosphate, sodium citrate, dipotassium hydrogenphosphate, sodium acetate, sodium hydrogencarbonate, and sodium hydroxide; and (ii) silicic acid, salt thereof, or solvate of the foregoing is preferably one or more selected from the group consisting of light anhydrous silicic acid, silicon dioxide hydrate, calcium silicate, magnesium silicate, magnesium aluminosilicate, magnesium aluminometasilicate, magnesium aluminum silicate, synthetic aluminum silicate, and hydrous silicic dioxide.

Effect of the Invention

Provided is the highly stable pharmaceutical composition comprising a nitrogen-containing aromatic ring derivative, wherein under humidified and heated storage conditions, the decomposition of the above derivative is sufficiently reduced, or the gelation on the surface of the pharmaceutical composition is sufficiently inhibited.

BEST MODE FOR CARRYING OUT THE INVENTION

Figure 1:
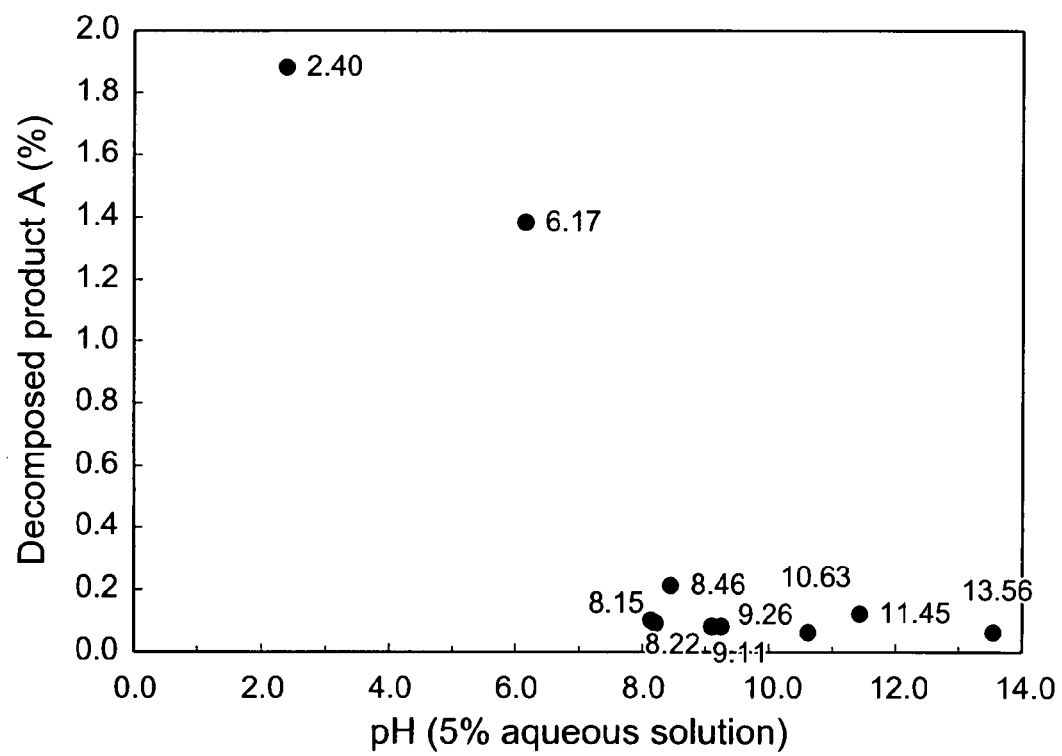
FIG. 1 illustrates the relationship between pH and the decomposed product A.

An embodiment of the present invention is explained in detail in the following paragraphs. Herein, the expression "having a diffraction peak at a diffraction angle (2θ±0.2°) of X°" means to have a diffraction peak at a diffraction angle (2θ) of from (X−0.2)° to (X+0.2)°. In general, a diffraction angle (2θ) in a powder X-ray diffraction has an error within a range of ±0.2°, and hence it should be understood that the values of the diffraction angles may include numerals on the order of ±0.2°. Accordingly, the present invention encompasses not only crystals having completely matching diffraction angles of the peaks in a powder X-ray diffraction, but also crystals having matching diffraction angles of the peaks within the errors of about ±0.2°.

(Active Ingredient)

The pharmaceutical composition in accordance with the present invention comprises the compound represented by Formula (1), salt thereof, or solvate of the foregoing as an active ingredient. The active ingredient represented by Formula (1) may be the polymorphic crystals (A') or the polymorphic crystals (B') described below.

As the polymorphic crystals (A'), the polymorphic crystals (A') of 4-(3-chloro-4-(cyclopropylaminocarbonyl)aminophenoxy)-7-methoxy-6-quinolinecarboxamide having a diffraction peak at a diffraction angle (2θ±0.2°) of 15.75° in a powder X-ray diffraction can be employed. This polymorphic crystals (A') may also have diffraction peaks at diffraction angles (2θ±0.2°) of 9.98° and 11.01° in a powder X-ray diffraction.

In an infrared spectrum (potassium bromide), these polymorphic crystals (A') may preferably have absorbance at $3452.3\pm2.5$ cm$^{-1}$ and also at $1712.2\pm1.0$ cm$^{-1}$.

As the polymorphic crystals (B'), the polymorphic crystals (B') of 4-(3-chloro-4-(cyclopropylaminocarbonyl)aminophenoxy)-7-methoxy-6-quinolinecarboxamide having a diffraction peak at a diffraction angle (2θ±0.2°) of 21.75° in a powder X-ray diffraction can be employed. This polymorphic crystals (B') may also have diffraction peaks at diffraction angles (2θ±0.2°) of 12.43° and 16.56° in a powder X-ray diffraction.

In an infrared spectrum (potassium bromide), these polymorphic crystals (B'), active ingredients, may preferably have absorbance at $1557.6\pm1.0$ cm$^{-1}$ and also at $1464.4\pm1.0$ cm$^{-1}$.

It is particularly preferred that the active ingredient represented by Formula (1) is salts, solvates, or crystals of these described below.

In particular, a suitable active ingredient is crystals of hydrochloride, hydrobromide, p-toluenesulfonate, sulfate, methanesulfonate, or ethanesulfonate of 4-(3-chloro-4-(cyclopropylaminocarbonyl)aminophenoxy)-7-methoxy-6-quinolinecarboxamide or of solvate thereof.

Specifically, crystals of methanesulfonate of 4-(3-chloro-4-(cyclopropylaminocarbonyl)aminophenoxy)-7-methoxy-6-quinolinecarboxamide or solvate thereof; crystals of ethanesulfonate of 4-(3-chloro-4-(cyclopropylaminocarbonyl)aminophenoxy)-7-methoxy-6-quinolinecarboxamide or solvate thereof; crystals of methanesulfonate of 4-(3-chloro-4-(cyclopropylaminocarbonyl)aminophenoxy)-7-methoxy-6-quinolinecarboxamide; crystals of hydrate of methanesulfonate of 4-(3-chloro-4-(cyclopropylaminocarbonyl)aminophenoxy)-7-methoxy-6-quinolinecarboxamide;

crystals of dimethyl sulfoxide solvate of methanesulfonate of 4-(3-chloro-4-(cyclopropylaminocarbonyl)aminophenoxy)-7-methoxy-6-quinolinecarboxamide; crystals of acetic acid solvate of methanesulfonate of 4-(3-chloro-4-(cyclopropylaminocarbonyl)aminophenoxy)-7-methoxy-6-quinolinecarboxamide; crystals of ethanesulfonate of 4-(3-chloro-4-(cyclopropylaminocarbonyl)aminophenoxy)-7-methoxy-6-quinolinecarboxamide; and crystals of dimethyl sulfoxide solvate of ethanesulfonate of 4-(3-chloro-4-(cyclopropylaminocarbonyl)aminophenoxy)-7-methoxy-6-quinolinecarboxamide are suitable.

The crystals of methanesulfonate of 4-(3-chloro-4-(cyclopropylaminocarbonyl)aminophenoxy)-7-methoxy-6-quinolinecarboxamide are preferably the crystals (A), the crystals (B), or the crystals (C) described below.

Specifically, the crystals (A) having diffraction peaks at diffraction angles (2θ±0.2°) of 9.65° and 18.37° in a powder X-ray diffraction; the crystals (B) having diffraction peaks at diffraction angles (2θ±0.2°) of 5.72° and 13.84° in a powder X-ray diffraction; and the crystals (C) having diffraction peaks at diffraction angles (2θ±0.2°) of 14.20° and 17.59° in a powder X-ray diffraction are preferred.

Further, the crystals of hydrate of methanesulfonate of 4-(3-chloro-4-(cyclopropylaminocarbonyl)aminophenoxy)-7-methoxy-6-quinolinecarboxamide are preferably the crystals (F) having diffraction peaks at diffraction angles (2θ±0.2°) of 8.02° and 18.14° in a powder X-ray diffraction; and the crystals of acetic acid solvate of methanesulfonate of 4-(3-chloro-4-(cyclopropylaminocarbonyl)aminophenoxy)-7-methoxy-6-quinolinecarboxamide are preferably the crystals (I) having diffraction peaks at diffraction angles (2θ±0.2°) of 9.36° and 12.40° in a powder X-ray diffraction.

Moreover, the crystals of ethanesulfonate of 4-(3-chloro-4-(cyclopropylaminocarbonyl)aminophenoxy)-7-methoxy-6-quinolinecarboxamide are preferably the crystals (α) having diffraction peaks at diffraction angles (2θ±0.2°) of 15.70° and 17.18° in a powder X-ray diffraction; and the crystals of ethanesulfonate of 4-(3-chloro-4-(cyclopropylaminocarbonyl)aminophenoxy)-7-methoxy-6-quinolinecarboxamide are preferably the crystals (β) having diffraction peaks at diffraction angles (2θ±0.2°) of 6.48° and 9.58° in a powder X-ray diffraction.

(Process for Preparing the Active Ingredient)

As for the process for preparing the compound represented by Formula (1), the description in WO 02/32872 can be used as a reference. The processes for preparing the polymorphic crystals (A') and the polymorphic crystals (B') are described in the following paragraphs.

The polymorphic crystals (A') can be obtained by a preparation process described below: 4-(3-chloro-4-(cyclopropylaminocarbonyl)aminophenoxy)-7-methoxy-6-quinolinecarboxamide is dissolved in an organic solvent, a good solvent (for example, dimethyl sulfoxide, dimethylimidazolidine, 1-methyl-2-pyrrolidinone, N,N-dimethylformamide, N,N-dimethylacetamide, acetic acid, sulfolane, etc.), and then thereto a poor solvent (for example, water, acetone, acetonitrile, ethyl acetate, isopropyl acetate, methanol, ethanol, n-propanol, isopropanol, or a mixture thereof, etc.) is admixed rapidly (for example, within 10 min.).

The polymorphic crystals (A') can be obtained by another preparation process described below: 4-(3-chloro-4-(cyclopropylaminocarbonyl)aminophenoxy)-7-methoxy-6-quinolinecarboxamide is dissolved while stirring in an organic solvent, a good solvent (for example, dimethyl sulfoxide, dimethylimidazolidine, 1-methyl-2-pyrrolidinone, N,N-dimethylformamide, N,N-dimethylacetamide, acetic acid, sulfolane, etc.), and then thereto a poor solvent (for example, water, acetone, acetonitrile, ethyl acetate, isopropyl acetate, methanol, ethanol, n-propanol, isopropanol, or a mixture thereof, etc.) is admixed so that the resultant crystals precipitate when the stirring is stopped.

The polymorphic crystals (A') can be obtained by still another preparation process described below: 7-methoxy-4-chloroquinoline-6-carboxamide and 1-(2-chloro-4-hydroxyphenyl)-3-cyclopropylurea are reacted in the presence of a base (for example, potassium t-butoxide, cesium carbonate, potassium carbonate, etc.) in an organic solvent that works a good solvent for 4-(3-chloro-4-(cyclopropylaminocarbonyl)aminophenoxy)-7-methoxy-6-quinolinecarboxamide (for example, dimethyl sulfoxide (DMSO), dimethylimidazolidinone, 1-methyl-2-pyrrolidinone, N,N-dimethylformamide, N,N-dimethylacetamide, sulfolane, etc.), and then thereto a poor solvent is admixed rapidly (for example, within 10 min.).

More specifically, for example, to a mixture of 1-(2-chloro-4-hydroxyphenyl)-3-cyclopropylurea, 7-methoxy-4-chloroquinoline-6-carboxamide (one equivalent or more based on 1-(2-chloro-4-hydroxyphenyl)-3-cyclopropylurea), and potassium t-butoxide (one equivalent or more based on 1-(2-chloro-4-hydroxyphenyl)-3-cyclopropylurea), DMSO in a volume 5 to 10 times based on 1-(2-chloro-4-hydroxyphenyl)-3-cyclopropylurea is added at room temperature, and then the mixture is heated to from 55 to 75° C. while stirring for 20 hr. or longer to allow the reaction to proceed. To this reaction mixture, while heating at from 60 to 65° C. and stirring, a poor solvent (20 to 50% acetone in water or 20 to 50% 2-propanol in water) in a volume 15 times based on 1-(2-chloro-4-hydroxyphenyl)-3-cyclopropylurea is introduced within 8 min. so that crystals can appear. Further, it is preferred to add the seed crystals when the poor solvent is introduced to allow the crystals to appear. The polymorphic crystals (A') can be obtained by stirring the resulting reaction mixture, in which the crystals appeared, at the temperature ranging from room temperature to 40° C. generated by heating for 3 hr. or longer to collect the crystals by filtration.

The polymorphic crystals (B') can be obtained by a preparation process described below: 4-(3-chloro-4-(cyclopropylaminocarbonyl)aminophenoxy)-7-methoxy-6-quinolinecarboxamide is dissolved in an organic solvent, a good solvent (for example, DMSO, dimethylimidazolidine, 1-methyl-2-pyrrolidinone, N,N-dimethylformamide, N,N-dimethylacetamide, acetic acid, sulfolane, etc.), and then thereto a poor solvent (for example, water, acetone, acetonitrile, ethyl acetate, isopropyl acetate, methanol, ethanol, n-propanol, isopropanol, or a mixture thereof, etc.) is admixed slowly (for example, for 1 hr. or longer). When the poor solvent is admixed slowly, crystals appeared, but when stirring is stopped, the resultant crystals spreads all over the solvent.

More specifically, for example, to 4-(3-chloro-4-(cyclopropylaminocarbonyl)aminophenoxy)-7-methoxy-6-quinolinecarboxamide, a good solvent (DMSO or 1-methyl-2-pyrrolidinone) in a volume from 4 to 5 times based on 4-(3-chloro-4-(cyclopropylaminocarbonyl)aminophenoxy)-7-methoxy-6-quinolinecarboxamide is added, and then the mixture is heated to 80° C. or higher while stirring to dissolve the solute. To this mixture, while heating at from 65 to 85° C. and stirring, a poor solvent (isopropyl acetate, ethyl acetate, methanol, or isopropanol) in a volume from 10 to 20 times based on 4-(3-chloro-4-(cyclopropylaminocarbonyl)aminophenoxy)-7-methoxy-6-quinolinecarboxamide is introduced over 30 min. or longer so that crystals can appear. Further, it is preferred to add the seed crystals when the poor solvent is introduced to allow the crystals to appear. The polymorphic crystals (B') can be obtained by stirring the resulting reaction mixture, in which the crystals appeared, while heating at 70° C. or higher for 30 min. or longer, and further by stirring at room temperature to collect the crystals by filtration.

The polymorphic crystals (B') can be obtained by another preparation process described below: 4-(3-chloro-4-(cyclopropylaminocarbonyl)aminophenoxy)-7-methoxy-6-quinolinecarboxamide is dissolved while stirring in an organic solvent, a good solvent (for example, DMSO, dimethylimidazolidine, 1-methyl-2-pyrrolidinone, N,N-dimethylformamide, N,N-dimethylacetamide, acetic acid, sulfolane, etc.), and then a poor solvent (for example, water, acetone, acetonitrile, ethyl acetate, isopropyl acetate, methanol, ethanol, n-propanol, isopropanol, or a mixture thereof, etc.) is admixed so that when stirring is stopped, the resultant crystals spreads all over the solvent.

The polymorphic crystals (B') can be obtained by still another preparation process described below: 7-methoxy-4-chloroquinoline-6-carboxamide and 1-(2-chloro-4-hydroxyphenyl)-3-cyclopropylurea are reacted in the presence of a base (for example, potassium t-butoxide, cesium carbonate, potassium carbonate, etc.) in an organic solvent that works a good solvent for 4-(3-chloro-4-(cyclopropylaminocarbonyl) aminophenoxy)-7-methoxy-6-quinolinecarboxamide (for example, DMSO, dimethylimidazolidinone, 1-methyl-2-pyrrolidinone, N,N-dimethylformamide, N,N-dimethylacetamide, sulfolane, etc.), and then thereto a poor solvent (for example, water, acetone, acetonitrile, ethyl acetate, isopropyl acetate, methanol, ethanol, n-propanol, isopropanol, or a mixture thereof, etc.) is admixed slowly (for example, for 30 min. or longer).

More specifically, for example, to a mixture of 1-(2-chloro-4-hydroxyphenyl)-3-cyclopropylurea, 7-methoxy-4-chloroquinoline-6-carboxamide (one equivalent or more based on 1-(2-chloro-4-hydroxyphenyl)-3-cyclopropylurea), and potassium t-butoxide (one equivalent or more based on 1-(2-chloro-4-hydroxyphenyl)-3-cyclopropylurea), DMSO in a volume from 5 to 10 times based on 1-(2-chloro-4-hydroxyphenyl)-3-cyclopropylurea is added at room temperature, and then the mixture is heated to from 55 to 75° C. while stirring for 20 hr. or longer to allow the reaction to proceed. To this reaction mixture, while heating at from 60 to 65° C. and stirring, a poor solvent (33% acetone in water) in a volume 15 times based on 1-(2-chloro-4-hydroxyphenyl)-3-cyclopropylurea is introduced over 2 hr. or longer so that crystals can appear. The polymorphic crystals (B') can be obtained by stirring the resulting reaction mixture, in which the crystals appeared, while heating at 40° C. for 3 hr. or longer to collect the crystals by filtration.

The polymorphic crystals (B') can be obtained by still another preparation process described below: the polymorphic crystals (A') of 4-(3-chloro-4-(cyclopropylaminocarbonyl)aminophenoxy)-7-methoxy-6-quinolinecarboxamide having a diffraction peak at a diffraction angle (2θ±0.2°) of 15.75° in a powder X-ray diffraction is suspended and heated in a mixed solution of an organic solvent which is a good solvent for the above polymorphic crystals and a poor solvent for the above polymorphic crystals. It is preferred that the polymorphic crystals (A') used for this purpose also has diffraction peaks at diffraction angles (2θ±0.2°) of 9.98° and 11.01°.

The polymorphic crystals (B') can be obtained by still another preparation process described below: the polymorphic crystals (A') of 4-(3-chloro-4-(cyclopropylaminocarbonyl)aminophenoxy)-7-methoxy-6-quinolinecarboxamide having absorbance at a wavenumber of 3452.3±2.5 cm$^{-1}$ in an infrared absorption spectrum (potassium bromide) is suspended and heated in a mixed solution of a good solvent for the above polymorphic crystals and a poor solvent for the above polymorphic crystals. It is preferred that the polymorphic crystals (A') used for this purpose has absorbance at a wavenumber of 3452.3±2.5 cm$^{-1}$ (and also at 1712.2±1.0 cm$^{-1}$) in an infrared absorption spectrum (potassium bromide).

The crystals of hydrochloride or hydrobromide of 4-(3-chloro-4-(cyclopropylaminocarbonyl)aminophenoxy)-7-methoxy-6-quinolinecarboxamide; the crystals of p-toluenesulfonate or sulfate of the same; the crystals (A) of the same; the crystals (B) of the same; the crystals (C) of the same; the crystals of dimethyl sulfoxide solvate of methanesulfonate of the same; the crystals (F) of the same; the crystals (I) of the same; the crystals (α) of the same; the crystals (β) of the same; and the crystals of dimethyl sulfoxide solvate of ethanesulfonate of the same can be obtained by preparation processes described in the following paragraphs.

The crystals of hydrochloride or hydrobromide can be obtained by mixing the carboxamide and a solvent to dissolve the carboxamide therein, to which hydrochloric acid or hydrobromic acid is then added. More specifically, for example, the carboxamide and the solvent are mixed to dissolve the carboxamide therein by heating, and then thereto hydrochloric acid or hydrobromic acid is added followed by gradually cooling the resulting mixture to room temperature so that the crystals of hydrochloride or hydrobromide can be prepared. As a solvent, an alcohol such as methanol, ethanol, 1-propanol, and 2-propanol can be used, and ethanol is preferred. Further, water may be optionally added to the alcohol. There is no particular restriction on the amount of the solvent, but the solvent preferably from 10 to 30 times, more preferably 20 times, as much as the solute is used. As for the amount of hydrochloric acid or hydrobromic acid, from 1.0 to 1.5 equivalents, preferably 1.1 equivalents, based on the solute can be used. There is no particular restriction on the heating temperature, but the heating temperature is preferably from 60° C. to the reflux temperature, and more preferably the reflux temperature. For cooling, it may take from 10 min. to 24 hr. to cool down gradually from the heating temperature to room temperature.

The crystals of a p-toluenesulfonate or sulfate can be obtained by mixing the carboxamide, a solvent, and p-toluenesulfonic acid or sulfuric acid to dissolve the carboxamide therein. More specifically, for example, the carboxamide, the solvent, and p-toluenesulfonic acid or sulfuric acid are mixed to dissolve the carboxamide therein by heating followed by gradually cooling the resulting mixture to room temperature so that the crystals of p-toluenesulfonate or sulfate can be prepared. As a solvent, for example, dimethyl sulfoxide, N,N-dimethylformamide, N,N-dimethylacetamide, etc., can be used, and dimethyl sulfoxide is preferred. There is no particular restriction on the amount of the solvent, but the solvent preferably from 10 to 30 times, more preferably 20 times, as much as the solute is used. As for the amount of p-toluenesulfonic acid or sulfuric acid, from 1.0 to 1.5 equivalents, preferably 1.2 equivalents, based on the solute can be used. There is no particular restriction on the heating temperature, but the heating temperature is preferably from 60° C. to the reflux temperature, more preferably from 70 to 100° C., and still more preferably 80° C. For cooling, it may take from 10 min. to 24 hr. to cool down gradually from the heating temperature to room temperature.

The crystals (A) can be obtained by a preparation process comprising mixing 4-(3-chloro-4-(cyclopropylaminocarbonyl)aminophenoxy)-7-methoxy-6-quinolinecarboxamide, a solvent, and methanesulfonic acid to dissolve. More specifically, for example, the carboxamide, the solvent, and methanesulfonic acid are mixed to dissolve the carboxamide therein by heating followed by gradually cooling the resulting mixture to room temperature so that the crystals (A) of methanesulfonate can be prepared. As a solvent, for example, methanol, ethanol, 2-propanol, etc., can be used, and methanol is preferred. There is no particular restriction on the amount of the solvent, but the solvent preferably from 10 to 30 times, more preferably 20 times, as much as the solute is used. As for the amount of methanesulfonic acid, from 1.0 to 1.5 equivalents, preferably 1.2 equivalents, based on the solute can be used. There is no particular restriction on the heating temperature, but the heating temperature is preferably from 60° C. to the reflux temperature, and more preferably from 70 to 80° C. For cooling, it may take from 1 to 24 hr., preferably from 3 to 12 hr., to cool down gradually from the heating temperature to room temperature.

The crystals (A) can be also obtained by a preparation process comprising mixing 4-(3-chloro-4-(cyclopropylaminocarbonyl)aminophenoxy)-7-methoxy-6-quinolinecarboxamide, acetic acid, and methanesulfonic acid to dissolve. More specifically, for example, the carboxamide, acetic acid, and methanesulfonic acid are mixed to dissolve the carboxamide therein by heating, and then thereto a poor solvent is added followed by gradually cooling the resulting mixture to room temperature so that the crystals (A) of methanesulfonate can be prepared. Further, it is preferred to add the seed crystals (A) of methanesulfonate with the poor solvent. There is no particular restriction on the amount of acetic acid, but acetic acid preferably from 5 to 20 times, more preferably 10 times, as much as the solute is used. As for the amount of methanesulfonic acid, from 1.0 to 2.5 equivalents, preferably from 1.4 to 2.2 equivalents, based on the solute can be used. As a poor solvent, for example, methanol, ethanol, etc., can be used, and ethanol is preferred. There is no particular restriction on the amount of the poor solvent, but the poor solvent preferably from 10 to 30 times, more preferably 20 times, as much as the solute is used. Further, the poor solvent can be added at once, or divided into from 2 to 4 parts, preferably 2 parts, for addition. In such case, the amount ratio of the first addition and the second addition is from 1:1 to 3:1, and preferably 3:2. There is no particular restriction on the heating temperature, but the heating temperature is preferably from 50° C. to the reflux temperature, and more preferably 50° C. For cooling, it may take from 10 min. to 6 hr., preferably from 1 to 2 hr., to cool down gradually from the heating temperature to room temperature.

The crystals (B) can be obtained by a preparation process comprising drying (for example, by drying under aeration) the crystals (I) of acetic acid solvate of methanesulfonate of 4-(3-chloro-4-(cyclopropylaminocarbonyl)aminophenoxy)-7-methoxy-6-quinolinecarboxamide to remove acetic acid.

The crystals (C) can be obtained by a preparation process comprising heating crystals of dimethyl sulfoxide solvate of methanesulfonate of 4-(3-chloro-4-(cyclopropylaminocarbonyl)aminophenoxy)-7-methoxy-6-quinolinecarboxamide (and preferably cooling down gradually to room temperature). This preparation process can be conducted either in the presence of or in the absence of a solvent. When a solvent is used, as the solvent, for example, ethyl acetate, isopropyl acetate, n-butyl acetate, etc., can be used, and n-butyl acetate is preferred. There is no particular restriction on the heating temperature, but the heating temperature is preferably from 70° C. to the reflux temperature, and more preferably the reflux temperature.

The crystals (C) can be also obtained by a preparation process comprising mixing the crystals (I) of acetic acid solvate of methanesulfonate of 4-(3-chloro-4-(cyclopropylaminocarbonyl)aminophenoxy)-7-methoxy-6-quinolinecarboxamide and a solvent. In this preparation process, as a solvent, for example, an alcohol such as methanol, ethanol, and 2-propanol can be used, and ethanol is preferred. There is no particular restriction on the stirring temperature, but the stirring temperature is preferably from 20 to 60° C., and more preferably 40° C.

The crystals (C) can be still also obtained by a preparation process comprising mixing 4-(3-chloro-4-(cyclopropylaminocarbonyl)aminophenoxy)-7-methoxy-6-quinolinecarboxamide, acetic acid, and methanesulfonic acid to dissolve. More specifically, for example, the carboxamide, acetic acid, and methanesulfonic acid are mixed to dissolve the carboxamide therein by heating, and then thereto 2-propanol as a poor solvent is added followed by gradually cooling the resulting mixture to about 15° C. so that the crystals (C) of methanesulfonate can be prepared. Further, it is preferred to add the seed crystals (C) of methanesulfonate with the poor solvent and to add isopropyl acetate to accelerate the appearance of the crystals. There is no particular restriction on the amount of acetic acid, but acetic acid preferably from 5 to 10 times, more preferably from 7 to 8 times, as much as the solute is used. As for the amount of methanesulfonic acid, from 1.0 to 1.5 equivalents, preferably 1.2 equivalents, based on the solute can be used. There is no particular restriction on the amount of the poor solvent, but the poor solvent preferably from 2 to 10 times, more preferably from 4 to 5 times, as much as the solute is used. When isopropyl acetate is added, there is no particular restriction on the amount of isopropyl acetate, but isopropyl acetate preferably from 2 to 10 times, more preferably 5 times, as much as the solute is used. There is no particular restriction on the heating temperature, but the heating temperature is preferably 40° C. For cooling, it may take from 10 min. to 6 hr., preferably from 1 to 2 hr., to cool down gradually from the heating temperature to about 15° C.

In another preparation process wherein 4-(3-chloro-4-(cyclopropylaminocarbonyl)aminophenoxy)-7-methoxy-6-quinolinecarboxamide, acetic acid, and methanesulfonic acid are mixed to dissolve, the carboxamide, acetic acid, and methanesulfonic acid are mixed to dissolve the carboxamide therein at room temperature (or about 30° C.), and then thereto 2-propanol as a poor solvent is added followed by gradually cooling the resulting mixture to about 15° C. Resultant crystals are collected by filtration, and then the above crystals and a solvent are mixed and stirred so that the crystals (C) of methanesulfonate can be prepared. Further, it is preferred to add the seed crystals (C) of methanesulfonate with the poor solvent. There is no particular restriction on the amount of acetic acid, but acetic acid preferably from 5 to 20 times, more preferably 10 times, as much as the solute is used. As for the amount of methanesulfonic acid, from 1.0 to 2.5 equivalents, preferably from 1.8 to 2.2 equivalents, based on the solute can be used. There is no particular restriction on the amount of the poor solvent, but the poor solvent preferably from 10 to 30 times, more preferably 20 times, as much as the solute is used. For cooling, it may take from 10 min. to 4 hr., preferably from 30 min. to 2 hr., to cool down gradually from room temperature (or about 30° C.) to about 15° C. As a solvent to be mixed with the collected crystals, for example, an alcohol such as methanol, ethanol, and 2-propanol can be used, and ethanol is preferred.

In further still another process for preparing the crystals (C), the crystals (B) of methanesulfonate of 4-(3-chloro-4-(cyclopropylaminocarbonyl)aminophenoxy)-7-methoxy-6-quinolinecarboxamide is moisturized.

Crystals of dimethyl sulfoxide solvate of methanesulfonate can be obtained by mixing the carboxamide, dimethyl sulfoxide, and methanesulfonic acid to dissolve the carboxamide therein by heating, and then by adding thereto a poor solvent followed by cooling the resulting mixture to about 15° C. Further, it is preferred to add the seed crystals (A) of methanesulfonate with the poor solvent. There is no particular restriction on the amount of dimethyl sulfoxide, but dimethyl sulfoxide preferably from 5 to 20 times, more preferably from 8 to 10 times, as much as the solute is used. As for the amount of methanesulfonic acid, from 1.0 to 4.0 equivalents, preferably from 1.2 to 3.5 equivalents, based on the solute can be used. As a poor solvent, for example, ethyl acetate, isopropyl acetate, 1-propanol, 2-propanol, etc., can be used, and ethyl acetate and 2-propanol are preferred. There is no particular restriction on the amount of the poor solvent, but the poor solvent preferably from 10 to 30 times, more preferably 20 times, as much as the solute is used. Further, the poor solvent can be added at once, or divided into from 2 to 4 parts, preferably 2 parts, for addition. In such case, the amount ratio of the first addition and the second addition is from 1:1 to 1:5, and preferably 1:4. There is no particular restriction on the heating temperature, but the heating temperature is preferably from 50 to 100° C., and more preferably 60 to 80° C. For cooling, it may take from 10 min. to 6 hr., preferably from 1 to 2 hr., to cool down from the heating temperature to about 15° C.

The crystals (F) can be obtained by a preparation process comprising mixing 4-(3-chloro-4-(cyclopropylaminocarbonyl)aminophenoxy)-7-methoxy-6-quinolinecarboxamide, acetic acid, and methanesulfonic acid to dissolve. More specifically, for example, the carboxamide, acetic acid, and methanesulfonic acid are mixed to dissolve the carboxamide therein by heating, and then thereto a poor solvent is added followed by gradually cooling the resulting mixture to room temperature so that the crystals (F) of hydrate of methanesulfonate can be prepared. Further, it is preferred to add the seed crystals (A) of methanesulfonate with the poor solvent. There is no particular restriction on the amount of acetic acid, but acetic acid preferably from 5 to 20 times, more preferably 10 times, as much as the solute is used. As for the amount of methanesulfonic acid, from 1.0 to 2.0 equivalents, preferably from 1.3 to 1.6 equivalents, based on the solute can be used. As a poor solvent, for example, ethyl acetate and isopropyl acetate can be used, and ethyl acetate is preferred. There is no particular restriction on the amount of the poor solvent, but the poor solvent preferably from 10 to 30 times, more preferably 20 times, as much as the solute is used. Further, the poor solvent can be added at once, or divided into from 2 to 4 parts, preferably 2 parts, for addition. In such case, the amount ratio of the first addition and the second addition is from 1:1 to 1:5, and preferably 1:3. There is no particular restriction on the heating temperature, but the heating temperature is preferably from 40 to 60° C., and more preferably 50° C. For cooling, it may take from 10 min. to 6 hr., preferably from 2 to 4 hr., to cool down gradually from the heating temperature to room temperature.

The crystals (I) can be obtained by a preparation process comprising mixing 4-(3-chloro-4-(cyclopropylaminocarbonyl)aminophenoxy)-7-methoxy-6-quinolinecarboxamide, acetic acid, and methanesulfonic acid to dissolve. More specifically, for example, the carboxamide, acetic acid, and methanesulfonic acid are mixed to dissolve the carboxamide therein by heating, and then thereto a poor solvent is added followed by gradually cooling the resulting mixture to room temperature so that the crystals (I) of an acetic acid solvate of methanesulfonate can be prepared. Further, it is preferred to add the seed crystals (C) of methanesulfonate with the poor solvent and to add isopropyl acetate to accelerate the appearance of the crystals. There is no particular restriction on the amount of acetic acid, but acetic acid preferably from 5 to 10 times, more preferably from 7 to 8 times, as much as the solute is used. As for the amount of methanesulfonic acid, from 1.0 to 1.5 equivalents, preferably 1.2 equivalents, based on the solute can be used. As a poor solvent, for example, 1-propanol 1-butanol, tert-butanol, etc., can be used, and 1-propanol is preferred. There is no particular restriction on the amount of the poor solvent, but the poor solvent preferably from 5 to 20 times, more preferably from 8 to 10 times, as much as the solute is used. Further, the poor solvent can be added at once, or divided into from 2 to 4 parts, preferably 2 parts, for addition. In such case, the amount ratio of the first addition and the second addition is from 1:1 to 1:5, and preferably 1:3.5. When isopropyl acetate is added, there is no particular restriction on the amount of isopropyl acetate, but isopropyl acetate preferably from 2 to 10 times, more preferably 5 times, as much as the solute is used. There is no particular restriction on the heating temperature, but the heating temperature is preferably 40° C. For cooling, it may take from 10 min. to 6 hr., preferably from 1 to 2 hr., to cool down gradually from the heating temperature to room temperature.

The crystals (α) can be obtained by a preparation process comprising mixing 4-(3-chloro-4-(cyclopropylaminocarbonyl)aminophenoxy)-7-methoxy-6-quinolinecarboxamide, a solvent, and ethanesulfonic acid to dissolve. More specifically, for example, the carboxamide, the solvent, and ethanesulfonic acid are mixed to dissolve the carboxamide therein by heating, and then thereto a poor solvent is added followed by gradually cooling the resulting solution to room temperature so that the crystals (α) of ethanesulfonate can be prepared. As a solvent, for example, dimethyl sulfoxide, etc., can be used. There is no particular restriction on the amount of the solvent, but the solvent preferably from 5 to 20 times, more preferably 10 times, as much as the solute is used. As for the amount of ethanesulfonic acid, from 1.0 to 1.5 equivalents, preferably 1.2 equivalents, based on the solute can be used. As a poor solvent, for example, ethyl acetate, etc., can be used. There is no particular restriction on the amount of the poor solvent, but the poor solvent preferably from 5 to 20 times, more preferably 10 times, as much as the solute is used. There is no particular restriction on the heating temperature, but the heating temperature is preferably from 50 to 70° C., and more preferably 60° C. For cooling, it may take from 10 min. to 24 hr., preferably from 1 to 2 hr., to cool down gradually from the heating temperature to room temperature.

The crystals (β) can be obtained by a preparation process comprising mixing the crystals (α) of ethanesulfonate of 4-(3-chloro-4-(cyclopropylaminocarbonyl)aminophenoxy)-7-methoxy-6-quinolinecarboxamide and a solvent. As a solvent, for example, methanol, ethanol, 2-propanol, etc., can be used, and ethanol is preferred. There is no particular restriction on the amount of the solvent, but the solvent preferably from 5 to 20 times, more preferably 10 times, as much as the solute is used. There is no particular restriction on the amount of water, but water preferably from 1/10 to 1/2 times, more preferably 1/6 times, as much as ethanol is used.

The crystals (β) can be also obtained by a preparation process comprising mixing 4-(3-chloro-4-(cyclopropylaminocarbonyl)aminophenoxy)-7-methoxy-6-quinolinecarboxamide, acetic acid, and ethanesulfonic acid to dissolve. More specifically, for example, the carboxamide, acetic acid, and ethanesulfonic acid are mixed to dissolve the carboxamide therein by heating, and then thereto a poor solvent and water are added followed by cooling the resulting mixture to 0° C. so that the crystals (β) of a hydrate of ethanesulfonate can be prepared. Further, it is preferred to add the seed crystals (β) of ethanesulfonate with the poor solvent. There is no particular restriction on the amount of acetic acid, but acetic acid preferably from 2.5 to 10 times, more preferably 5 times, as much as the solute is used. As for the amount of ethanesulfonic acid, from 1.0 to 1.5 equivalents, preferably 1.2 equivalents, based on the solute can be used. As a poor solvent, for example, ethanol, 2-propanol, etc., can be used, and 2-propanol is preferred. There is no particular restriction on the amount of the poor solvent, but the poor solvent preferably from 10 to 40 times, more preferably 30 times, as much as the solute is used. Further, the poor solvent can be added at once, or divided into from 2 to 4 parts, preferably 2 parts, for addition. In such case, the amount ratio of the first addition and the second addition is from 1:1 to 1:5, and preferably from 1:1.5 to 1:2. There is no particular restriction on the amount of water, but water preferably from 1/10 to 1/30 times, more preferably 1/20 times, as much as the poor solvent is used. There is no particular restriction on the heating temperature, but the heating temperature is preferably from 50 to 70° C., and more preferably 60° C. For cooling, it may take from 10 min. to 6 hr., preferably from 2 to 4 hr., to cool down from the heating temperature to 0° C.

Crystals of dimethyl sulfoxide solvate of ethanesulfonate can be obtained by mixing the carboxamide, dimethyl sulfoxide, and ethanesulfonic acid to dissolve the carboxamide therein by heating, and then by adding a poor solvent thereto followed by cooling the resulting solution to 0° C. Further, it is preferred to add the seed crystals (β) of ethanesulfonate with the poor solvent. There is no particular restriction on the amount of dimethyl sulfoxide, but dimethyl sulfoxide preferably from 5 to 20 times, more preferably 10 times, as much as the solute is used. As for the amount of ethanesulfonic acid, from 1.0 to 1.5 equivalents, preferably 1.2 equivalents, based on the solute can be used. As a poor solvent, for example, ethyl acetate, etc., can be used. There is no particular restriction on the amount of the poor solvent, but the poor solvent preferably from 5 to 20 times, more preferably 10 times, as much as the solute is used. Further, the poor solvent can be added at once, or divided into from 2 to 4 parts, preferably 2 parts, for addition. In such case, the amount ratio of the first addition and the second addition is from 1:1 to 3:1, and preferably 3:2. There is no particular restriction on the heating temperature, but the heating temperature is preferably from 50 to 70° C., and more preferably 60° C. For cooling, it may take from 10 min. to 6 hr., preferably from 1 to 2 hr., to cool down from the heating temperature to 0° C.

(Pharmaceutical Composition)

The pharmaceutical composition in accordance with the present invention comprises: in addition to the active ingredient consisting of the compound represented by Formula (1), salt thereof, or solvate of the foregoing, as described above;

(i) a compound, a 5% (w/w) aqueous solution or suspension of which has a pH of 8 or more; and/or (ii) silicic acid, salt thereof, or solvate of the foregoing.

Further, the compound whose pH of a 5% (w/w) aqueous solution or suspension thereof is 8 or more contributes to the suppression of the decomposition of the active ingredient under humidified and heated storage conditions, and hence hereinafter is referred to as the "stabilizer." Moreover, silicic acid, salt thereof, or solvate of the foregoing contributes to the inhibition of the gelation of the pharmaceutical composition, and hence hereinafter is referred to as the "gelation inhibitor."

As the stabilizer, magnesium oxide, calcium oxide, sodium carbonate, disodium hydrogenphosphate, sodium citrate, dipotassium hydrogenphosphate, sodium acetate, sodium hydrogencarbonate, and sodium hydroxide are preferred. Of these, magnesium oxide and calcium oxide are particularly preferred in view of an increase in weight and coloration. The amount of the stabilizer to add to the pharmaceutical composition is preferably from 0.5 to 15, more preferably from 1 to 10, and most preferably from 1 to 5 mass parts based on 100 mass parts of the pharmaceutical composition.

As the gelation inhibitor, light anhydrous silicic acid, silicon dioxide hydrate, calcium silicate, magnesium silicate, magnesium aluminosilicate, magnesium aluminometasilicate, magnesium aluminum silicate, synthetic aluminum silicate, and hydrous silicic dioxide are preferred. Of these, light anhydrous silicic acid, silicon dioxide hydrate, and calcium silicate are more preferred, and light anhydrous silicic acid and silicon dioxide hydrate are most preferred. The amount of the gelation inhibitor to add to the pharmaceutical composition is preferably from 4 to 20, and more preferably from 8 to 20 mass parts based on 100 mass parts of the pharmaceutical composition.

In the pharmaceutical composition in accordance with the present invention, in addition to the active ingredient consisting of the compound represented by Formula (1), salt thereof, or solvate of the foregoing, the stabilizer, and the gelation inhibitor; additives such as a diluent, a binder, a lubricant, a disintegrant, a coloring agent, a flavoring agent, an emulsifier, a surfactant, a solubilizing agent, a suspending agent, an isotonizing agent, a buffer, a preservative, an antioxidant, a stabilizing agent, and an absorption promoter can be added thereto.

Examples of diluents include lactose, sucrose, glucose, cornstarch, mannitol, sorbitol, starch, alpha starch, dextrin, crystalline cellulose, light anhydrous silicic acid, aluminum silicate, calcium silicate, magnesium aluminometasilicate, calcium hydrogenphosphate, etc.

Examples of binders include polyvinyl alcohol, methylcellulose, ethylcellulose, gum Arabic, tragacanth, gelatin, shellac, hydroxypropylmethylcellulose, hydroxypropylcellulose, sodium carboxymethylcellulose, polyvinylpyrrolidone, Macrogol, etc.

Examples of lubricants include magnesium stearate, calcium stearate, sodium stearyl fumarate, talc, polyethylene glycol, colloidal silica, etc.

Examples of disintegrants include crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium, carmellose, carmellose sodium, crospovidone, low-substituted carboxymethyl starch sodium, partially alpha starch, etc. The amount of the disintegrant to add to the pharmaceutical composition is preferably from 0.1 to 30, and more preferably from 1 to 20 mass parts based on 100 mass parts of the pharmaceutical composition.

As the disintegrant, low-substituted hydroxypropylcellulose, carboxymethyl starch sodium, carmellose sodium, carmellose calcium, croscarmellose sodium, crospovidone, and partially alpha starch are preferred. Low-substituted hydroxypropylcellulose, carmellose calcium, croscarmellose sodium, crospovidone, and partially alpha starch are more preferred. Croscarmellose sodium is most preferred.

Examples of coloring agents include iron sesquioxide, yellow iron sesquioxide, carmine, caramel, beta-carotene, titanium oxide, talc, riboflavin sodium phosphate, yellow aluminum lake, etc, which have been approved as additives for medicaments.

Flavoring agents include cocoa powder, menthol, aromatic powder, mentha oil, borneol, powdered cinnamon bark, etc.

Examples of emulsifiers or surfactants include stearyl triethanolamine, sodium lauryl sulfate, lauryl aminopropionic acid, lecithin, glycerin monostearate, sucrose fatty acid ester, glycerin fatty acid ester, etc.

Examples of solubilizers include polyethylene glycol, propylene glycol, benzyl benzoate, ethanol, cholesterol, triethanolamine, sodium carbonate, sodium citrate, Polysorbate 80, nicotinamide, etc.

Examples of suspending agents include, in addition to the above surfactants, hydrophilic polymers such as polyvinyl alcohol, polyvinylpyrrolidone, methylcellulose, hydroxymethylcellulose, hydroxyethylcellulose, and hydroxypropylcellulose.

Examples of isotonizing agent include glucose, sodium chloride, mannitol, sorbitol, etc.

Examples of buffers include buffer solutions of phosphate, acetate, carbonate, citrate, etc.

Examples of preservatives include methylparaben, propylparaben, chlorobutanol, benzyl alcohol, phenethyl alcohol, dehydroacetic acid, sorbic acid, etc.

Examples of antioxidants include sulfite, ascorbic acid, alpha-tocopherol, etc.

Further, the pharmaceutical composition can be formulated into oral preparations such as tablets, powders, granules, capsules, syrups, troches, and inhalants; external preparations such as suppositories, ointments, ophthalmic ointments, tapes, eye drops, nasal drops, ear drops, cataplasms, and lotions; or injections. Oral preparations are formulated by combining the above additives as desired. Moreover, optionally surface of these oral preparations may be coated.

External preparations are formulated by combining, among the above described additives, in particular, the diluent, the binder, the flavoring agent, the emulsifier, the surfactant, the solubilizer, the suspending agent, the isotonizing agent, the preservative, the antioxidant, the stabilizing agent, and the absorption promoter, as desired. Injections are formulated by combining, among the above described additives, in particular, the emulsifier, the surfactant, the solubilizer, the suspending agent, the isotonizing agent, the buffer, the preservative, the antioxidant, the stabilizing agent, and the absorption promoter, as desired.

The pharmaceutical composition in accordance with the present invention can be prepared by a well-known method. For example, to prepare tablets, a preparation process comprising steps of pre-mixing, granulating, drying, milling, main-mixing, compression, coating, and screening in this order can be applied. Either wet granulation (a non-aqueous system is preferred) or dry granulation may be employed.

In the pre-mixing step, a diluent and a binder are mixed, for example, in a 20 L super mixer. In the granulating step, to the resulting mixture, the active ingredient and an organic solvent such as ethanol are added, which are then granulated, for example, in a 20 L super mixer. In the drying step, the resulting granules are dried in a tray dryer, etc. The milling step is then conducted by a power mill, etc. To the milled granules, a disintegrant and a lubricant are added, and the main mixing step is conducted, for example, in a 10/20 L tumbler mixer, etc. Then, the compression step is conducted by a tablet press. Finally, the screening step is conducted to obtain the pharmaceutical composition (tablets).

Further, before the addition of a diluent and a binder in the pre-mixing step, another pre-mixing step wherein the active ingredient and the gelation inhibitor are added in advance can be performed. In such case, in the granulating step, only an organic solvent such as ethanol will be added. Moreover, between the coating step and the screening step, a mixing step in a 5 L tumbler mixer, etc., may be performed.

The dosage of the pharmaceutical composition in accordance with the invention depends on symptoms, age, and dosage forms, but in general, in terms of the active ingredient, from 100 μg to 10 g thereof is administered daily once or in a few divided portions to an adult.

The pharmaceutical composition in accordance with the present invention is extremely useful as an angiogenic inhibitor, and is effective as an agent to prevent or treat diseases against which angiogenic inhibition is effective, an angiogenic inhibitor, an anti-tumor agent, an agent to treat angioma, a cancer metastasis inhibitor, an agent to treat retinal angiogenesis, an agent to treat diabetic retinopathy, an agent to treat inflammatory diseases, an agent to treat inflammatory diseases selected from the group consisting of osteoarthritis, rheumatic arthritis, psoriasis, and delayed hyperactivity, and an agent to treat atherosclerosis.

Further, when the pharmaceutical composition in accordance with the present invention is used as an anti-tumor agent, the target tumor thereof is, for example, pancreatic cancer, stomach cancer, colorectal cancer, breast cancer, prostate cancer, lung cancer, renal cancer, brain tumor, blood cancer, or ovarian cancer. In particular, stomach cancer, colorectal cancer, prostate cancer, or renal cancer is a preferred target.

Moreover, the pharmaceutical composition in accordance with the present invention exhibits a potent c-Kit kinase inhibitory action, and hence is useful as an anti-tumor agent against tumors exacerbated by activated c-Kit kinase (acute myeloid leukemia, mast cell leukemia, small cell lung cancer, GIST, testicular tumor, ovarian cancer, breast cancer, brain tumor, neuroblastoma, and colorectal cancer). The pharmaceutical composition in accordance with the present invention is also useful as an agent to treat diseases such as mastocytosis in which the involvement of c-Kit kinase is suspected, allergies, and asthma.

EXAMPLES

The present invention is further explained in detail by referring to examples and comparative examples in the following paragraphs. However, the present invention shall not be limited by the following examples by any means.

Preparation of Medicament (Active Ingredient)

Preparation Example 1

Preparation (1) of 4-(3-chloro-4-(cyclopropylaminocarbonyl)aminophenoxy)-7-methoxy-6-quinolinecarboxamide Phenyl N-(4-(6-carbamoyl-7-methoxy-4-quinolyl)oxy-2-chlorophenyl)carbamate (17.5 g, 37.7 mmol) disclosed in WO 02/32872 was dissolved in N,N-dimethylformamide (350 mL), and then cyclopropylamine (6.53 mL, 94.25 mmol) was added to the reaction mixture under a nitrogen atmosphere, followed by stirring overnight at room temperature. To the mixture was added water (1.75 L), and the mixture was stirred. Precipitated crude crystals were collected by filtration, washed with water, and dried at 70° C. for 50 min. To the obtained crude crystals was added ethanol (300 mL), and then the mixture was heated under reflux for 30 min to dissolve, followed by stirring overnight to cool slowly down to room temperature. Precipitated crystals was collected by filtration and dried under vacuum, and then further dried at 70° C. for 8 hours to give the titled crystals (12.91 g; 80.2%).

Preparation Example 2

Preparation (2) of 4-(3-chloro-4-(cyclopropylaminocarbonyl)aminophenoxy)-7-methoxy-6-quinolinecarboxamide (1) Preparation of phenyl N-(2-chloro-4-hydroxyphenyl)carbamate

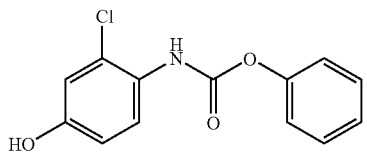

[Formula 3]

To a suspension of 4-amino-3-chlorophenol (23.7 g) in N,N-dimethylformamide (100 mL) was added pyridine (23.4 mL) while cooling in an ice bath, and phenyl chloroformate (23.2 mL) was added dropwise below 20° C. After stirring at room temperature for 30 min, water (400 mL), ethyl acetate (300 mL), and 6N—HCl (48 mL) were added and stirred. The organic layer was separated, washed twice with a 10% aqueous sodium chloride solution (200 mL), and dried over magnesium sulfate. The solvent was evaporated to give 46 g of the titled compound as a solid.

$^1$H-NMR Spectrum (CDCl$_3$) δ(ppm): 5.12 (1 h, br s), 6.75 (1H, dd, J=9.2, 2.8 Hz), 6.92 (1H, d, J=2.8 Hz), 7.18-7.28 (4H, m), 7.37-7.43 (2H, m), 7.94 (1H, br s)

(2) Preparation of 1-(2-chloro-4-hydroxyphenyl)-3-cyclopropylurea

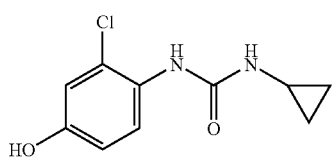

[Formula 4]

To a solution of phenyl N-(2-chloro-4-hydroxyphenyl)carbamate in N,N-dimethylformamide (100 mL) was added cyclopropylamine (22.7 mL) while cooling in an ice bath, and the stirring was continued at room temperature overnight. Water (400 mL), ethyl acetate (300 mL), and 6N—HCl (55 mL) were added thereto, and the mixture was stirred. The organic layer was then separated, washed twice with a 10% aqueous sodium chloride solution (200 mL), and dried over magnesium sulfate. The solvent was evaporated to give prism crystals, which were collected by filtration and washed with heptane to give 22.8 g of the titled compound (yield from 4-amino-3-chlorophenol: 77%).

$^1$H-NMR Spectrum (CDCl$_3$) δ(ppm): 0.72-0.77 (2H, m), 0.87-0.95 (2H, m), 2.60-2.65 (1H, m), 4.89 (1H, br s), 5.60 (1H, br s), 6.71 (1H, dd, J=8.8, 2.8 Hz), 6.88 (1H, d, J=2.8 Hz), 7.24-7.30 (1H, br s), 7.90 (1H, d, J=8.8H)

(3) Preparation of 4-(3-chloro-4-(cyclopropylaminocarbonyl)aminophenoxy)-7-methoxy-6-quinolinecarboxamide To dimethyl sulfoxide (20 mL) were added 7-methoxy-4-chloroquinoline-6-carboxamide (0.983 g), 1-(2-chloro-4-hydroxyphenyl)-3-cyclopropylurea (1.13 g) and cesium carbonate (2.71 g), and the mixture was heated and stirred at 70° C. for 23 hours. The reaction mixture was cooled to room temperature, and water (50 mL) was added, and the resultant crystals were then collected by filtration to give 1.56 g of the titled compound (yield: 88%).

Preparation Example 3

Preparation (3) of 4-(3-chloro-4-(cyclopropylaminocarbonyl)aminophenoxy)-7-methoxy-6-quinolinecarboxamide 7-Methoxy-4-chloroquinoline-6-carboxamide (5.00 kg, 21.13 mol), dimethyl sulfoxide (55.05 kg), 1-(2-chloro-4-hydroxyphenyl)-3-cyclopropylurea (5.75 kg, 25.35 mol) and potassium t-butoxide (2.85 kg, 25.35 mol) were introduced in this order into a reaction vessel under a nitrogen atmosphere. The mixture was stirred for 30 min at 20° C., and the temperature was raised to 65° C. over 2.5 hours. The mixture was stirred at the same temperature for 19 hours. 33% (v/v) acetone-water (5.0 L) and water (10.0 L) were added dropwise over 3.5 hours. After the addition was completed, the mixture was stirred at 60° C. for 2 hours. 33% (v/v) acetone-water (20.0 L) and water (40.0 L) were added dropwise at 55° C. or more over 1 hour. After stirring at 40° C. for 16 hours, precipitated crystals were collected by filtration using a nitrogen pressure filter, and was washed with 33% (v/v) acetone-water (33.3 L), water (66.7 L), and acetone (50.0 L) in that order. The obtained crystals were dried at 60° C. for 22 hours using a conical vacuum dryer to give 7.78 kg of the titled compound (yield: 96.3%).

Further, all of the $^1$H-NMR chemical sift values of 4-(3-chloro-4-(cyclopropylaminocarbonyl)aminophenoxy)-7-methoxy-6-quinolinecarboxamide prepared in Preparation Examples 1 to 3 described above agreed with those of 4-(3-chloro-4-(cyclopropylaminocarbonyl)aminophenoxy)-7-methoxy-6-quinolinecarboxamide described in WO 02/32872.

Stability Evaluation of Medicament

The crystals (C) (hereinafter, referred to as the "medicament Y") of methanesulfonate of 4-(3-chloro-4-(cyclopropylaminocarbonyl)aminophenoxy)-7-methoxy-6-quinolinecarboxamide (the "medicament X") synthesized in the above "Preparation of Medicament (Active Ingredient)" was combined with the following 10 compounds (that exhibit various pH values when 5% (w/w) aqueous solutions or suspensions were made therewith. In the table, pH values thereof are shown). Stability of the medicament X therewith was evaluated.

TABLE 1

| | pH value of 5% (w/w) aqueous solution or suspension |
|---|---|
| Magnesium oxide (MgO, Tomita Pharmaceutical Co., Ltd.) | 10.63 |
| Sodium carbonate ($Na_2CO_3$, Wako Pure Chemical Industries, Ltd.) | 11.45 |
| Disodium hydrogenphosphate ($Na_2HPO_4$, Kanto Chemical Co., Inc.) | 9.26 |
| Sodium citrate (Sodium citrate, Kozakai Pharmaceutical Co., Ltd.) | 8.22 |
| Dipotassium hydrogenphosphate ($K_2HPO_4$, Wako Pure Chemical Industries, Ltd.) | 9.11 |
| Sodium acetate (Sodium acetate, Wako Pure Chemical Industries, Ltd.) | 8.46 |
| Sodium hydrogencarbonate ($NaHCO_3$, Wako Pure Chemical Industries, Ltd.) | 8.15 |
| Sodium hydroxide (NaOH, Wako Pure Chemical Industries, Ltd.) | 13.56 |
| Glycine (Glycine, Ajinomoto Co., Inc.) | 6.17 |
| δ-Gluconolactone (δ-Gluconolactone, Kanto Chemical Co., Inc.) | 2.40 |

Anhydrous dibasic calcium phosphate (a diluent, from Kyowa Chemical Industry Co., Ltd.), croscarmellose sodium (a disintegrant, trade name: Ac-Di-Sol, from FMC International Inc.), hydroxypropylcellulose (a binder, trade name: HPC-L, from Nippon Soda Co., Ltd.), and the medicament Y are mixed in a ratio of 10/2.3/3/0.19 (w/w/w/w). To the resulting mixture, water was added, which then underwent the mixing/wet granulation process in a tablet mill followed by drying at 60° C. for 5 hr. to give the pellets.

Approximately 50 mg of each of stabilizers, magnesium oxide (MgO), sodium carbonate ($Na_2CO_3$), disodium hydrogenphosphate ($Na_2HPO_4$), sodium citrate, dipotassium hydrogenphosphate ($K_2HPO_4$), sodium acetate, sodium hydrogencarbonate ($NaHCO_3$), sodium hydroxide (NaOH), glycine, and δ-gluconolactone was combined together to grind in a mortar, with which approximately 500 mg of the above pellets were kneaded in a mortar. To the resulting mixture, 50 L of water was added and mixed further.

The prepared mixture was divided into about 100 mg in 2 PP tubes, which were then stressed for a week under the conditions of 60° C./open and under the conditions of 60° C./75% relative humidity/open (hereinafter, relative humidity is abbreviated as "RH", and "open" refers to conditions wherein an open tube is heated and humidified). To the stressed mixture, 8 mL of an extractant was added, which then underwent sonication. The resulting suspension was centrifuged to give the supernatant as a sample solution, which then was analyzed by HPLC. The results are shown in Table 2. In Table 2, the results from the one with no stabilizer are also shown.

TABLE 2

| Additive | 60° C./open, 1 week | | 60° C./75% RH/open, 1 week | |
|---|---|---|---|---|
| | HPLC purity (%) | Decomposed product A (%) | HPLC purity (%) | Decomposed product A (%) |
| No additive | 97.0 | 0.40 | 95.6 | 1.63 |
| MgO | 97.4 | 0.08 | 97.2 | 0.06 |
| $Na_2CO_3$ | 97.6 | 0.06 | 97.3 | 0.12 |
| $Na_2HPO_4$ | 97.5 | 0.06 | 97.5 | 0.08 |
| δ-Gluconolactone | 97.9 | 0.10 | 95.6 | 1.88 |
| Sodium citrate | 97.6 | 0.10 | 97.6 | 0.09 |
| $K_2HPO_4$ | 97.4 | 0.06 | 97.4 | 0.08 |
| Sodium acetate | 97.6 | 0.08 | 97.4 | 0.21 |
| Glycine | 97.0 | 0.15 | 92.3 | 1.38 |
| $NaHCO_3$ | 97.5 | 0.11 | 97.3 | 0.10 |
| NaOH | 97.5 | 0.06 | 97.4 | 0.06 |

The relationship between the pH value of a 5% (w/w) aqueous solution or suspension of each stabilizer and the decomposed product A (see the chemical formula described above) is also shown in FIG. 1. These results demonstrate that when the pH value of a 5% (w/w) aqueous solution or suspension of the stabilizer is 8 or more, the decomposition can be significantly reduced.

Preparation of Pharmaceutical Composition

Example 1

10 mg Tablets Containing Magnesium Oxide

In a 1 L super mixer 2.5 g of the medicament Y, 10 g of magnesium oxide (a stabilizer, from Tomita Pharmaceutical Co., Ltd.), 48.5 g of D-mannitol (a diluent, from Towa Chemical Industry Co., Ltd.), 10 g of partially alpha starch (a disintegrant, trade name: PCS (pharmaceutical grade), from Asahi Kasei Corporation), 22.5 g of crystalline cellulose (a diluent, trade name: Avicel PH101, from Asahi Kasei Corporation), and 3 g of hydroxypropylcellulose (a binder, trade name: HPC-L, from Nippon Soda Co., Ltd.) were mixed. Then thereto a suitable amount of purified water was added followed by granulation, drying, and milling to give the granules. To these granules, 3 g of croscarmellose sodium (a disintegrant, trade name: Ac-Di-Sol, from FMC International Inc.) and 0.5 g of magnesium stearate (a lubricant) were admixed, and then tablets were formed by a tablet press to give tablets (the total mass per tablet was 400 mg) containing 10 mg of the medicament Y per tablet.

Comparative Example 1

10 mg Tablets Containing No Magnesium Oxide

In a 1 L super mixer 2.5 g of the medicament Y, 10 g of calcium hydrogenphosphate (a diluent), 48.5 g of D-mannitol (a diluent, from Towa Chemical Industry Co., Ltd.), 110 g of partially alpha starch (a disintegrant, trade name: PCS (pharmaceutical grade), from Asahi Kasei Corporation), 22.5 g of crystalline cellulose (a diluent, trade name: Avicel PH101, from Asahi Kasei Corporation), and 3 g of hydroxypropylcellulose (a binder, trade name: HPC-L, from Nippon Soda Co., Ltd.) were mixed. Then thereto a suitable amount of purified water was added followed by granulation, drying, and milling to give the granules. To these granules, 3 g of croscarmellose sodium (a disintegrant, trade name: Ac-Di-Sol, from FMC International Inc.) and 0.5 g of magnesium stearate (a lubricant) were admixed, and then tablets were formed by a tablet press to give tablets (the total mass per tablet was 400 mg) containing 10 mg of the medicament Y per tablet.

Stability was tested for the tablets prepared in Example 1 and Comparative Example 1. In the test, after the tablets were stored at 5° C., at 25° C., and at 40° C. and under relative humidity 75% RH, for 3 months each, impurity levels (%) were determined by HPLC. The results are shown in Table 3 below. As shown in Table 3, the tablets containing magnesium oxide (MgO) (Example 1) are superior in stability to the tablets containing no magnesium oxide (MgO) (Comparative Example 1). In particular, the stability under the humidified conditions was remarkably improved with the stabilizer.

TABLE 3

| Storage conditions | Example 1 | Comparative Example 1 |
|---|---|---|
| 5° C./3 Months | 0 | 0 |
| 25° C./3 Months | 0 | 0.17 |
| 40° C. · 75% RH/3 Months | 0 | 1.58 | values: impurity levels (%) determined by HPLC

Further, the ability of decomposition suppression was examined for magnesium oxide, disodium hydrogenphosphate, sodium hydrogencarbonate, and sodium hydroxide.

A placebo tablet containing 8.0 mg of light anhydrous silicic acid (trade name: AEROSIL (registered trademark) 200, from Nippon Aerosil Co., Ltd.), 52.5 mg of D-mannitol (from Towa Chemical Industry Co., Ltd.), 30.0 mg of crystalline cellulose (trade name: Avicel PH101, from Asahi Kasei Corporation), 3.0 mg of hydroxypropylcellulose (trade name: HPC-L, from Nippon Soda Co., Ltd.), 5.0 mg of croscarmellose sodium (trade name: Ac-Di-Sol, from FMC International Inc.), 1.5 mg of sodium stearyl fumarate (from JRS Pharma LP), and 5.0 mg of opadry yellow was prepared according to an ordinary method. Approximately 30 g of the placebo tablets were ground in a tablet mill, to which then about 33 mg of the medicament Y was added. By repetitive mixing of the medicament Y with the ground placebo tablets, $\frac{1}{1000}$ diluted powder (0.1%) was obtained.

Approximately 100 mg of each of stabilizers (magnesium oxide, disodium hydrogenphosphate, sodium hydrogencarbonate, and sodium hydroxide) was mixed with 1,900 mg of the 0.1% powder in a mortar to prepare a powder containing a 5% stabilizer. Likewise, a powder containing a 4, 3, 2, or 1% stabilizer was prepared.

Figure 6:
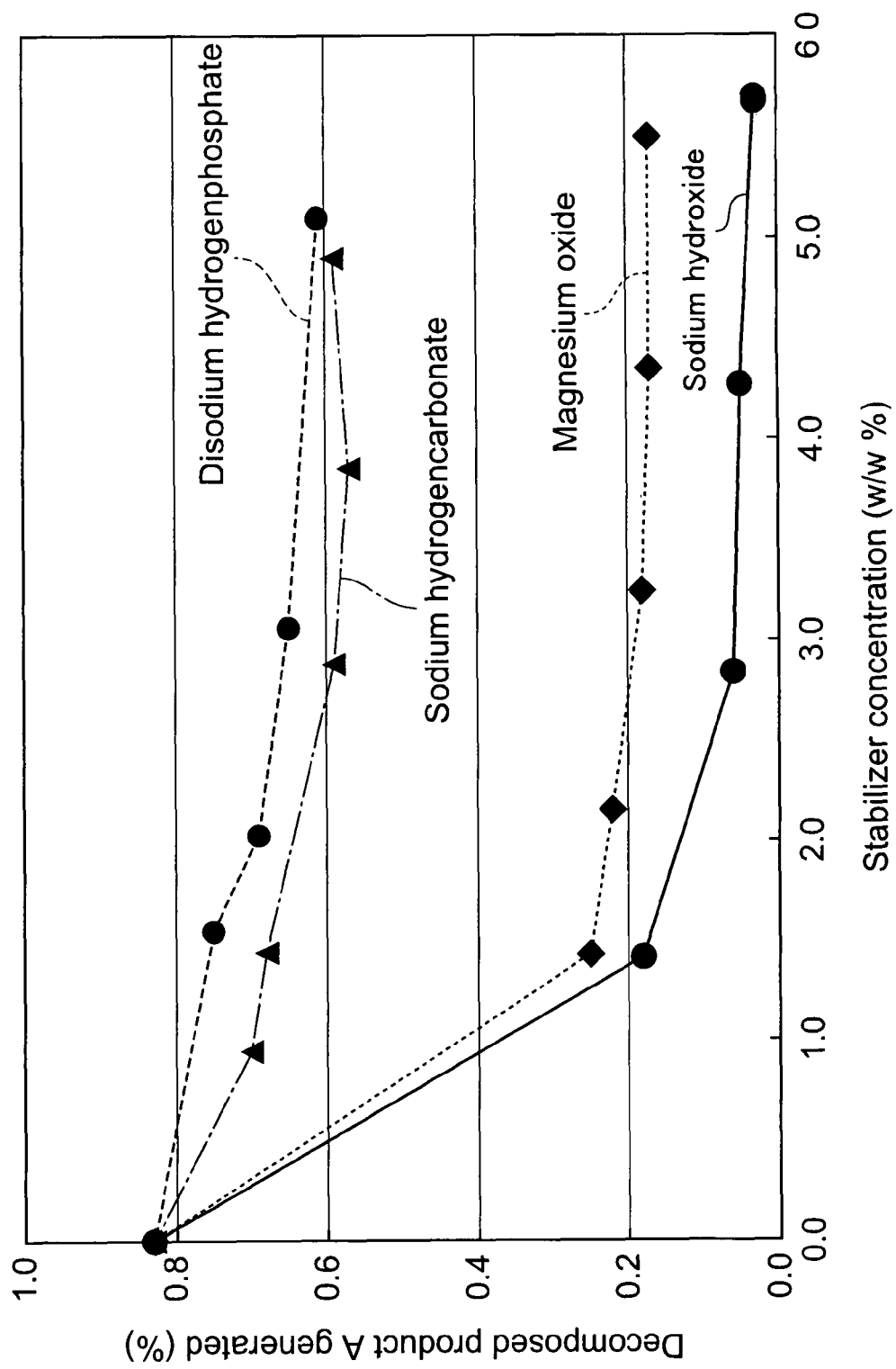
FIG. 6 is a graph illustrating the amount of the decomposed product A generated when various kinds of stabilizers were added at various concentrations.

In a glass vial, approximately 200 mg of each of the prepared mixtures (0.2 mg of the medicament X is contained) was stored and stressed under the conditions of 65° C./75% RH/open for a week. To the stressed mixture, 5 mL of an extractant was added, which then underwent sonication. The resulting suspension was centrifuged to give the supernatant as a sample solution, which then was analyzed by HPLC. The results are shown in FIG. 6. FIG. 6 is a graph illustrating the amount of the decomposed product A generated when various kinds of stabilizers were added at various concentrations. The results demonstrate that sodium hydroxide provided the highest stabilizing effect, the decomposition of the medicament X being reduced by adding only 1% of sodium hydroxide. Further, the stabilizing effect of magnesium oxide was similar to that of sodium hydroxide, the decomposition of the medicament X being significantly reduced by adding only 1% of magnesium oxide. The stabilizing effect of magnesium oxide was almost constant by adding 3% or more thereof.

Inhibition of Gelation

Example 2

1 mg Tablets

In a 20 L super mixer, 24 g of the medicament Y and 192 g of light anhydrous silicic acid (a gelation inhibitor, trade name: AEROSIL (registered trademark) 200, from Nippon Aerosil Co., Ltd.) were mixed, and thereto 1,236 g of D-mannitol (a diluent, from Towa Chemical Industry Co., Ltd.), 720 g of crystalline cellulose (a diluent, trade name: Avicel PH101, from Asahi Kasei Corporation), and 72 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a power mill to give the granules. With these granules, 120 g of croscarmellose sodium (a disintegrant, trade name: Ac-Di-Sol, from FMC International Inc.) and 36 g of sodium stearyl fumarate (a lubricant, from JRS Pharma LP) were mixed in a 20 L tumbler mixer, and tablets were formed by a tablet press to give the tablets, the total mass per tablet of which was 100 mg. Further, the tablets were coated with a 10% aqueous solution of opadry yellow (OPADRY03F42069 YELLOW, from Colorcon (Japan) Limited) by a tablet coating machine to give the coated tablets, the total mass per tablet of which was 105 mg.

Example 3

10 mg Tablets

In a 20 L super mixer, 60 g of the medicament Y and 192 g of light anhydrous silicic acid (a gelation inhibitor, trade name: AEROSIL (registered trademark) 200, from Nippon Aerosil Co., Ltd.) were mixed, and thereto 1,200 g of D-mannitol (a diluent, from Towa Chemical Industry Co., Ltd.), 720 g of crystalline cellulose (a diluent, trade name: Avicel PH101, from Asahi Kasei Corporation), and 72 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a power mill to give the granules. With these granules, 120 g of croscarmellose sodium (a disintegrant, trade name: Ac-Di-Sol, from FMC International Inc.) and 36 g of sodium stearyl fumarate (a lubricant, from JRS Pharma LP) were mixed in a 20 L tumbler mixer, and tablets were formed by a tablet press to give the tablets, the total mass per tablet of which was 400 mg. Further, the tablets were coated with a 10% aqueous solution of opadry yellow (OPADRY03F42069 YELLOW, from Colorcon (Japan) Limited) by a tablet coating machine to give the coated tablets, the total mass per tablet of which was 411 mg.

Example 4

100 mg Tablets

In a 1 L super mixer, 31.4 g of the medicament Y and 4 g of light anhydrous silicic acid (a gelation inhibitor, trade name: AEROSIL (registered trademark) 200, from Nippon Aerosil Co., Ltd.) were mixed, and thereto 40.1 g of anhydrous dibasic calcium phosphate (a diluent, from Kyowa Chemical Industry Co., Ltd.), 10 g of low-substituted hydroxypropylcellulose (a binder, trade name: L-HPC (LH-21), from Shin-Etsu Chemical Co., Ltd.), and 3 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a power mill to give the granules. With these granules, 10 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 400 mg.

Comparative Example 2

100 mg Tablets

In a 1 L super mixer, 31.4 g of the medicament Y, 44.1 g of anhydrous dibasic calcium phosphate (a diluent, from Kyowa Chemical Industry Co., Ltd.), 10 g of low-substituted hydroxypropylcellulose (a binder, trade name: L-HPC (LH-21), from Shin-Etsu Chemical Co., Ltd.), and 3 g of hydroxypropylcellulose (a binder, trade name: HPC-L, from Nippon Soda Co., Ltd.) were mixed. A suitable amount of absolute ethanol was then added thereto to give the pellets containing the medicament Y. These pellets were dried in a tray dryer (at 60° C.), and then the size of the pellets was controlled in a power mill to give the granules. With these granules, 10 g of croscarmellose sodium (a disintegrant, trade name: Ac-Di-Sol, from FMC International Inc.) and 1.5 g of sodium stearyl fumarate (a lubricant, from JRS Pharma LP) were mixed in a tumbler mixer, and tablets were formed by a tablet press to give the tablets, the total mass per tablet of which was 400 mg.

Example 5

100 mg Tablets 8% of Light Anhydrous Silicic Acid

In a 1 L super mixer, 31.4 g of the medicament Y and 8 g of light anhydrous silicic acid (a gelation inhibitor, trade name: AEROSIL (registered trademark) 200, from Nippon Aerosil Co., Ltd.) were mixed, and thereto 42.1 g of anhydrous dibasic calcium phosphate (a diluent, from Kyowa Chemical Industry Co., Ltd.), and 10 g of low-substituted hydroxypropylcellulose (a binder, trade name: L-HPC (LH-21), from Shin-Etsu Chemical Co., Ltd.) were further added and mixed. A suitable amount of absolute ethanol with 2 g of hydroxypropylcellulose (a binder, trade name: HPC-L, from Nippon Soda Co., Ltd.) suspended therein was then added thereto to give the pellets containing the medicament of the present invention. These pellets were dried in a tray dryer (at 60° C.), and then the size of the pellets was controlled in a power mill to give the granules. With these granules, 5 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 400 mg.

Example 6

100 mg Tablets 6% of Light Anhydrous Silicic Acid

In a 1 L super mixer, 31.4 g of the medicament Y and 6 g of light anhydrous silicic acid (a gelation inhibitor, trade name: AEROSIL (registered trademark) 200, from Nippon Aerosil Co., Ltd.) were mixed, and thereto 44.1 g of anhydrous dibasic calcium phosphate (a diluent, from Kyowa Chemical Industry Co., Ltd.), and 10 g of low-substituted hydroxypropylcellulose (a binder, trade name: L-HPC (LH-21), from Shin-Etsu Chemical Co., Ltd.) were further added and mixed. A suitable amount of absolute ethanol with 2 g of hydroxypropylcellulose (a binder, trade name: HPC-L, from Nippon Soda Co., Ltd.) suspended therein was then added thereto to give the pellets containing the medicament of the present invention. These pellets were dried in a tray dryer (at 60° C.), and then the size of the pellets was controlled in a power mill to give the granules. With these granules, 5 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 400 mg.

Example 7

100 mg Tablets 4% of Light Anhydrous Silicic Acid

In a 1 L super mixer, 31.4 g of the medicament Y and 4 g of light anhydrous silicic acid (a gelation inhibitor, trade name: AEROSIL (registered trademark) 200, from Nippon Aerosil Co., Ltd.) were mixed, and thereto 46.1 g of anhydrous dibasic calcium phosphate (a diluent, from Kyowa Chemical Industry Co., Ltd.), and 10 g of low-substituted hydroxypropylcellulose (a binder, trade name: L-HPC (LH-21), from Shin-Etsu Chemical Co., Ltd.) were further added and mixed. A suitable amount of absolute ethanol with 2 g of hydroxypropylcellulose (a binder, trade name: HPC-L, from Nippon Soda Co., Ltd.) suspended therein was then added thereto to give the pellets containing the medicament of the present invention. These pellets were dried in a tray dryer (at 60° C.), and then the size of the pellets was controlled in a power mill to give the granules. With these granules, 5 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 400 mg.

The storage test and the dissolution test were conducted for the tablets prepared above according to the methods described below.

(Storage Test)
Tablets in a glass bottle with the cap open were stored at 5° C., at 60° C. and 75% RH, at 40° C. and 75% RH, or at 30° C. and 65% RH.

(Dissolution Test)
The dissolution test was conducted according to the Japanese Pharmacopoeia 14th Edition and by the paddle method under the conditions described below. The test solution: 900 mL of 0.1 mol/L hydrochloric acid. The rotation speeds: 50 rpm. The temperature of the test solution: 37° C.

Experimental Example 1

Figure 2:
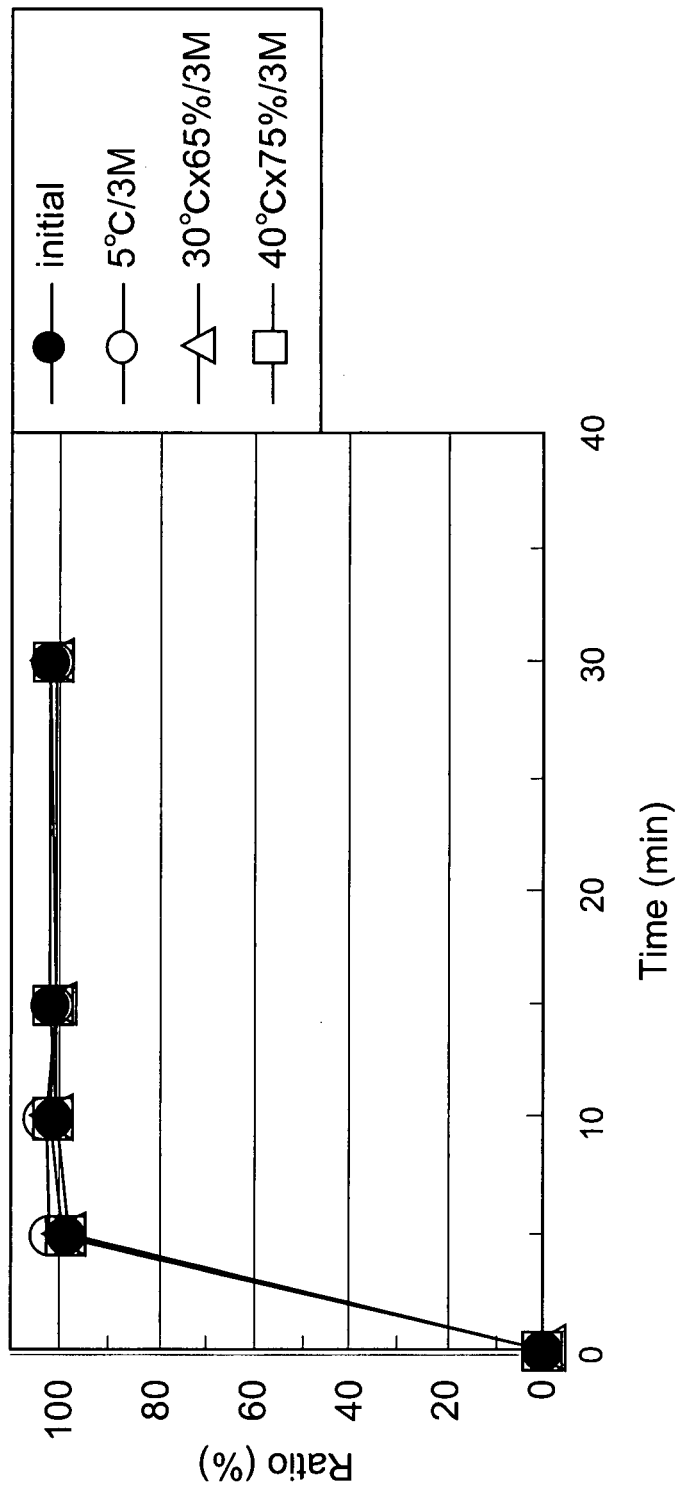
FIG. 2 illustrates the dissolution test results for the Example 2.
Figure 3:
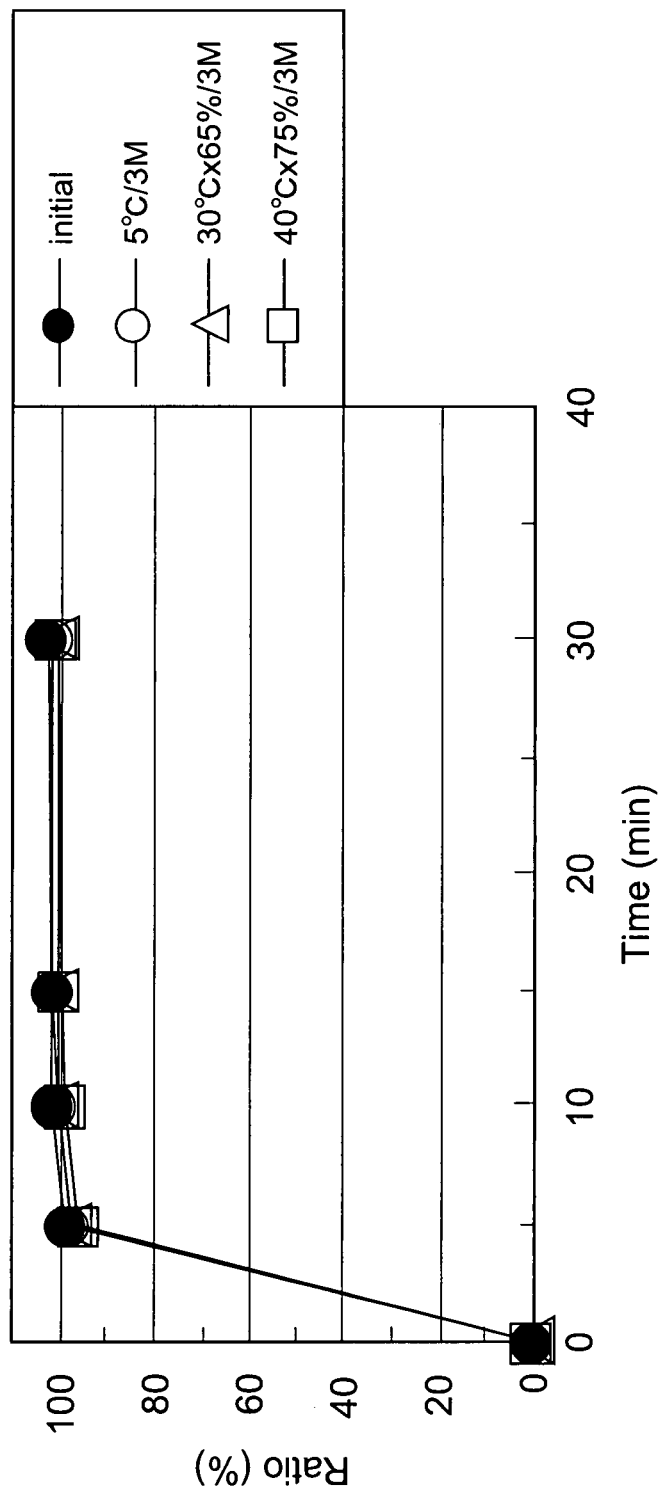
FIG. 3 illustrates the dissolution test results for the Example 3.

The storage test (the storage duration was 3 months) was conducted for the tablets prepared in Examples 2 and 3. No delayed dissolution was found for the tablets of both Examples at any of the conditions at 5° C., at 30° C. and 65% RH, and at 40° C. and 75% RH. The results of each of the examples are shown in FIGS. 2 and 3.

Experimental Example 2

Figure 4:
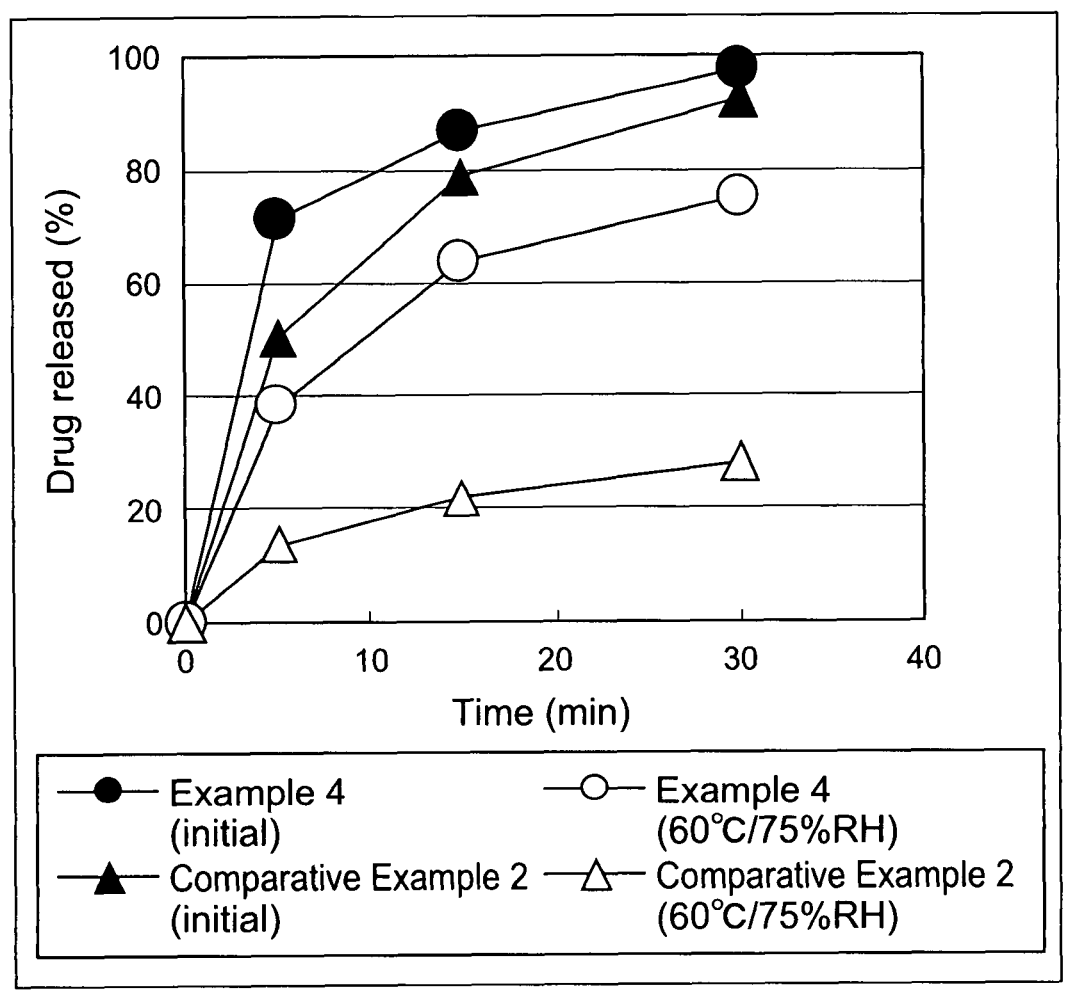
FIG. 4 illustrates the dissolution test results for the Example 4 and for the Comparative Example 2.

The tablets prepared in Example 4 and Comparative Example 2 were stored at 60° C. and 75% RH for 7 days. The tablets then underwent the dissolution test. The results are shown in FIG. 4. For the tablets of Comparative Example 2, the gelation of the tablet surface was noted even at the beginning of the test. Further, significant delayed dissolution was observed after the storage test. On the other hand, for the tablets of Example 4, the gelation on the surface was not noted on any of the tablets. The inhibition of delayed dissolution after the storage was also observed.

Experimental Example 3

Figure 5:
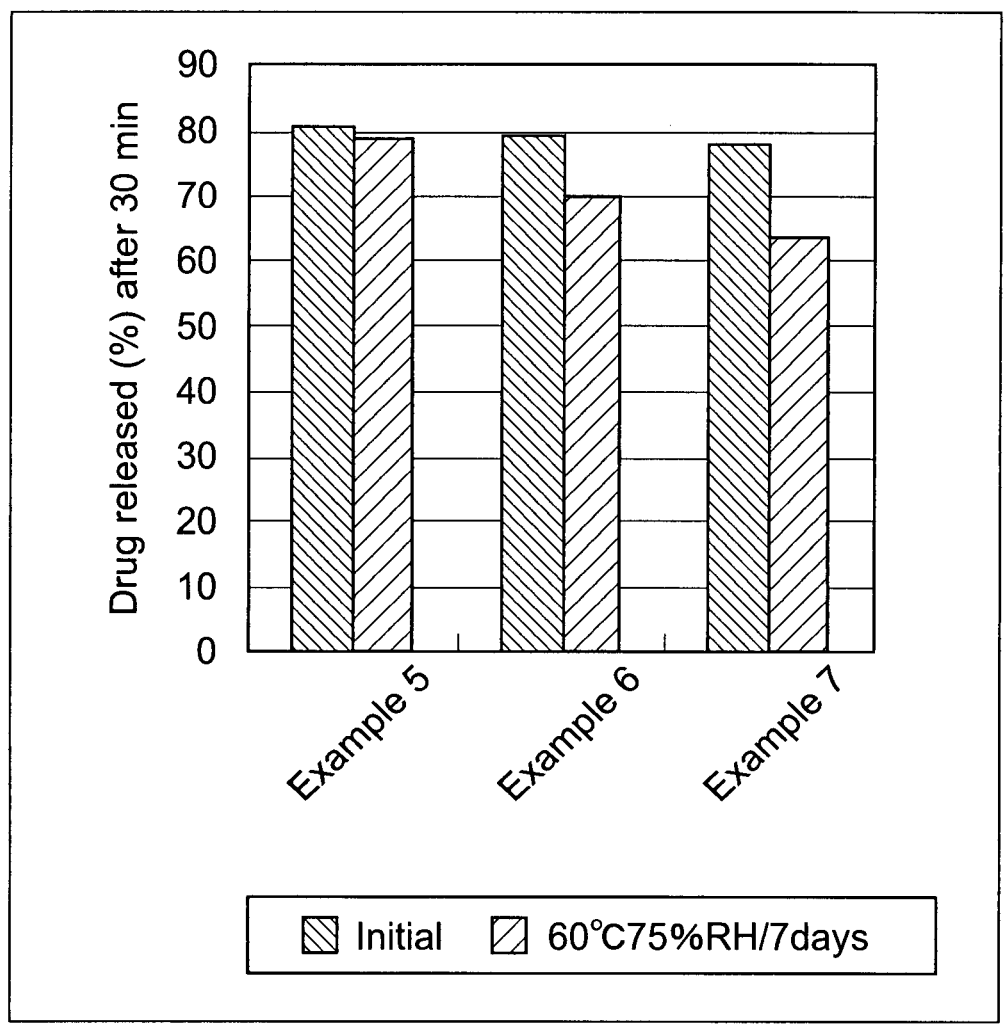
FIG. 5 illustrates the dissolution test results for the Examples 5, 6 and 7.

The tablets prepared in Examples 5 to 7 were stored at 60° C. and 75% RH for 7 days. The tablets then underwent the dissolution test. To confirm the influence of the amount of light anhydrous silicic acid contained in the tablet, the drug released (%) 30 min. after the dissolution test started was compared. The results are shown in FIG. 5. When from 16 to 32 mg of light anhydrous silicic acid was contained per 100 mg of the medicament Y, delayed dissolution seen in Comparative Example 2 was not observed. In particular, for the tablets of Example 5, wherein 32 mg of light anhydrous silicic acid was contained, delayed dissolution was barely seen after the storage as well.

The results shown above demonstrate that the addition of from 4 to 8% of the gelation inhibitor provides the pharmaceutical composition comprising the medicament X with great dissolution properties, while the gelation was effectively inhibited. Next examined were disintegration properties when higher levels of the gelation inhibitor was contained in the pharmaceutical composition. Disintegration properties when the stabilizer and the gelation inhibitor were contained therein were also examined. Disintegration properties were further examined, when silicone dioxide hydrate or calcium silicate was used in place of light anhydrous silicic acid as a gelation inhibitor.

Comparative Example 3

25 mg Tablets

To 7.85 g of the medicament Y, 22.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 8

25 mg Tablets 12% of Light Anhydrous Silicic Acid

In a 1 L super mixer, 7.85 g of the medicament Y and 6 g of light anhydrous silicic acid (a gelation inhibitor, trade name: AEROSIL (registered trademark) 200, from Nippon Aerosil Co., Ltd.) were mixed, and thereto 16.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 9

25 mg Tablets 20% of Light Anhydrous Silicic Acid

In a 1 L super mixer, 7.85 g of the medicament Y and 10 g of light anhydrous silicic acid (a gelation inhibitor, trade name: AEROSIL (registered trademark) 200, from Nippon Aerosil Co., Ltd.) were mixed, and thereto 12.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 10

25 mg Tablets 8% of Light Anhydrous Silicic Acid and 3% Magnesium Oxide

In a 1 L super mixer, 15.7 g of the medicament Y and 8 g of light anhydrous silicic acid (a gelation inhibitor, trade name: AEROSIL (registered trademark) 200, from Nippon Aerosil Co., Ltd.) were mixed, and thereto 3 g of magnesium oxide (a stabilizer, from Tomita Pharmaceutical Co., Ltd.), 33.8 g of D-mannitol (a diluent, from Towa Chemical Industry Co., Ltd.), 30 g of crystalline cellulose (a diluent, trade name: Avicel PH101, from Asahi Kasei Corporation), and 3 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 5 g of croscarmellose sodium (a disintegrant, trade name: Ac-Di-Sol, from FMC International Inc.) and 1.5 g of sodium stearyl fumarate (a lubricant, from JRS Pharma LP) were mixed, and tablets were formed by a tablet press to give the tablets, the total mass per tablet of which was 200 mg.

Example 11

25 mg Tablets 8% of Light Anhydrous Silicic Acid and 5% Disodium Hydrogenphosphate In a 1 L super mixer, 7.85 g of the medicament Y and 4 g of light anhydrous silicic acid (a gelation inhibitor, trade name:

AEROSIL (registered trademark) 200, from Nippon Aerosil Co., Ltd.) were mixed, and thereto 2.5 g of disodium hydrogenphosphate (a stabilizer, from Kanto Chemical Co., Inc.), 15.9 g of D-mannitol (a diluent, from Towa Chemical Industry Co., Ltd.), 15 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 12

25 mg Tablets 8% of Silicon Dioxide Hydrate

In a 1 L super mixer, 7.85 g of the medicament Y and 4 g of silicon dioxide hydrate (a gelation inhibitor, trade name: Sylysia, from Fuji Silysia Chemical Ltd.) were mixed, and thereto 18.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

Example 13

25 mg Tablets 8% of Calcium Silicate

In a 1 L super mixer, 7.85 g of the medicament Y and 4 g of calcium silicate (a gelation inhibitor, trade name: Florite (registered trademark), from Tokuyama Corp.) were mixed, and thereto 18.4 g of D-mannitol (a diluent, from Towa Chemical Industry Co., Ltd.), 15.0 g of crystalline cellulose (a diluent, trade name: Avicel PH101, from Asahi Kasei Corporation), and 1.5 g of hydroxypropylcellulose (a binder, trade name: HPC-L, from Nippon Soda Co., Ltd.) were further added and mixed. A suitable amount of absolute ethanol was then added thereto to give the pellets containing the medicament Y. These pellets were dried in a tray dryer (at 60° C.), and then the size of the pellets was controlled in a small speed mill to give the granules. With these granules, 2.5 g of croscarmellose sodium (a disintegrant, trade name: Ac-Di-Sol, from FMC International Inc.) and 0.8 g of sodium stearyl fumarate (a lubricant, from JRS Pharma LP) were mixed, and tablets were formed by a tablet press to give the tablets, the total mass per tablet of which was 200 mg.

The disintegration test was conducted for the tablets prepared above by the method described in the Japanese Pharmacopoeia 14th Edition. The disintegration time is summarized in Table 4.

TABLE 4

| Sample | Disintegration time |
|---|---|
| Comparative Example 3 | 15 min. or longer |
| Example 8 | 1.2 to 1.4 min. |
| Example 9 | 0.9 to 1.1 min. |
| Example 10 | 3.9 to 4.1 min. |
| Example 11 | 2.9 to 3.1 min. |
| Example 12 | 7.6 to 8.2 min. |
| Example 13 | 2.3 to 2.5 min. |

The tablets of any of Examples 8 to 13 had a shorter disintegration time than those from Comparative Example 3. It is shown that disintegration properties of the tablets prepared in Examples 8 to 13 were superior. The above demonstration confirms that the pharmaceutical composition of the present invention inhibits the gelation effectively.

Formulation Examples

Formulation examples comprising the crystals (C) of methanesulfonate of 4-(3-chloro-4-(cyclopropylaminocarbonyl)aminophenoxy)-7-methoxy-6-quinolinecarboxamide (the medicament X) synthesized in the above "Preparation of Medicament (Active Ingredient)" are shown. In Table 5, a formulation of a 10 mg tablet (a coated tablet) and in Table 6, a formulation of a 100 mg tablet (a coated tablet) are illustrated.

TABLE 5

| Material | Purpose | Amount contained (mg) |
|---|---|---|
| The compound | Active ingredient | 12.3 |
| Magnesium oxide | Stabilizer | 10 |
| Anhydrous dibasic calcium phosphate | Diluent | 150.7 |
| D-Mannitol | Diluent | 153 |
| Partially alpha starch | Disintegrant | 20 |
| Crystalline cellulose | Diluent | 16 |
| Hydroxypropylcellulose | Binder | 12 |
| Subtotal | | 374 |
| Croscarmellose sodium | Disintegrant | 20 |
| Sodium stearyl fumarate | Lubricant | 6 |
| Subtotal | | 400 |
| Opadry yellow | Coating agent | 11 |
| Total | | 411 |

TABLE 6

| Material | Purpose | Amount contained (mg) |
|---|---|---|
| The compound | Active ingredient | 122.5 |
| Magnesium oxide | Stabilizer | 10 |
| Anhydrous dibasic calcium phosphate | Diluent | 37.5 |
| Partially alpha starch | Disintegrant | 20 |
| Croscarmellose sodium | Disintegrant | 20 |
| Purified water | Solvent | q.s. |
| Subtotal | | 210 |
| Anhydrous dibasic calcium phosphate | Disintegrant | 136 |
| Croscarmellose sodium | Lubricant | 8 |
| Crystalline cellulose | Diluent | 16 |

TABLE 6-continued

| Material | Purpose | Amount contained (mg) |
|---|---|---|
| Hydroxypropylcellulose | Disintegrant | 4 |
| Purified water | Solvent | q.s. |
| Subtotal | | 374 |
| Croscarmellose sodium | Disintegrant | 20 |
| Sodium stearyl fumarate | Lubricant | 6 |
| Subtotal | | 400 |
| Opadry yellow | Coating agent | 11 |
| Total | | 411 |

In Tables 5 and 6, "the compound" refers to the crystals (C) of methanesulfonate of 4-(3-chloro-4-(cyclopropylaminocarbonyl)aminophenoxy)-7-methoxy-6-quinolinecarboxamide (the medicament X), and "opadry yellow" refers to a pre-mixed materials consisting of Hydroxypropylmethylcellulose 2910, talc, Macrogol 6000 (molecular weight: 8,000), titanium oxide, and yellow iron sesquioxide in 56.0, 28.0, 10.0, 4.0, and 2.0% (w/w), respectively.

A 10 mg tablet was formulated by the following processes. The active ingredient, magnesium oxide, anhydrous dibasic calcium phosphate, D-mannitol, partially alpha starch, crystalline cellulose, and hydroxypropylcellulose were mixed, and then thereto a suitable amount of purified water was added to prepare pellets. These pellets were dried, and then the size of the pellets was controlled. To the resulting granules, croscarmellose sodium and sodium stearyl fumarate were added and mixed, and a tablet was formed. On the resulting tablet, a film of opadry yellow was coated by a fluidized bed coating technique.

A 100 mg tablet was formulated by the following processes. The active ingredient, magnesium oxide, anhydrous dibasic calcium phosphate, partially alpha starch, and croscarmellose sodium were mixed, and then thereto a suitable amount of purified water was added to prepare pellets. These pellets were dried, and then the size of the pellets was controlled. To the resulting pellets, anhydrous dibasic calcium phosphate, croscarmellose sodium, crystalline cellulose, and hydroxypropylcellulose were added and mixed, and then thereto a suitable amount of purified water was added to prepare granules. These granules were dried, and then the size of the granules was controlled. To the resulting granules, croscarmellose sodium and sodium stearyl fumarate were added and mixed, and a tablet was formed. On the resulting tablet, a film of opadry yellow was coated by a fluidized bed coating technique.

INDUSTRIAL APPLICABILITY

The pharmaceutical composition in accordance with the present invention is highly stable, and hence is clinically useful.

The invention claimed is:

1. A pharmaceutical composition comprising:
   an active ingredient consisting of 4-(3-chloro-4-(cyclopropylaminocarbonyl)aminophenoxy)-7-methoxy-6-quinolinecarboxamide, or a salt thereof;
   (i) 1-10 w/w % of one or more compounds selected from the group consisting of magnesium oxide, sodium carbonate, disodium hydrogenphosphate, sodium citrate, dipotassium hydrogenphosphate, sodium acetate, sodium hydrogencarbonate, and sodium hydroxide, and
   (ii) one or more compounds selected from the group consisting of light anhydrous silicic acid, silicon dioxide hydrate, and calcium silicate.

2. The pharmaceutical composition according to claim 1, wherein the compound (i) is magnesium oxide.

3. The pharmaceutical composition according to claim 1, wherein the active ingredient is crystals of hydrochloride, hydrobromide, p-toluenesulfonate, sulfate, methanesulfonate, or ethansulfonate of 4-(3-chloro-4-(cyclopropylaminocarbonyl)aminophenoxy)-7-methoxy-6-quinolinecarboxamide.

4. The pharmaceutical composition according to claim 1, where the active ingredient is crystals of methanesulfonate of 4-(3-chloro-4-(cyclopropylaminocarbonyl)aminophenoxy)-7-methoxy-6-quinolinecarboxamide.

5. The pharmaceutical composition according to claim 1, wherein the compound (i) is magnesium oxide, and the compound (ii) is light anhydrous silicic acid.

6. The pharmaceutical composition according to claim 1, wherein the compound (i) is magnesium oxide, disodium hydrogenphosphate, sodium hydrogencarbonate, or sodium hydroxide, and the compound (ii) is light anhydrous silicic acid.

7. The pharmaceutical composition according to claim 1, wherein the compound (i) is magnesium oxide or disodium hydrogenphosphate, and the compound (ii) is one of light anhydrous silicic acid, silicon dioxide hydrate or calcium silicate.

* * * * *

UNITED STATES PATENT AND TRADEMARK OFFICE
CERTIFICATE OF CORRECTION

PATENT NO. : 8,969,379 B2
APPLICATION NO. : 11/662425
DATED : March 3, 2015
INVENTOR(S) : Hisao Furitsu and Yasuyuki Suzuki It is certified that error appears in the above-identified patent and that said Letters Patent is hereby corrected as shown below:

On the Title Page, left column Item (54) and in the Specification, Column 1, line 1

Delete "PHARMACEUTICAL COMPOSITIONS OF 4-(3-CHLORO-4-(CYCLOPROPYLAMINOCARBONYL)AMINOPHENOXY)-7=METHOXY-6-QUINOLINECARBOXAMIDE" and replace
it with --PHARMACEUTICAL COMPOSITIONS OF 4-(3-CHLORO-4-(CYCLOPROPYLAMINOCARBONYL)AMINOPHENOXY)-7-METHOXY-6-QUINOLINECARBOXAMIDE--.

Signed and Sealed this
Eleventh Day of August, 2015

Michelle K. Lee
*Director of the United States Patent and Trademark Office*